US006953577B2

(12) United States Patent
Sympson et al.

(10) Patent No.: US 6,953,577 B2
(45) Date of Patent: Oct. 11, 2005

(54) HUMAN METHIONINE AMINOPEPTIDASE TYPE 3

(75) Inventors: Carolyn J. Sympson, Ballwin, MO (US); Rajeev Aurora, Glencoe, MO (US); Stanton B. Dotson, Chesterfield, MO (US); Ronald B. Frazier, Lake St. Louis, MO (US); Cynthia L. Woods, St. Peters, MO (US); Hamideh Zakeri, Chesterfield, MO (US); Xianzhi Zhou, Chesterfield, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/299,867

(22) Filed: Nov. 19, 2002

(65) Prior Publication Data

US 2003/0203406 A1 Oct. 30, 2003

Related U.S. Application Data

(63) Continuation-in-part of application No. 09/523,263, filed on Mar. 10, 2000, now Pat. No. 6,638,750.

(60) Provisional application No. 60/125,139, filed on Mar. 11, 1999.

(51) Int. Cl.[7] .......................... A01N 63/00; C12N 9/48; C12N 1/20; C12N 15/00; C07H 21/04

(52) U.S. Cl. ................. 424/94.63; 435/212; 435/252.3; 435/320.1; 536/23.2; 536/23.6

(58) Field of Search ....................... 424/94.63; 435/212, 435/252.3, 320.1; 536/23.2, 23.6

(56) References Cited

PUBLICATIONS

Sequence alignment between Accession No. T50575 and SEQ ID No: 8 [Redenbach et al. Mol. Microbiol. 21, 77–96 (1996)].*

* cited by examiner

*Primary Examiner*—Tekchand Saidha
(74) *Attorney, Agent, or Firm*—Harness, Dickey & Pierce, PLC

(57) ABSTRACT

Methionine aminopeptidases catalyse the co-translational removal of amino terminal methionine residues from nascent polypeptide chains. A newly-discovered enzyme, designated methionine aminopeptidase type-3 (MetAP-3), has a substrate specificity which is similar to MetAP-1 and MetAP-2, although it is not inhibited by fumagillin, an irreversible inhibitor of MetAP-2. MetAP-3 also preferentially localizes to mitochondria, unlike MetAP-1 and MetAP-2, which accumulate in the cytoplasm. One embodiment of the present invention relates to human cDNAs encoding polypeptides comprising MetAP-3. Other embodiments of the invention relate to nucleic acid molecules derived from these cDNAs, including complements, homologues, and fragments thereof, and methods of using these nucleic acid molecules, to generate polypeptides and fragments thereof. Other embodiments of the invention relate to antibodies directed against polypeptides comprising MetAP-3, and methods to screen for compounds or compositions that preferentially or specifically effect the activity of polypeptides comprising MetAP-3.

5 Claims, 20 Drawing Sheets

*Figure 1A - Phylogenetic comparison of methionine aminopeptidases*
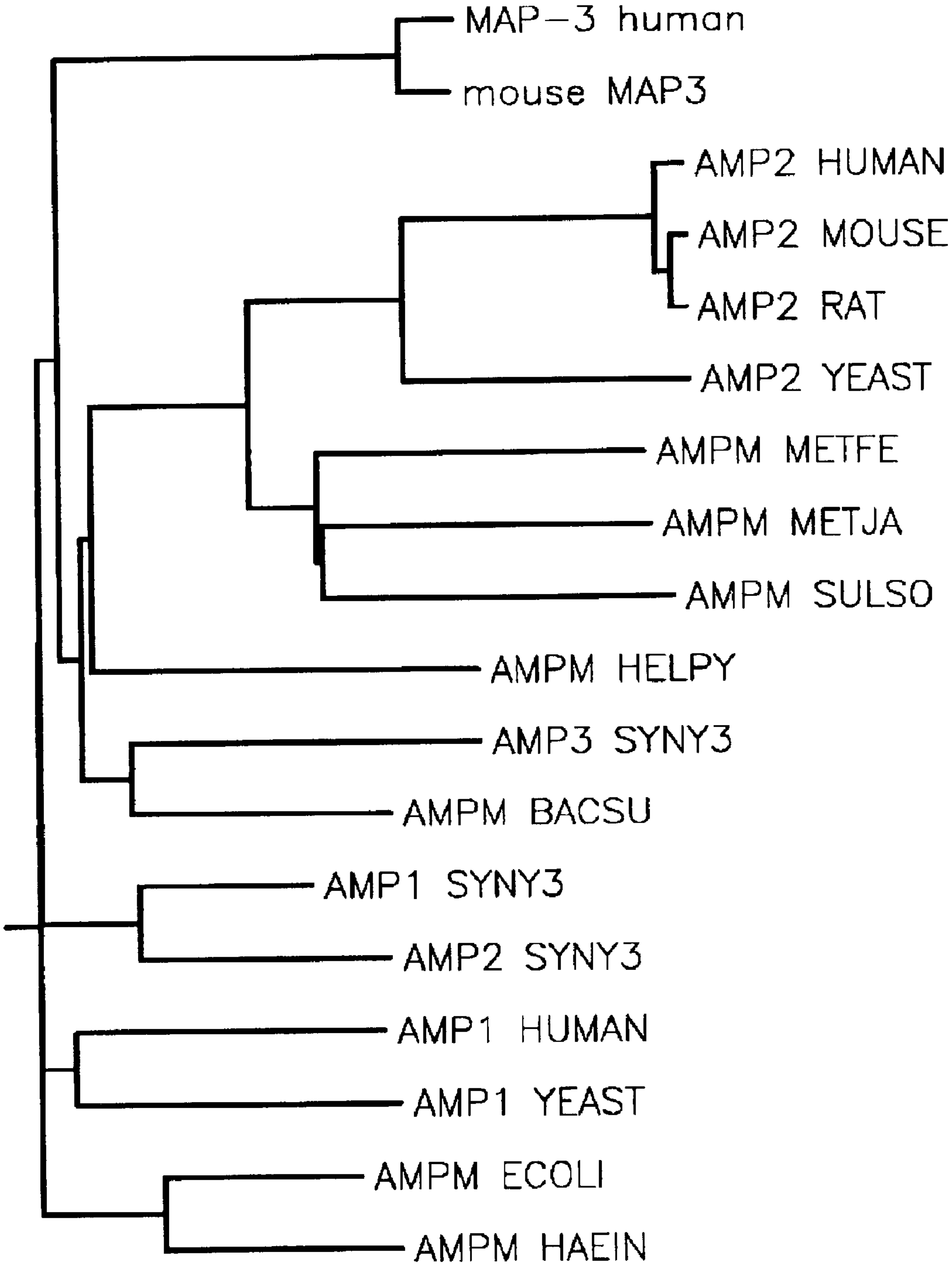

*Figure 1B - Phylogenetic comparison of methionine aminopeptidases*
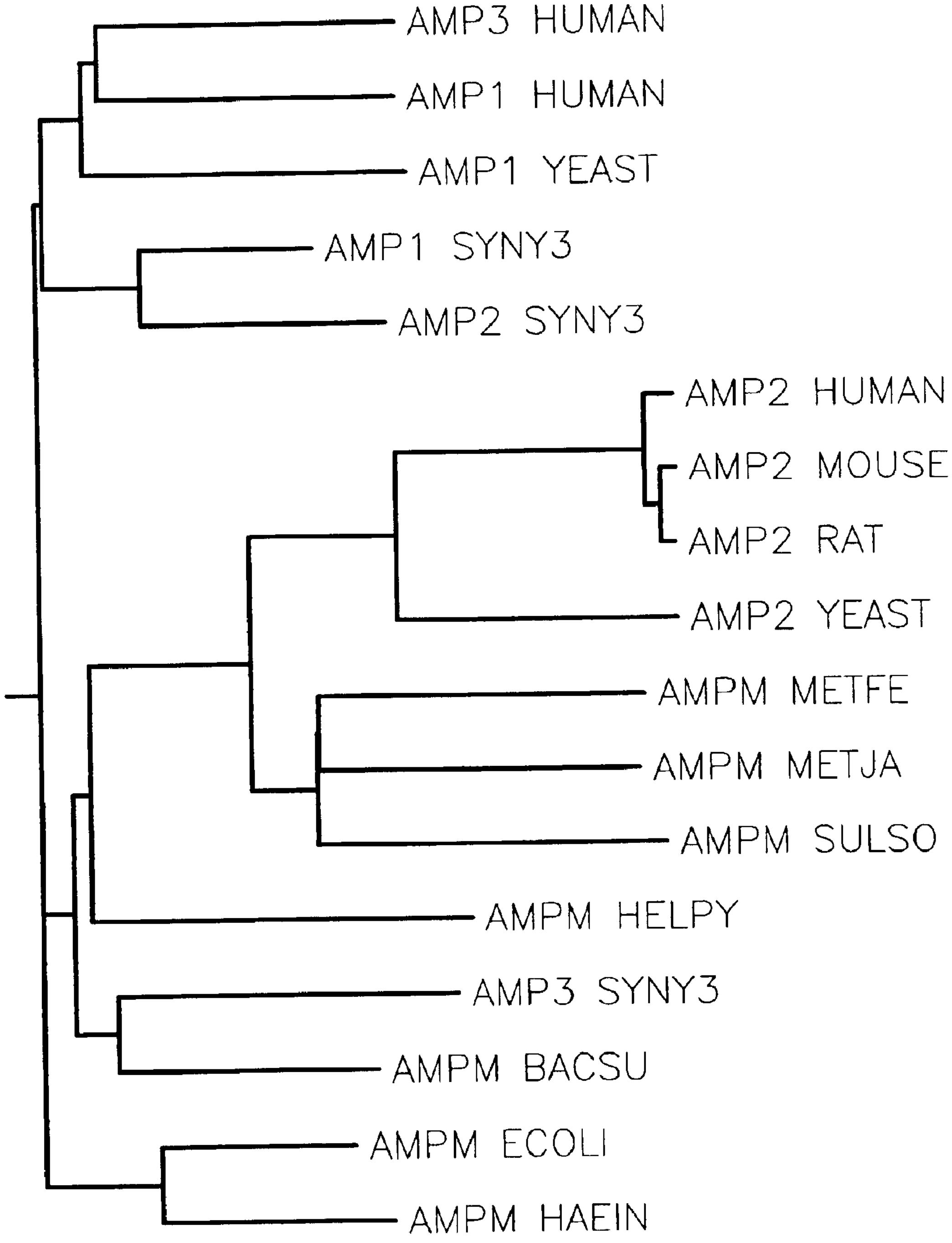

*Figure 1C - Phylogenetic comparison of methionine aminopeptidases*
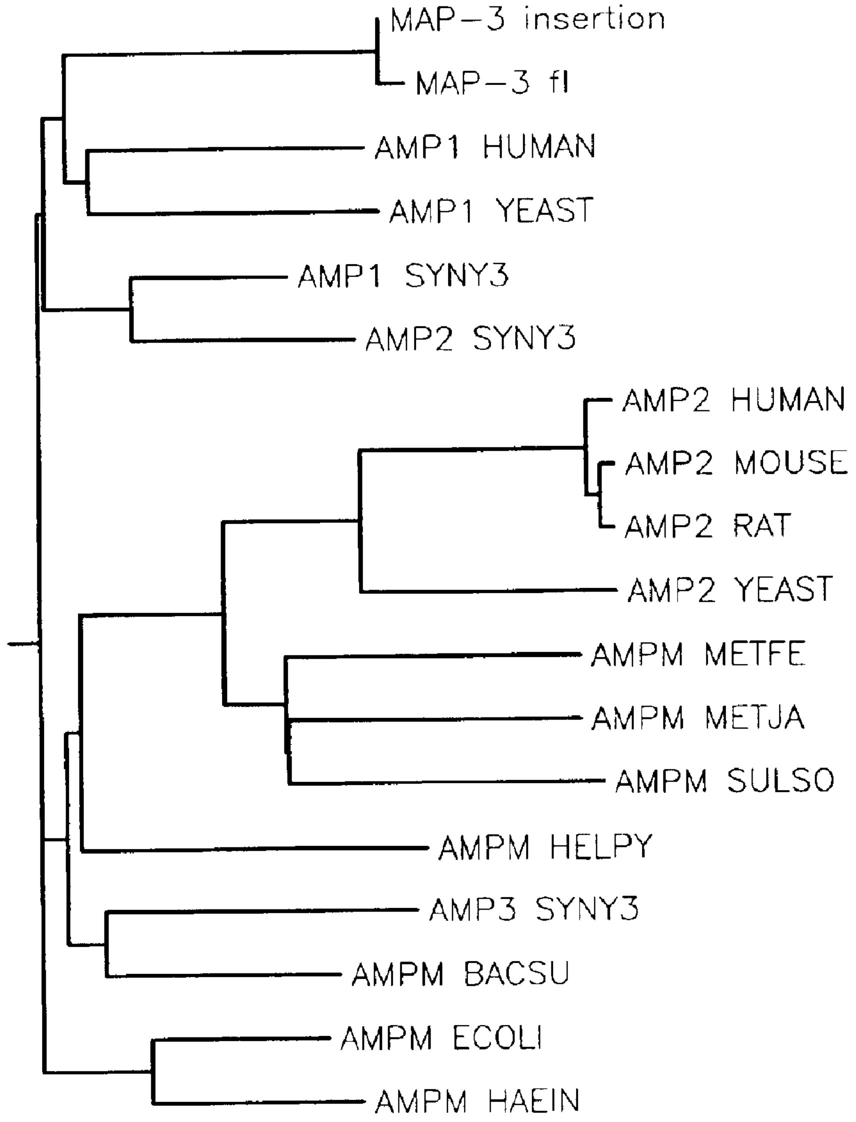

*Figure 2Aa - Alignment and boxshade display of methionine aminopeptidases*

```
MAP-3 human    1 -----------------------------------------------------MAAPSGVHLLVRRGSHR
mouse MAP3     1 -----------------------------------------------------MAAPICVPLLVRGGCQR
AMPM_ECOLI     1 ----------------------------------------------------------------------
AMPM_HAEIN     1 ----------------------------------------------------------------------
AMP1_HUMAN     1 -------------------ALFQRAGSMAAVETRV-CBTDGCS--SEAKLQCPTCIKLGIQGSYFCSQEC
AMP1_YEAST     1 ---------------MSTATTTVTTSDQASHPTKIYCSGLQCGRETSSQMKCPVCLKQGIV-SIFCDTSC
AMP1_SYNY3     1 ----------------------------------------------------------------------
AMP2_SYNY3     1 ----------------------------------------------------------------------
AMP3_SYNY3     1 ----------------------------------------------------------------------
AMPM_BACSU     1 ----------------------------------------------------------------------
AMP2_MOUSE     1 MAGVEQAASFGGHLNGDLDPDDREEGTSSTARRAAKKKRRKKKKGKGAVSAVQQELDKESGALVDEVAKQ
AMP2_RAT       1 MAGVEEASSFGGHLNRDLDPDDREEGTSSTAEEAAKKKRRKKKKGKGAVSAGQQELDKESGTSVDEVAKQ
AMP2_HUMAN     1 MAGVEEVAASGSHLNGDLDPDDREECAASTAEEAAKKKRRKKKKSKGPSAACEQEPDKESCASVDEVARQ
AMP2_YEAST     1 ----------------------------------------------------MTDAEIENSPASDLKELN
AMPM_METJA     1 ----------------------------------------------------------------------
AMPM_SULSO     1 ----------------------------------------------------------------------
AMPM_METFE     1 ----------------------------------------------------------------------
AMPM_HELPY     1 ----------------------------------------------------------------------
consensus      1

MAP-3 human   18 IPSSPLNHIYLHKQSSSQQRR------------NFFFRRQRDISHSIVLPAAVSSAHPVPKHIKKPDYVT
mouse MAP3    18 ILSSPLNHIYLHKRSGSQQRR------------HFPPWRQRDISHSVVSPAAVSPAHPVPKRIKKPDYVT
AMPM_ECOLI     1 ----------------------------------------------------------------------
AMPM_HAEIN     1 ----------------------------------------------------------------------
AMP1_HUMAN    49 FKGSWATHKLLHKKAKDRKAKREVSSWTVEGDINTDPWAGYRYTGKLRPHYPLMPTRPVPSYIQRPDYAD
AMP1_YEAST    55 YENNYKAHKALHN-AKDG----------LEG--AYDPFPKFKYSGKVKASYPLTPRRYVPRDIPKPDWAA
AMP1_SYNY3     1 ----------------------------------------------------------------------
AMP2_SYNY3     1 ------------------------------------------------------------------HNHQ
AMP3_SYNY3     1 ----------------------------------MPRIFPWKLWRKSRPAWPRFLGTHPMNLLSQLFAPP
AMPM_BACSU     1 ----------------------------------------------------------------------
AMP2_MOUSE    71 LESQALEEKERDDDDEDGDGDADGATGKKKKKKKKKRGPKVQTDPPSVPICDLYPNGVFPKGQECEYPPT
AMP2_RAT      71 LERQALEEKEKDDDDEDGDGDGDGAAGKKKKKKKKKRGPRVQTDPPSVPICDLYPNGVFPKGQECEYPPT
AMP2_HUMAN    71 LERSALEDKERDEDDEDGDGDGDGATGKKKKKKKKKRGPKVQTDPPSVPICDLYPNGVFPKGQECEYPPT
AMP2_YEAST    19 LENEGVEQQDQAKADESDPVESK----KKKNKKKKKKKSNVKK------IELLPPDGKYPEGAWMDY--H
AMPM_METJA     1 ----------------------------------------------------------------------
AMPM_SULSO     1 ----------------------------------------------------------------------
AMPM_METFE     1 ----------------------------------------------------------------------
AMPM_HELPY     1 ----------------------------------------------------------------------
consensus     71

MAP-3 human   76 TG--IVP-----DWGDSIEVKNE--DQHQCLHQACQLARHVLLLAGKSLKVDMTTEEIDALVHREIISHN
mouse MAP3    76 TG--IVP-----DWGDSIEVKDE--DQIQCLREACRLARHVLLLAGKSLKVDMTTEEIDALVHWEIIRHD
AMPM_ECOLI     1 ---------------MAISIKTP--EDIEKMRVAGRLAAEVLEMIEPYVKPGVSTGELDRICNDYIVNEQ
AMPM_HAEIN     1 ---------------MAIPIRTE--KEIVKLREACKLASDVLVMIEPYVKAGVTTGELDRICHEYMVNEQ
AMP1_HUMAN   119 HPLGHSRSEQALKGTSQIKLLSS--EDIEGMRLVCRLAREVLDVAAGMIKPGVTTEEIDHAVHLACIARN
AMP1_YEAST   112 N--GLPVSEQRNDRLNNIPIYKK--DQIKKIRKACMLGREVLDIAAAHVRPGITTDELDEIVHNETIKRG
AMP1_SYNY3     1 -------------MGDTITLLSR--REIEKMRQAGQLAAALLDHLAPMVQPGITTLELNDEAEKWTKAHG
AMP2_SYNY3     5 NLLSITRNLVHPPISSGLVLLSA--RELDKMRRVGQLAANLLNHLESMVQPGVSTQALNDEATRWMEDHG
AMP3_SYNY3    37 SPVPSPTPKAKKRSRRGVQIKTP--AEIAIMRQAGAIAAQVLKEIAATVQPGMTTGDLDQLAEERIRSLG
AMPM_BACSU     1 ----------------MIICKTP--RELGIMREAGRIVALTHEELKKHIKPGISTKELDQIAERFIKKQG
AMP2_MOUSE   141 QDGRTAAWRTTSEEKKALDQASE--EIWNDFREAAEAHRQVRKYVMSWIKPGMTMIEICEKLEDCSRK--
AMP2_RAT     141 QDGRTAAWRTTSEEKKALDQASE--EIWNDFREAAEAHRQVRKYVMSWIKPGMTMIEICEKLEDCSRK--
AMP2_HUMAN   141 QDGRTAAWRTTSEEKKALDQASE--EIWNDFREAAEAHRQVRKYVMSWIKPGMTMIEICEKLEDCSRK--
AMP2_YEAST    77 QDFN--LQRTTDEESRYLKRDLERAEHWNDVRKGAEIHRRVRRAIKDRIVPGMKLMDIADMIENTTRKYT
AMPM_METJA     1 --------------------MEI--EGYEKIIEACKIASKVREEAVKLIKPGVKLLEVAEFVENRIRE--
AMPM_SULSO     1 --------------------MTE--DELNKLLLACKIAAKARDEVSLDVKASAKVLDLCEEVESIIIE--
AMPM_METFE     1 ---------------------------MEKFEKAGKIASKVRKKAIKAVKGEMKILDLAEPIENEIEK--
AMPM_HELPY     1 ---------------MAISIKSP--KEIKALRKACKLTAQALALLEREVRPGVSLLELDKMAEDFIKSSH
consensus    141                 . . .     ...  ..  ..  ..  ..   .   ................  ..
```

*Figure 2Ab - Alignment and boxshade display of methionine aminopeptidases*
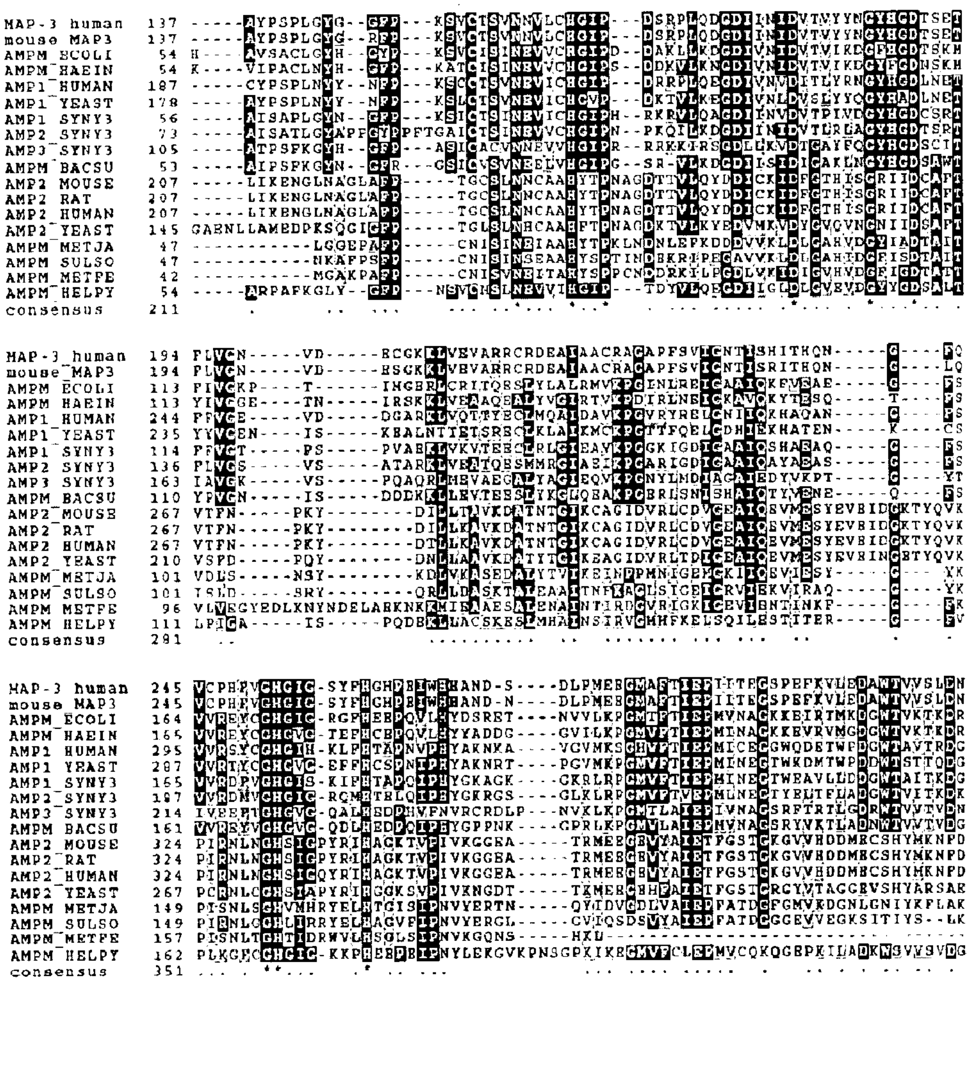

*Figure 2Ac - Alignment and boxshade display of methionine aminopeptidases*

```
MAP-3 human   309 QR-----SAQFEHTVLITSRGAQILTKLPHEA-------------------------------------
mouse MAP3    309 QR-----SAQFEHTVLITPRGVEILTKLPQEA-------------------------------------
AMPM_ECOLI    229 SL-----SAQYEHTIVVTDNGCEILTLRKDDTIPAIISHDE----------------------------
AMPM_HAEIN    230 SH-----SACYEHQLIVTETGCEVMTIRDEEIAEGRISRIMVNV-------------------------
AMP1_HUMAN    360 KR-----SAQFEHTLLVTDTGCEILTRRLDSARPHFMSQF-----------------------------
AMP1_YEAST    352 KL-----SAQFEHTLLVTEHGVEILTARNKKS-PGGPRQRIK---------------------------
AMP1_SYNY3    230 KL-----SAQFEHTIAVTEDGVEILTLGE----------------------------------------
AMP2_SYNY3    252 KL-----SAQFEHTVVVTEEGVEILTLA-----------------------------------------
AMP3_SYNY3    280 AL-----SAQFEHTVLVTATGYELLTDRRLV--------------------------------------
AMPM_BACSU    226 KK-----CAHFEHTIAITETGFDILTRV-----------------------------------------
AMP2_MOUSE    389 VGHVPIRLPRTKHLLNVINENPGTLAFCRRWLDRLGE--SKYLMALKNLCDLGIVDPYPPLCDIKGSYTA
AMP2_RAT      389 VGHVPIRLPRTKHLLNVINENPGTLAFCRRWLDRLGE--SKYLMALKNLCDLGIVDPYPPLCDIKGSYTA
AMP2_HUMAN    389 VGHVPIRLPRTKHLLNVINENPGTLAFCRRWLDRLGE--SKYLMALKNLCDLGIVDPYPPLCDIKGSYTA
AMP2_YEAST    332 DHQVMPTLDSAKNLLKTIDRNFGTLPFCRRYLDRLGQ--EKYLFALNNLVRHGLVQDYPPLNDIPGSYTA
AMPM_METJA    214 RP-IRLPQAR--KLLDVISKNYPYLPPAERWVLKNES----ERLALNSLIRASCIYGYPILKERENGIVG
AMPM_SULSO    212 NPNIKGLSSRENELIDFIYTRFNYLPFSERWLKEFSTNVDELRNNIKNLVKKGALRGYPILIEIKKGVVS
AMPM_METFE        ----------------------------------------------------------------------
AMPM_HELPY    231 LN-----TSHHEHTIAIVGNKAVILTER------------------------------------------
consensus     421        .........  ..    .  ....

MAP-3_human       ----------------------
mouse_MAP3        ----------------------
AMPM_ECOLI        ----------------------
AMPM_HAEIN        ----------------------
AMP1_HUMAN        ----------------------
AMP1_YEAST        ----------------------
AMP1_SYNY3        ----------------------
AMP2_SYNY3        ----------------------
AMP3_SYNY3        ----------------------
AMPM_BACSU        ----------------------
AMP2_MOUSE    457 QPEHTILLRPTCKEVVSRGDDY
AMP2_RAT      457 QPEHTILLRPTCKEVVSRGDDY
AMP2_HUMAN    457 QPEHTILLRPTCKEVVSRGDDY
AMP2_YEAST    400 QPEHTILLHAHKKEVVSKGDDY
AMPM_METJA    277 QAEHTILITENGVEITTK----
AMPM_SULSO    282 QPEHTVIVKGDSIIVSTKSL--
AMPM_METFE        ----------------------
AMPM_HELPY        ----------------------
consensus     491
```

*Figure 2Ba - Multiple sequence alignment and Clustal display of methionine aminopeptidases*

```
MAP-3_insertion  ------------------------------------------------------------
MAP-3_f1         -------------------------------------------------------MAAPS
AMP1_HUMAN       ---------------------ALFQRAGSMAAVETRV-CETDGCS--SEAKLQCPTCIKL
AMP1_YEAST       -----------------MSTATTTVTTSDQASHPTKIYCSGLQCGRETSSQMKCPVCLKQ
AMP1_SYNY3       ------------------------------------------------------------
AMP2_SYNY3       ------------------------------------------------------------
AMPM_ECOLI       ------------------------------------------------------------
AMPM_HAEIN       ------------------------------------------------------------
AMP3_SYNY3       ------------------------------------------------------------
AMPM_BACSU       ------------------------------------------------------------
AMP2_MOUSE       MAGVEQAASFGGHLNGDLDPDDREEGTSSTAEEAAKKKRRKKKKGKGAVSAVQQELDKES
AMP2_RAT         MAGVEEASSFGGHLNRDLDPDDREEGTSSTAEEAAKKKRRKKKKGKGAVSAGQQELDKES
AMP2_HUMAN       MAGVEEVAASGSHLNGDLDPDDREEGAASTAEEAAKKKRRKKKKSKGPSAAGEQEPDKES
AMP2_YEAST       ----------------------------------------------------MTDAEIEN
AMPM_METJA       ------------------------------------------------------------
AMPM_SULSO       ------------------------------------------------------------
AMPM_METFE       ------------------------------------------------------------
AMPM_HELPY       ------------------------------------------------------------

MAP-3_insertion  ------------------------------------------------------------
MAP-3_f1         GVHLLVRRGSHRIFSSPLNHIYLHKQSSSQ-------------QRRNFFRRQRDISHSIV
AMP1_HUMAN       GIQGSYFCSQECFKGSWATHKLLHKKAKDEKAKREVSSWTVEGDINTDPWAGYRYTGKLR
AMP1_YEAST       GIV-SIFCDTSCYENNYKAHKALHN-AKDG----------LEG--AYDPFPKFKYSGKVK
AMP1_SYNY3       ------------------------------------------------------------
AMP2_SYNY3       ------------------------------------------------------------
AMPM_ECOLI       ------------------------------------------------------------
AMPM_HAEIN       ------------------------------------------------------------
AMP3_SYNY3       ----------------------------------------------MPRIFPWKLWRKSR
AMPM_BACSU       ------------------------------------------------------------
AMP2_MOUSE       GALVDEVAKQLESQALEEKERDDDDEDGDGDADGATGKKKKKKKKKRGPKVQTDPPSVPI
AMP2_RAT         GTSVDEVAKQLERQALEEKEKDDDDEDGDGDGDGAAGKKKKKKKKKRGPRVQTDPPSVPI
AMP2_HUMAN       GASVDEVARQLERSALEDKERDEDDEDGDGDGDGATGKKKKKKKKKRGPKVQTDPPSVPI
AMP2_YEAST       SPASDLKELNLENEGVEQQDQAKADESDPVESK---KKKNKKKKKKKSNVKK------I
AMPM_METJA       ------------------------------------------------------------
AMPM_SULSO       ------------------------------------------------------------
AMPM_METFE       ------------------------------------------------------------
AMPM_HELPY       ------------------------------------------------------------

MAP-3_insertion  ------------------------------------------------------------
MAP-3_f1         LPAAVSSAHPVPKHIKKPDYVTT-------GTVPDWGDSIEVKNEDQIQGLHQACQLARH
AMP1_HUMAN       PHYPLMPTRPVPSYIQRPDYADHPLGMSESEQALKGTSQIKLLSSEDIEGMRLVCRLARE
AMP1_YEAST       ASYPLTPRRYVPEDIPKPDWAAN--GLPVSEQRNDRLNNIPIYKKDQIKKIRKACMLGRE
AMP1_SYNY3       -----------------------------------MGDTITLLSRREIEKMRQAGQLAAA
AMP2_SYNY3       ------------------MNHQNLLSITRNLVHPPISSGLVLLSARELDKMRRVGQLAAN
AMPM_ECOLI       -------------------------------------MAISIKTPEDIEKMRVAGRLAAE
AMPM_HAEIN       -------------------------------------MAIPIRTEKEIVKLREACKLASD
AMP3_SYNY3       PAWPRFLGTHPMNLLSQLFAPPSPVPSPTPKAKKRSRRGVQIKTPAEIAIMRQAGAIAAQ
AMPM_BACSU       --------------------------------------MIICKTPRELGIMREAGRIVAL
AMP2_MOUSE       CDLYPNGVFPKGQECEYPPTQDGRTAAWRTTSEEKKALDQASE--EIWNDFREAAEAHRQ
AMP2_RAT         CDLYPNGVFPKGQECEYPPTQDGRTAAWRTTSEEKKALDQASE--EIWNDFREAAEAHRQ
AMP2_HUMAN       CDLYPNGVFPKGQECEYPPTQDGRTAAWRTTSEEKKALDQASE--EIWNDFREAAEAHRQ
AMP2_YEAST       ELLFPDGKYPEGAWMDY--HQDFN--LQRTTDEESRYLKRDLERAEHWNDVRKGAEIHRR
AMPM_METJA       ------------------------------------------MEIEGYEKIIEAGKIASK
AMPM_SULSO       ------------------------------------------MTEDELNKLLLAGKIAAK
AMPM_METFE       -----------------------------------------------MEKFKKAGKIASK
AMPM_HELPY       -------------------------------------MAISIKSPKEIKALRKAGELTAQ
```

*Figure 2Bb - Multiple sequence alignment and Clustal display of methionine aminopeptidases*

```
MAP-3_insertion     -------------MTTEEIDALVHREIISHN-----AYPSPLGYG--GFP---KSVCTSVN
MAP-3_f1            VLLLAGKSLKVDMTTEEIDALVHREIISHN-----AYPSPLGYG--GFP---KSVCTSVN
AMP1_HUMAN          VLDVAAGMIKPGVTTEEIDHAVHLACIARN-----CYPSPLNYY--NFP---KSCCTSVN
AMP1_YEAST          VLDIAAAHVRPGITTDELDEIVHNETIKRG-----AYPSPLNYY--NFP---KSLCTSVN
AMP1_SYNY3          LLDHLAPMVQPGITTLELNDEAEKWTKAHG-----AISAPLGYN--GFP---KSICTSIN
AMP2_SYNY3          LLNHLESMVQPGVSTQALNDEATRWMEDHG-----AISATLGYAPPGYPPFTGAICTSIN
AMPM_ECOLI          VLEMIEPYVKPGVSTGELDRICNDYIVNEQH----AVSACLGYH--GYP---KSVCISIN
AMPM_HAEIN          VLVMIEPYVKAGVTTCELDRICHEYMVNEQK----VIPACLNYH--GFP---KATCISIN
AMP3_SYNY3          VLKEIAATVQPGMTTGDLDQLAEERIRSLG-----ATPSFKGYH--GFP---ASICACVN
AMPM_BACSU          THEELKKHIKPGISTKELDQIAERFIKKQG-----AIPSFKGYN--GFR---GSICVSVN
AMP2_MOUSE          VRKYVMSWIKPGMTMIEICEKLEDCSRK-------LIKENGLNAGLAFP-----TGCSLN
AMP2_RAT            VRKYVMSWIKPGMTMIEICEKLEDCSRK-------LIKENGLNAGLAFP-----TGCSLN
AMP2_HUMAN          VRKYVMSWIKPGMTMIEICEKLEDCSRK-------LIKENGLNAGLAFP-----TGCSLN
AMP2_YEAST          VRRAIKDRIVPGMKLMDIADMIENTTRKYTGAENLLAMEDPKSQGIGFP-----TGLSLN
AMPM_METJA          VREEAVKLIXPGVKLLEVAEFVENRIRE-------------LGGEPAFP-----CNISIN
AMPM_SULSO          ARDEVSLDVKASAKVLDICEEVESIIIE-------------NKAFPSFP-----CNISIN
AMPM_METFE          VRKKAIKAVKGEMKILDLAEFIENEIEK-------------MGAKPAFP-----CNISVN
AMPM_HELPY          ALALLEREVRPGVSLLELDKMAEDFIKSSH-----ARPAFKGLY--GFP---NSVCMSLN
                                  .   :                                :       .*

MAP-3_insertion     NVLCHGIPD-SR--PLQDGDIINIDVTVYYNGYHGDTSETFLVGN-----ED-----ECG
MAP-3_f1            NVLCHGIPD-SR--PLQDGDIINIDVTVYYNGYHGDTSETFLVGN----VD-----ECG
AMP1_HUMAN          EVICHGIPD-RR--PLQEGDIVNVDITLYRNGYHGDLNETFFVGE----VD-----DGA
AMP1_YEAST          EVICHGVPD-KT--VLKEGDIVNLDVSLYYQGYHADLNETYYVGEN----IS----KEA
AMP1_SYNY3          EVICHGIPHRKR--VLQAGDIINVDVTPIVDGYHGDCSRTFFVGT-----PS----PVA
AMP2_SYNY3          EVVCHGIPNPKQ--ILKDGDIINIDVTLRLAGYHGDTSRTFLVGS-----VS-----ATA
AMPM_ECOLI          EVVCHGIPDDAK--LLKDGDIVNIDVTVIKDGFHGDTSKMFIVGKP----T------IMG
AMPM_HAEIN          EVVCHGIPSDDK--VLKNGDIVNIDVTVIKDGYFGDNSKMYIVGGE---TN-----IRS
AMP3_SYNY3          NEVVHGIPRRRK--KIRSGDLLKVDTGAYFQGYHGDSCITIAVGK-----VS-----PQA
AMPM_BACSU          EELVHGIPGSR---VLKDGDIISIDIGAKLNGYHGDSAWTYPVGN-----IS-----DDD
AMP2_MOUSE          NCAAHYTPNAGDTTVLQYDDICKIDFGTHISGRIIDCAFTVTFN-----PKY--------
AMP2_RAT            NCAAHYTPNAGDTTVLQYDDICKIDFGTHISGRIIDCAFTVTFN-----PKY--------
AMP2_HUMAN          NCAAHYTPNAGDTTVLQYDDICKIDFGTHISGRIIDCAFTVTFN-----PKY--------
AMP2_YEAST          HCAAHFTPNAGDKTVLKYEDVMKVDYGVQVNGNIIDSAFTVSFD-----PQY--------
AMPM_METJA          EIAAHYTPKLNDNLEFKDDDVVKLDLGAHVDGYIADTAITVDLS-----NSY--------
AMPM_SULSO          SEAAHYSPTINDEKRIPEGAVVKLDLGAHIDGFISDTAITISLD-----SRY--------
AMPM_METFE          EITAHYSPPCNDDRKILPGDLVKIDIGVHVDGFIGDTATTVLVEGYEDLKNYNDELAEKN
AMPM_HELPY          EVVIHGIPTDY---VLQEGDIIGLDLGVEVDGYYGDSALTLPIGA-----IS-----PQD
                       *  *         :    .  :*       *    *         .

MAP-3_insertion     KKLVEVARRCRDEAIAACRAGAPFSVIGNTISHITH--------QNGFQVCPHFVGHGI
MAP-3_f1            KKLVEVARRCRDEAIAACRAGAPFSVIGNTISHITH--------QNGFQVCPHFVGHGI
AMP1_HUMAN          RKLVQTTYECLMQAIDAVKPGVRYRELGNIIQKHAQ---------ANGFSVVRSYCGHGI
AMP1_YEAST          LNTTETSRECLKLAIKMCKPGTTFQELGDHIEKHAT--------ENKCSVVRTYCGHGV
AMP1_SYNY3          EKLVKVTEECLRLGIEAVKPGGKIGDIGAAIQSHAE---------AQGFSVVRDFVGHGI
AMP2_SYNY3          RKLVEATQESMMRGIAEIKPGARIGDIGAAIQAYAE---------ASGFSVVRDMVGHGI
AMPM_ECOLI          ERLCRITQESLYLALRMVKPGINLREIGAAIQKFVE---------AEGFSVVREYCGHGI
AMPM_HAEIN          KKLVEAAQEALYVGIRTVKPDIRLNEIGKAVQKYTE-------SQTFSVVREYCGHGV
AMP3_SYNY3          QRLMEVAEGALYAGIEQVKPGNYLMDIAGAIEDYVK---------PTGYTIVEEFTGHGV
AMPM_BACSU          KKLLEVTEESLYKGLQEAKPGERLSNISHAIQTYVE------NEQFSVVREYVGHGV
AMP2_MOUSE          DILLTAVKDATNTGIKCAGIDVRLCDVGEAIQEVMESYEVEIDGKTYQVKPIRNLNGHSI
AMP2_RAT            DILLKAVKDATNTGIKCAGIDVRLCDVGEAIQEVMESYEVEIDGKTYQVKPIRNLNGHSI
AMP2_HUMAN          DTLLKAVKDATNTGIKCAGIDVRLCDVGEAIQEVMESYEVEIDGKTYQVKPIRNLNGHSI
AMP2_YEAST          DNLLAAVKDATYTGIKEAGIDVRLTDIGEAIQEVMESYEVEINGETYQVKPCRNLCGHSI
AMPM_METJA          KDLVKASEDALYTVIKEINPPMNIGEMGKIIQEVIE---------SYGYKPISNLSGHVM
AMPM_SULSO          QRLLDASKTALEAAITNFKAGLSIGEIGRVIEKVIR---------AQGYKPIRNLGGHLI
AMPM_METFE          KKMIEAAESALENAINTIRDGVEIGKIGEVIENTIN---------KFGFKPISNLTGHTI
AMPM_HELPY          EKLLACSKESLMHAINSIRVGMHFKELSQILESTIT---------ERGFVPLKGFCGHGI
                               .    :                :.   :.                  **
```

*Figure 2Bc - Multiple sequence alignment and Clustal display of methionine aminopeptidases*

```
MAP-3_insertion     G-SYFHGHPEIWHHAND-S----DLPMEEGMAFTIEPIITEGSPEFKVLEDAWTVVSLDN
MAP-3_f1            G-SYFHGHPEIWHHAND-S----DLPMEEGMAFTIEPIITEGSPEFKVLEDAWTVVSLDN
AMP1_HUMAN          H-KLFHTAPNVPHYAKNKA----VGVMKSGHVFTIEPMICEGGWQDETWPDGWTAVTRDG
AMP1_YEAST          G-EFFHCSPNIPHYAKNRT----PGVMKPGMVFTIEPMINEGTWKDMTWPDDWTSTTQDG
AMP1_SYNY3          S-KIFHTAPQIPHYGKAGK----GKRLRPGMVFTIEPMINEGTWEAVLLDDGWTAITKDG
AMP2_SYNY3          G-RQMHTELQIPHYGKRGS----GLKLRPGMVFTVEPMLNEGTYELTFLADGWTVITKDK
AMPM_ECOLI          G-RGFHEEPQVLHYDSRET----NVVLKPGMTFTIEPMVNAGKKEIRTMKDGWTVKTKDR
AMPM_HAEIN          G-TEFHCEPQVLHYYADDG----GVILKPGMVFTIEPMINAGKKEVRVMGDGWTVKTKDR
AMP3_SYNY3          G-QALHEDPHVFNVRCRDLP---NVKLKPGMTLAIEPIVNAGSRFTRTLGDRWIVVTVDN
AMPM_BACSU          G-QDLHEDPQIPHYGPPNK----GPRLKPGMVLAIEPMVNAGSRYVKTLADNWTVVTVDG
AMP2_MOUSE          GPYRIHAGKTVPIVKGGEA-----TRMEEGEVYAIETFGSTGKGVVHDDMECSHYMKNFD
AMP2_RAT            GPYRIHAGKTVPIVKGGEA-----TRMEEGEVYAIETFGSTGKGVVHDDMECSHYMKNFD
AMP2_HUMAN          GQYRIHAGKTVPIVKGGEA-----TRMEEGEVYAIETFGSTGKGVVHDDMECSHYMKNFD
AMP2_YEAST          APYRIHGGKSVPIVKNGDT-----TKMEEGEHFAIETFGSTGRGYVTAGGEVSHYARSAE
AMPM_METJA          HRYELHTGISIPNVYERTN-----QYIDVGDLVAIEPFATDGFGMVKDGNLGNIYKFLAK
AMPM_SULSO          RRYELHAGVFIPNVYERGL-----GVIQSDSVYAIEPFATDGGGEVVEGKSITIYS--LK
AMPM_METFE          DRWVLHSGLSIPNVKGQNS----HKL----------------------------------
AMPM_HELPY          G-KKPHEEPEIPNYLEKGVKPNSGPKIKEGMVFCLEPMVCQKQGEPKILADKWSVVSVDG
                            *      :                  .

MAP-3_insertion     QR---SAQFEHTVLITSRGAQILTKLPHEA------------------------------
MAP-3_f1            QR-----SAQFEHTVLITSRGAQILTKLPHEA----------------------------
AMP1_HUMAN          KR-----SAQFEHTLLVTDTGCEILTRRLDSARPHFMSQF--------------------
AMP1_YEAST          KL-----SAQFEHTLLVTEHGVEILTARNKKS-PGGPRQRIK------------------
AMP1_SYNY3          KL-----SAQFEHTIAVTEDGVEILTLGE-------------------------------
AMP2_SYNY3          KL-----SAQFEHTVVVTEEGVEILTLA--------------------------------
AMPM_ECOLI          SL-----SAQYEHTIVVTDNGCEILTLRKDDTIPAIISHDE-------------------
AMPM_HAEIN          SH-----SAQYEHQLIVTETGCEVMTIRDEEIAEGRISRIMVNV----------------
AMP3_SYNY3          AL-----SAQFEHTVLVTATGYELLTDRRLV-----------------------------
AMPM_BACSU          KK-----CAHFEHTIAITETGFDILTRV--------------------------------
AMP2_MOUSE          VGHVPIRLPRTKHLLNVINENFGTLAFCRRWLDRLGE--SKYLMALKNLCDLGIVDPYPP
AMP2_RAT            VGHVPIRLPRTKHLLNVINENFGTLAFCRRWLDRLGE--SKYLMALKNLCDLGIVDPYPP
AMP2_HUMAN          VGHVPIRLPRTKHLLNVINENFGTLAFCRRWLDRLGE--SKYLMALKNLCDLGIVDPYPP
AMP2_YEAST          DHQVMPTLDSAKNLLKTIDRNFGTLPFCRRYLDRLGQ- EKYLFALNNLVRHGLVQDYPP
AMPM_METJA          RP-IRLPQAR--KLLDVISKNYPYLPFAERWVLKNES---ERLALNSLIRASCIYGYPI
AMPM_SULSO          NPNIKGLSSRENELIDFIYTRFNYLPFSERWLKEFSTNVDELRNNIKNLVKKGALRGYPI
AMPM_METFE          ------------------------------------------------------------0
AMPM_HELPY          LN-----TSHHEHTIAIVGNKAVILTER--------------------------------

MAP-3_insertion     -------------------------------- (SEQ ID NO: 6)
MAP-3_f1            -------------------------------- (SEQ ID NO: 8)
AMP1_HUMAN          -------------------------------- (SEQ ID NO: 2)
AMP1_YEAST          -------------------------------- (SEQ ID NO: 9)
AMP1_SYNY3          -------------------------------- (SEQ ID NO: 10)
AMP2_SYNY3          -------------------------------- (SEQ ID NO: 11)
AMPM_ECOLI          -------------------------------- (SEQ ID NO: 12)
AMPM_HAEIN          -------------------------------- (SEQ ID NO: 13)
AMP3_SYNY3          -------------------------------- (SEQ ID NO: 14)
AMPM_BACSU          -------------------------------- (SEQ ID NO: 15)
AMP2_MOUSE          LCDIKGSYTAQFEHTILLRPTCKEVVSRGDDY (SEQ ID NO: 16)
AMP2_RAT            LCDIKGSYTAQFEHTILLRPTCKEVVSRGDDY (SEQ ID NO: 17)
AMP2_HUMAN          LCDIKGSYTAQFEHTILLRPTCKEVVSRGDDY (SEQ ID NO: 4)
AMP2_YEAST          LNDIPGSYTAQFEHTILLHAHKKEVVSKGDDY (SEQ ID NO: 18)
AMPM_METJA          LKERENGIVGQAEHTILITENGVEITTK---- (SEQ ID NO: 20)
AMPM_SULSO          LIEIKKGVVSQFEHTVIVKGDSIIVSTKSL-- (SEQ ID NO: 21)
AMPM_METFE          -------------------------------- (SEQ ID NO: 19)
AMPM_HELPY          -------------------------------- (SEQ ID NO: 22)
```

*Figure 3a - Alignment of SEQ ID NO: 5 vs. SEQ ID NO: 7*

```
                   ....|....| ....|....| ....|....| ....|....| ....|....|
                           10         20         30         40         50
                   EcoRI
SEQ ID 24         ctagaattcATG GCGGCGCCCA GTGGCGTC
SEQ ID 5           CGCCAACATG GCGGCGCCCA GTGGCGTCCA CCTGCTCGTC CGCAGAGGTA
SEQ ID 7           ---------- GCGGCGCC-A GTGGCGTCCA CCTGCTCGTC CGCAG-----
SEQ ID 8        1  .......Met AlaAlaProS erGlyValHi sLeuLeuVal ArgAr

                   ....|....| ....|....| ....|....| ....|....| ....|....|
                           60         70         80         90        100
SEQ ID 5           AGCGCGTGGA CGAGAGCCCC GTGAGGGTTC GCACGGTTGC TCACTAGGTT
SEQ ID 7           ---------- ---------- ---------- ---------- -----AGGTT
SEQ ID 8                                                         gGlyS    15

                   ....|....| ....|....| ....|....| ....|....| ....|....|
                          110        120        130        140        150
SEQ ID 5           CTCATAGAAT TTTCTCTTCA CCACTCAATC ATATCTACTT ACACAAGCAG
SEQ ID 7           CTCATAGAAT TTTCTCTTCA CCACTCAATC ATATCTACTT ACACAAGCAG
SEQ ID 8       16  erHisArgIl ePheSerSer ProLeuAsnH isIleTyrLe uHisLysGln  31

                   ....|....| ....|....| ....|....| ....|....| ....|....|
                          160        170        180        190        200
SEQ ID 5           TCAAGCAGTC AACAAAGAAG AAATTTCTTT TTTCGCAGAC AAAGAGATAT
SEQ ID 7           TCAAGCAGTC AACAAAGAAG AAATTTCTTT TTTCGGAGAC AAAGAGATAT
SEQ ID 8           (omitted for clarity)

                   ....|....| ....|....| ....|....| ....|....| ....|....|
                          210        220        230        240        250
SEQ ID 5           TTCACACAGT ATAGTTTTGC CGGCTGCAGT TTCTTCAGCT CATCCGGTTC
SEQ ID 7           TTCACACAGT ATAGTTTTGC CGGCTGCAGT TTCTTCAGCT CATCCGGTTC

                   ....|....| ....|....| ....|....| ....|....| ....|....|
                          260        270        280        290        300
SEQ ID 5           CTAAGCACAT AAAGAAGCCA GACTATGTGA CGACAGGCAT TGTACCAGAC
SEQ ID 7           CTAAGCACAT AAAGAAGCCA GACTATGTGA CGACAGGCAT TGTACCAGAC

                   ....|....| ....|....| ....|....| ....|....| ....|....|
                          310        320        330        340        350
SEQ ID 5           TGGGGAGACA GCATAGAAGT TAAGAATGAA GATCAGATTC AAGGGCTTCA
SEQ ID 7           TGGGGAGACA GCATAGAAGT TAAGAATGAA GATCAGATTC AAGGGCTTCA

                   ....|....| ....|....| ....|....| ....|....| ....|....|
                          360        370        380        390        400
SEQ ID 5           TCAGGCTTGT CAGCTGGCCC GCCACGTCCT CCTCTTGGCT GGGAAGAGTT
SEQ ID 7           TCAGGCTTGT CAGCTGGCCC GCCACGTCCT CCTCTTGGCT GGGAAGAGTT

                   ....|....| ....|....| ....|....| ....|....| ....|....|
                          410        420        430        440        450
SEQ ID 5           TAAAGGTTGA CATGACAACT GAAGAGATAG ATGCTCTTGT TCATCGGGAA
SEQ ID 7           TAAAGGTTGA CATGACAACT GAAGAGATAG ATGCTCTTGT TCATCGGGAA

                   ....|....| ....|....| ....|....| ....|....| ....|....|
                          460        470        480        490        500
SEQ ID 5           ATCATCAGTC ATAATGCCTA TCCCTCACCT CTAGGCTATG GAGGTTTTCC
SEQ ID 7           ATCATCAGTC ATAATGCCTA TCCCTCACCT CTAGGCTATG GAGGTTTTCC

                   ....|....| ....|....| ....|....| ....|....| ....|....|
                          510        520        530        540        550
SEQ ID 5           AAAATCTGTT TGTACCTCTG TAAACAACGT GCTCTGTCAT GGTATTCCTG
SEQ ID 7           AAAATCTGTT TGTACCTCTG TAAACAACGT GCTCTGTCAT GGTATTCCTG

                   ....|....| ....|....| ....|....| ....|....| ....|....|
                          560        570        580        590        600
SEQ ID 5           ACAGTCGACC TCTTCAGGAT GGAGATATTA TCAACATTGA TGTCACAGTC
SEQ ID 7           ACAGTCGACC TCTTCAGGAT GGAGATATTA TCAACATTGA TGTCACAGTC
```

*Figure 3b - Alignment of SEQ ID NO: 5 vs. SEQ ID NO: 7*

```
                  ....|....| ....|....| ....|....| ....|....| ....|....|
                        610        620        630        640        650
SEQ ID 5          TATTACAATG GCTACCATGG AGACACCTCT GAAACATTTT TGGTGGGCAA
SEQ ID 7          TATTACAATG GCTACCATGG AGACACCTCT GAAACATTTT TGGTGGGCAA

                  ....|....| ....|....| ....|....| ....|....| ....|....|
                        660        670        680        690        700
SEQ ID 5          TGTGGACGAA TGTGGTAAAA AGTTAGTGGA GGTTGCCAGG AGGTGTAGAG
SEQ ID 7          TGTGGACGAA TGTGGTAAAA AGTTAGTGGA GGTTGCCAGG AGGTGTAGAG

                  ....|....| ....|....| ....|....| ....|....| ....|....|
                        710        720        730        740        750
SEQ ID 5          ATGAAGCAAT TGCAGCTTGC AGAGCAGGGG CTCCCTTCTC TGTAATTGGA
SEQ ID 7          ATGAAGCAAT TGCAGCTTGC AGAGCAGGGG CTCCCTTCTC TGTAATTGGA

                  ....|....| ....|....| ....|....| ....|....| ....|....|
                        760        770        780        790        800
SEQ ID 5          AACACAATCA GCCACATAAC TCATCAGAAT GGTTTTCAAG TCTGTCCACA
SEQ ID 7          AACACAATCA GCCACATAAC TCATCAGAAT GGTTTTCAAG TCTGTCCACA

                  ....|....| ....|....| ....|....| ....|....| ....|....|
                        810        820        830        840        850
SEQ ID 5          TTTTGTGGGA CATGGAATAG GATCTTACTT TCATGGACAT CCAGAAATTT
SEQ ID 7          TTTTGTGGGA CATGGAATAG GATCTTACTT TCATGGACAT CCAGAAATTT

                  ....|....| ....|....| ....|....| ....|....| ....|....|
                        860        870        880        890        900
SEQ ID 5          GGCATCATGC AAACGACAGT GATCTACCCA TGGAGGAGGG CATGGCATTC
SEQ ID 7          GGCATCATGC AAACGACAGT GATCTACCCA TGGAGGAGGG CATGGCATTC

                  ....|....| ....|....| ....|....| ....|....| ....|....|
                        910        920        930        940        950
SEQ ID 5          ACTATAGAGC CAATCATCAC GGAGGGATCC CCTGAATTTA AAGTCCTGGA
SEQ ID 7          ACTATAGAGC CAATCATCAC GGAGGGATCC CCTGAATTTA AAGTCCTGGA

                  ....|....| ....|....| ....|....| ....|....| ....|....|
                        960        970        980        990       1000
SEQ ID 5          GGATGCATGG ACTGTGGTCT CCCTAGACAA TCAAAGGTCG GCGCAGTTCG
SEQ ID 7          GGATGCATGG ACTGTGGTCT CCCTAGACAA TCAAAGGTCG GCGCAGTTCG

                  ....|....| ....|....| ....|....| ....|....| ....|....|
                       1010       1020       1030       1040       1050
SEQ ID 5          AGCACACGGT TCTGATCACG TCGAGGGGCG CGCAGATCCT GACCAAACTA
SEQ ID 7          AGCACACGGT TCTGATCACG TCGAGGGGCG CGCAGATCCT GACCAAACTA
SEQ ID 25                                                        CTA
(rev cmp)
                  ....|....| ....|....| ....|....| ....|....| ....|....|
                       1060       1070       1080       1090       1100
SEQ ID 5          CCCCATGAGG CCTGAGGAGC CGCCCGAAGG TCGCGGTGAC CTGGTGCCTT
SEQ ID 7          CCCCATGAGG CCTGAGGAGC CGCCCGAAGG TCGCGGTGAC CTGGTGCCTT
SEQ ID 25         CCCCATGAGG CCTGAgcggccgca
(rev cmp)                StuI ***  NotI
SEQ ID 8          ProHisGluA laEnd
```

*Figure 3c - Alignment of SEQ ID NO: 5 vs. SEQ ID NO: 7*

```
              ....|....| ....|....| ....|....| ....|....| ....|....|
                    1110       1120       1130       1140       1150
SEQ ID 5      TTTAAATAAA TTGCTGAAAT TTGGCTGGAG AACTTTTAGA AGAAACAGGG
SEQ ID 7      TTTAAATAAA TTGCTGAAAT TTGGCTGGAG AACTTTTAGA AGAAACAGGG

              ....|....| ....|....| ....|....| ....|....| ....|....|
                    1160       1170       1180       1190       1200
SEQ ID 5      AAATGACCGG TGGTGCGGTA ACCTGCGTGG CTCCTGATAG CGTTTGGAAG
SEQ ID 7      AAATGACCGG TGGTGCGGTA ACCTGCGTGG CTCCTGATAG CGTTTGGAAG

              ....|....| ....|....| ....|....| ....|....| ....|....|
                    1210       1220       1230       1240       1250
SEQ ID 5      AACGCGGGGG AGACTGAAGA ACAACTGGGA ACTCGGATCT GAAGCCCTGC
SEQ ID 7      AACGCGGGGG AGACTGAAGA CCAACTGGGA ACTCGGATCT GAAGCCCTGC

              ....|....| ....|....| ....|....| ....|....| ....|....|
                    1260       1270       1280       1290       1300
SEQ ID 5      TGGGGTCGCG CGGCTTTCGA AAAACAAATC CTGGCCCTGG ACTCGGTTTC
SEQ ID 7      TGGGGTCGCG CGGCTTTGGA AAAACAAATC CTGGCCCTGC ACTCGGTTTC

              ....|....| ....|....| ....|....| ....|....| ....|....|
                    1310       1320       1330       1340       1350
SEQ ID 5      CCAACGCGGT CAACGCATCT GGAGGGGACT GGAGGAAACC CCCTTGTTGG
SEQ ID 7      CCAGCGCGGT CAACGCATGT GGAGGGGACT GGAGGAAACC CCCTTGTTGG

              ....|....| ....|....| ....|....| ....|....| ....|....|
                    1360       1370       1380       1390       1400
SEQ ID 5      AAGAGATTCC AAGAGAAGCA CGG-TTTCTC TTT CCTTG- CCTGACTGTT
SEQ ID 7      AAGAGATTCC AAGAGAAGCA CGGKTTTCTC TTTCCCNTGC CCTGACTGTT

              ....|....| ....|....| ....|....| ....|....| ....|....|
                    1410       1420       1430       1440       1450
SEQ ID 5      GGAGTAAAAA ACCTCTTAAA TCCATTGTAT CA-GAGGTCC TTACCTCTCT
SEQ ID 7      GGAGTAAAAA ACCTCTTAAA TCCATTGTAT CAAGAGGTCC TTACCTCTCT

              ....|....| ....|....| ....|....| ....|....| ....|....|
                    1460       1470       1480       1490       1500
SEQ ID 5      GACAGTTACA -TGATCTTTG TATCTGAACT TTGCACGTCT GCCGAAAAAT
SEQ ID 7      GACAGTTACA ATGATCTTTG TATCTGAACT TTGCACGTCT GCCGAAAAAT

              ....|....| ....|....| ....|....| ....|....| ....|....|
                    1510       1520       1530       1540       1550
SEQ ID 5      CCGAACCTGT TGACTGGGAT TTTTAAGAAT CCGTTTCTCC CTTTTGTGTA
SEQ ID 7      CCGAACCTGT TGACTGGCAA AAAAAAAAAA AAACMMAAAA AAAAAAAAAA

              ....|....| ....|....| ....|....| ....|....| ....|....|
                    1560       1570       1580       1590       1600
SEQ ID 5      TTCCATATTG GCCGGCCCCA AGGATGCTCG CAGAAGCCAG CCCCCAACCC
SEQ ID 7      AAAAAAAAAA AAAAAAAAAA AAAAAAAAAR GGGCGGCCGC ----------

              ....|....| ....|....| ....|....| ....|....| ....|....|
                    1610       1620       1630       1640       1650
SEQ ID 5      CAGCCCTTCC GTATCTTTCC CCTCCATCGC GGCTTTGCGA TGAAAGATTA
SEQ ID 7      ---------- ---------- ---------- ---------- ----------

              ....|....| ....|....| ....|....| ....|....| ....|....|
                    1660       1670       1680       1690       1700
SEQ ID 5      GCCCGCGAAC AGAGGCATTG ATTACAAACA TGTCCTTGGC AGTGGACTCT
SEQ ID 7      ---------- ---------- ---------- ---------- ----------

              ....|....| ....|....| ....|....| ....|....| ....|....|
                    1710       1720       1730       1740       1750
SEQ ID 5      GGGCCTGGCC ATTCTTCAGG TTTCTCTCAA TCCAGAAACG CGACTTTCCT
SEQ ID 7      ---------- ---------- ---------- ---------- ----------
```

*Figure 3d - Alignment of SEQ ID NO: 5 vs. SEQ ID NO: 7*

```
               ....|....| ....|....| ....|....| ....|....| ....|....|
                    1760       1770       1780       1790       1800
SEQ ID 5       GGACCCCTGC GGCTCTTC-T NCCCCGCCAC ATTCAGCCTT CAAGGCCAGT
SEQ ID 7       ---------- ---------- ---------- ---------- ----------

               ....|....| ....|....| ....|....| ....|....| ....|....|
                    1810       1820       1830       1840       1850
SEQ ID 5       CCAGANGTGA AGTTTGAGGC CCTCCCCCCA CCCACCCCAC ACGCACGCAC
SEQ ID 7       ---------- ---------- ---------- ---------- ----------

               ....|....| ....|....| ....|....| ....|....| ....|....|
                    1860       1870       1880       1890       1900
SEQ ID 5       GCACGCTAGA GCGTTTGCTG CACTAGGAAT TCGAGCTTGG GCCCCACTCG
SEQ ID 7       ---------- ---------- ---------- ---------- ----------

               ....|....| ....|....| ....|....| ....|....| ....|....|
                    1910       1920       1930       1940       1950
SEQ ID 5       CCCAGGTGTG AACAGTGGCT GATTAGTGGG CGGTCTAGTC TCTAAAATGA
SEQ ID 7       ---------- ---------- ---------- ---------- ----------

               ....|....| ....|....| ....|....| ....|....| ....|....|
                    1960       1970       1980       1990       2000
SEQ ID 5       CCCCTCCCCA GACTGGCCCT TCTCGCATCG GCACCCGCGC TTGCACGCTG
SEQ ID 7       ---------- ---------- ---------- ---------- ----------

               ....|....| ....|....| ....|....| ....|....| ....|....|
                    2010       2020       2030       2040       2050
SEQ ID 5       CAGGAGCCGC AAACGTCAGC TGTTCTGGAA ACCGAGAGGG TCCCAGAGAG
SEQ ID 7       ---------- ---------- ---------- ---------- ----------

               ....|....| ....|....| ....|....| ....|....| ....|....|
                    2060       2070       2080       2090       2100
SEQ ID 5       AGGAGATACG GGCGCATTTG AGAGCAAGGG CCTACTTGGC CGGCACTGAA
SEQ ID 7       ---------- ---------- ---------- ---------- ----------

               ....|....| ....|....| ....|....| ....|....| ....|....|
                    2110       2120       2130       2140       2150
SEQ ID 5       GCTTGCGAGT TGAGCTCCAG TTCGGCCGGC AGTTCCATCC CGCTTCAGGA
SEQ ID 7       ---------- ---------- ---------- ---------- ----------

               ....|....| ....|....| ....|....| ....|....| ....|....|
                    2160       2170       2180       2190       2200
SEQ ID 5       ACAGGAATCC AAGGGCCCAC GCTCTGTCTG CAAGGGCCAT TCCTGCCCGG
SEQ ID 7       ---------- ---------- ---------- ---------- ----------

               ....|....| ....|....| ....|....| ....|....| ....|....|
                    2210       2220       2230       2240       2250
SEQ ID 5       AGCACCCTCC TTTCCCTTGC GCTTGCTCTC CGGTACCTGT TCCGCACCTG
SEQ ID 7       ---------- ---------- ---------- ---------- ----------

               ....|....| ....|....| ....|....| ....|....| ....|....|
                    2260       2270       2280       2290       2300
SEQ ID 5       AGCTCAAGGC AGGGAGAGGC CGGGCCTCTG GCAGTCCACG AAGGAAGCCG
SEQ ID 7       ---------- ---------- ---------- ---------- ----------

               ....|....| ....|....| ....|....| ....|....| ....|....|
                    2310       2320       2330       2340       2350
SEQ ID 5       TCTGCCTTCG GTTATGATTT TAGGAACAAG TCCAACGAGG GTGTTCAAGC
SEQ ID 7       ---------- ---------- ---------- ---------- ----------

               ....|....| ....|....| ....|....| ....|....| ....|....|
                    2360       2370       2380       2390       2400
SEQ ID 5       AGTTAATGGT TGTGCTAACT CTTGTTTCTA CTGAAGCGGG TTTTGCAAAG
SEQ ID 7       ---------- ---------- ---------- ---------- ----------
```

*Figure 3e - Alignment of SEQ ID NO: 5 vs. SEQ ID NO: 7*

```
                ....|....| ....|....| ....|....| ....|....| ....|....|
                    2410       2420       2430       2440       2450
SEQ ID 5        CTGACATCCC TTAAAGATAA CTTGGGCTTT CGGAAGCGGC AAGGAAATGG
SEQ ID 7        ---------- ---------- ---------- ---------- ----------

                ....|....| ....|....| ....|....| ....|....| ....|....|
                    2460       2470       2480       2490       2500
SEQ ID 5        CACCCGTAGT TCCCAGGACA GGTGGTGTCC TCGGCCAGGA CTAAGAGCCA
SEQ ID 7        ---------- ---------- ---------- ---------- ----------

                ....|....| ....|....| ....|....| ....|....| ....|....|
                    2510       2520       2530       2540       2550
SEQ ID 5        GCTCATCTTT GTAACATTCA TAATACGGGA AACTGAGGAC CAGGTGGCTC
SEQ ID 7        ---------- ---------- ---------- ---------- ----------

                ....|....| ....|....| ....|....| ....|....| ....|....|
                    2560       2570       2580       2590       2600
SEQ ID 5        GGAAAAGAGA TGAGTTCCAC CTTTTACCTA ACACAGGGTT CTCTCGTCGT
SEQ ID 7        ---------- ---------- ---------- ---------- ----------

                ....|....| ....|....| ....|....| ....|....| ....|....|
                    2610       2620       2630       2640       2650
SEQ ID 5        CCCCCAACCC CTCCAGCTCG GCTTCTTTGT GTCCAGGGTT GTAGATTTTT
SEQ ID 7        ---------- ---------- ---------- ---------- ----------

                ....|....| ....|....| ....|....| ....|....| ....|....|
                    2660       2670       2680       2690       2700
SEQ ID 5        GGATAGAGGT GTTTCTGATT CTAGTGAGTC TGAGAACTGG AAAAGACCAA
SEQ ID 7        ---------- ---------- ---------- ---------- ----------

                ....|....| ....|....| ....|....| ....|....| ....|....|
                    2710       2720       2730       2740       2750
SEQ ID 5        GGAGGGGTTG ATGATTTMCA AGGTCCATAG AAAAACTTTT TGTGTGGTCG
SEQ ID 7        ---------- ---------- ---------- ---------- ----------

                ....|....| ....|....| ....|....| ....|....| ....|....|
                    2760       2770       2780       2790       2800
SEQ ID 5        GAAGTTGGCC AAGCAGAGGC CCACAGCCTG ATGCTACTCC CCCCCACCCC
SEQ ID 7        ---------- ---------- ---------- ---------- ----------

                ....|....| ....|....| ....|....| ....|....| ....|....|
                    2810       2820       2830       2840       2850
SEQ ID 5        CCCAAAGATC TGAATTCCTA AAGATCAAGA GGGTTCAGCT GGCCTTGGGA
SEQ ID 7        ---------- ---------- ---------- ---------- ----------

                ....|....| ....|....| ....|....| ....|....| ....|....|
                    2860       2870       2880       2890       2900
SEQ ID 5        GATGTTTGCT GGAGAATCAC TTCAGTTTTC TCCTAAGGCA ATCAGATTGC
SEQ ID 7        ---------- ---------- ---------- ---------- ----------

                ....|....| ....|....| ....|....| ....|....| ....|....|
                    2910       2920       2930       2940       2950
SEQ ID 5        ANCCATTAGC ATTGTATNTT ATCTGCAAAT CAGTTTACTC CGAGGTTCCC
SEQ ID 7        ---------- ---------- ---------- ---------- ----------

                ....|....| ....|....| ....|....| ....|....| ....|....|
                    2960       2970       2980       2990       3000
SEQ ID 5        CAAGGATAGT TTTATTAGGA CCACAGGNCT TTNCTAACCN CTGAGGTAAC
SEQ ID 7        ---------- ---------- ---------- ---------- ----------

                ....|....| ....|....| ....|....| ....|....| ....|....|
                    3010       3020       3030       3040       3050
SEQ ID 5        NCGCTGCTTG TGCANCAATT ATTTTGAGGT GGAGGTATTT ATGGGNCAAG
SEQ ID 7        ---------- ---------- ---------- ---------- ----------

                ....|....| ....|....| ....|....| ....|....| ....|....|
                    3060       3070       3080       3090       3100
SEQ ID 5        TTTATAATTC CATTTATTAA AGGGACTANC CTAAAAAAAA AAAAAAAAAA
SEQ ID 7        ---------- ---------- ---------- ---------- ----------

                ....|....| ....|....| ....|.
                    3110       3120
SEQ ID 5        AAAAAAAAAA GGGCGGCCGC ------
SEQ ID 7        ---------- ---------- --....
```

*Figure 4A - Nucleotide sequence of a PCR fragment encoding human MetAP-3*

```
     EcoRI
ctagaattc atg gcg gcg ccc agt ggc gtc cac ctg ctc gtc cgc aga ggt  51
          Met Ala Ala Pro Ser Gly Val His Leu Leu Val Arg Arg Gly
           1               5                   10

tct cat aga att ttc tct tca cca ctc aat cat atc tac tta cac aag   99
Ser His Arg Ile Phe Ser Ser Pro Leu Asn His Ile Tyr Leu His Lys
 15                 20                  25                  30

cag tca agc agt caa caa aga aga aat ttc ttt ttt cgg aga caa aga  147
Gln Ser Ser Ser Gln Gln Arg Arg Asn Phe Phe Phe Arg Arg Gln Arg
                 35                  40                  45

gat att tca cac agt ata gtt ttg ccg gct gca gtt tct tca gct cat  195
Asp Ile Ser His Ser Ile Val Leu Pro Ala Ala Val Ser Ser Ala His
             50                  55                  60

ccg gtt cct aag cac ata aag aag cca gac tat gtg acg aca ggc att  243
Pro Val Pro Lys His Ile Lys Lys Pro Asp Tyr Val Thr Thr Gly Ile
         65                  70                  75

gta cca gac tgg gga gac agc ata gaa gtt aag aat gaa gat cag att  291
Val Pro Asp Trp Gly Asp Ser Ile Glu Val Lys Asn Glu Asp Gln Ile
     80                  85                  90

caa ggg ctt cat cag gct tgt cag ctg gcc cgc cac gtc ctc ctc ttg  339
Gln Gly Leu His Gln Ala Cys Gln Leu Ala Arg His Val Leu Leu Leu
 95                 100                 105                 110

gct ggg aag agt tta aag gtt gac atg aca act gaa gag ata gat gct  387
Ala Gly Lys Ser Leu Lys Val Asp Met Thr Thr Glu Glu Ile Asp Ala
                115                 120                 125

ctt gtt cat cgg gaa atc atc agt cat aat gcc tat ccc tca cct cta  435
Leu Val His Arg Glu Ile Ile Ser His Asn Ala Tyr Pro Ser Pro Leu
            130                 135                 140

ggc tat gga ggt ttt cca aaa tct gtt tgt acc tct gta aac aac gtg  483
Gly Tyr Gly Gly Phe Pro Lys Ser Val Cys Thr Ser Val Asn Asn Val
        145                 150                 155

ctc tgt cat ggt att cct gac agt cga cct ctt cag gat gga gat att  531
Leu Cys His Gly Ile Pro Asp Ser Arg Pro Leu Gln Asp Gly Asp Ile
    160                 165                 170

atc aac att gat gtc aca gtc tat tac aat ggc tac cat gga gac acc  579
Ile Asn Ile Asp Val Thr Val Tyr Tyr Asn Gly Tyr His Gly Asp Thr
175                 180                 185                 190

tct gaa aca ttt ttg gtg ggc aat gtg gac gaa tgt ggt aaa aag tta  627
Ser Glu Thr Phe Leu Val Gly Asn Val Asp Glu Cys Gly Lys Lys Leu
                195                 200                 205

gtg gag gtt gcc agg agg tgt aga gat gaa gca att gca gct tgc aga  675
Val Glu Val Ala Arg Arg Cys Arg Asp Glu Ala Ile Ala Ala Cys Arg
            210                 215                 220

gca ggg gct ccc ttc tct gta att gga aac aca atc agc cac ata act  723
Ala Gly Ala Pro Phe Ser Val Ile Gly Asn Thr Ile Ser His Ile Thr
        225                 230                 235

cat cag aat ggt ttt caa gtc tgt cca cat ttt gtg gga cat gga ata  771
His Gln Asn Gly Phe Gln Val Cys Pro His Phe Val Gly His Gly Ile
    240                 245                 250

gga tct tac ttt cat gga cat cca gaa att tgg cat cat gca aac gac  819
Gly Ser Tyr Phe His Gly His Pro Glu Ile Trp His His Ala Asn Asp
255                 260                 265                 270

agt gat cta ccc atg gag gag ggc atg gca ttc act ata gag cca atc  867
Ser Asp Leu Pro Met Glu Glu Gly Met Ala Phe Thr Ile Glu Pro Ile
                275                 280                 285

atc acg gag gga tcc cct gaa ttt aaa gtc ctg gag gat gca tgg act  915
```

*Figure 4 B*

```
Ile Thr Glu Gly Ser Pro Glu Phe Lys Val Leu Glu Asp Ala Trp Thr
            290                 295                 300

gtg gtc tcc cta gac aat caa agg tcg gcg cag ttc gag cac acg gtt      963
Val Val Ser Leu Asp Asn Gln Arg Ser Ala Gln Phe Glu His Thr Val
        305                 310                 315

ctg atc acg tcg agg ggc gcg cag atc ctg acc aaa cta ccc cat gag     1011
Leu Ile Thr Ser Arg Gly Ala Gln Ile Leu Thr Lys Leu Pro His Glu
    320                 325                 330

StuI       NotI
gcc tga gcggccgca (SEQ ID NO: 69)                                   1026
Ala  *            (SEQ ID NO:  8)
335
```

*Figure 5 - Alignment of human methionine aminopeptidases 1, 2, and 3 (SEQ ID NOS: 2, 4, 8)*

```
MetAP1     1 -------------MAAVETRVCETDGCSSEAKLQCPTCIKLGIQG---SYFCSQECFKGS
MetAP3     1 --------------------------------MAAPSGVHLLVR-------RGSHRIFSS
MetAP2     1 MAGVEEVAASGSHLNGDLDPDDREEGAASTAEEAAKKKRRKKKKSKGPSAAGEQEPDKES

MetAP-1   45 WATHKLLHKKAKDEKAKREVSSWTVE-GDINTDPWAGYRYTGKLRPHYPLMPTRPVPSYI
MetAP-3   22 PLNHIYLHKQSSSQ--QRRNFFFRRQ-RDISHSIVLPAAVS----------SAHPVPKHI
MetAP-2   61 GASVDEVARQLERSALEDKERDEDDEDGDGDGDGATGKKKKKKKKKRGP--KVQTDPPSV

MetAP-1  104 QRPDYADHPLGMSESEQALKGTS---------------QIKLLSSEDIEGMRLVCRLARE
MetAP-3   69 KKPDYVTTGIVPDWG---DS-------------------IEVKNEDQIQGLHQACQLARH
MetAP-2  119 PICDLYPNGVFPKGQECEYPPTQDGRTAAWRTTSEEKKALDQASEEIWNDFREAAEAHRQ

MetAP-1  149 VLDVAAGMIKPGVTTEEIDHAVHLACIARNCYPSPLNYYNFPKSCCTSVNEVICHGIP--
MetAP-3  107 VLLLAGKSLKVDMTTEEIDALVHREIISHNAYPSPLGYGGFPKSVCTSVNNVLCHGIP--
MetAP-2  179 VRKYVMSWIKPGMTMIEICEKLEDCSRKLIKENGLNAGLAFPTGCS--LNNCAAHYTPNA

MetAP-1  207 -DRRPLQEGDIVNVDITLYRNGYHGDLNETFFVG----EVDDGARKLVQTTYECLMQAID
MetAP-3  165 -DSRPLQDGDIINIDVTVYYNGYHGDTSETFLVG----NVDECGKKLVEVARRCRDEAIA
MetAP-2  237 GDTTVLQYDDICKIDFGTHISGRIIDCAFTVTFNPKYDTLLKAVKDATNTGIKCAGIDVR
                           *          *

MetAP-1  262 AVKPGVRYRELGNIIQKHAQANGFSVVRS--YCGHGIHKLFHTAPNVPHYAKNKAVGVMK
MetAP-3  220 ACRAGAPFSVIGNTISHITHQNGFQVCPH--FVGHGIGSYFHGHPEIWHHAN-DSDLPME
MetAP-2  297 LCDVGEAIQEVMESYEVEIDGKTYQVKPIRNLNGHSIGQYRIHAGKTVPIVKGGEATRME
                                              *

MetAP-1  320 SGHVFTIEPMICEGG---------------------------------------------
MetAP-3  277 EGMAFTIEPIITEGS---------------------------------------------
MetAP-2  357 EGEVYAIETFGSTGKGVVHDDMECSHYMKNFDVGHVPIRLPRTKHLLNVINENFGTLAFC
                     *

MetAP-1  335 --WQDETWPDGWTAVTR-----------------DGKRSAQFEHTLLVTDTGCEILTRRL
MetAP-3  292 --PEFKVLEDAWTVVSL-----------------DNQRSAQFEHTVLITSRGAQILTKLP
MetAP-2  417 RRWLDRLGESKYLMALKNLCDLGIVDPYPPLCDIKGSYTAQFEHTILLRPTCKEVVSRGD

MetAP 1  376 DSARPHFMSQF (SEQ ID NO: 2)
MetAP 3  333 HEA-------- (SEQ ID NO: 8)
MetAP-2  477 DY--------- (SEQ ID NO: 4)
```

*Figure 6AB - Expression analysis of MetAP-3 in normal human tissues*
A
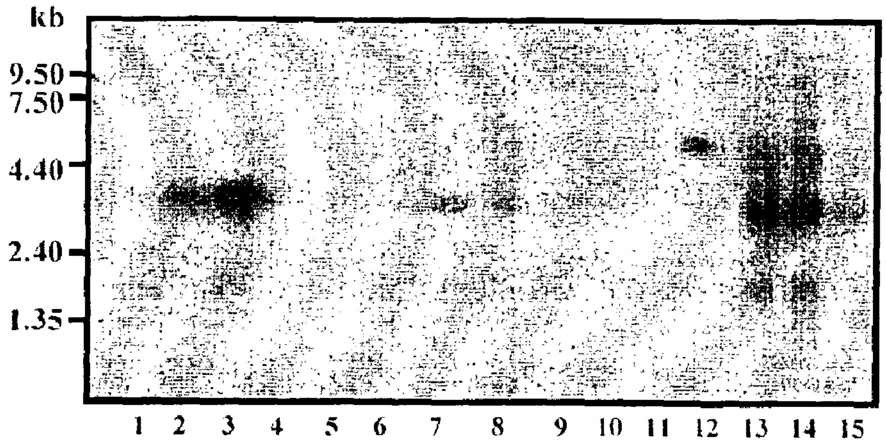
B
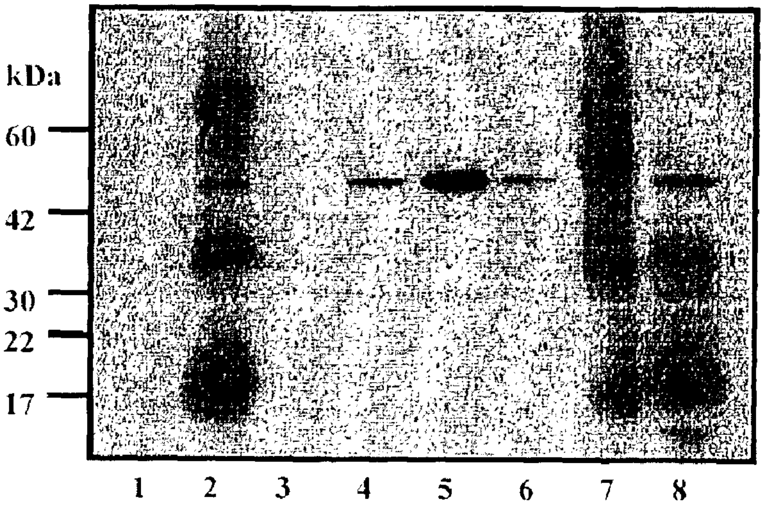

*Figure 7AB - Expression and purification of human MetAP-3 and subcellular localization of human MetAP-3 in normal mouse liver*
A
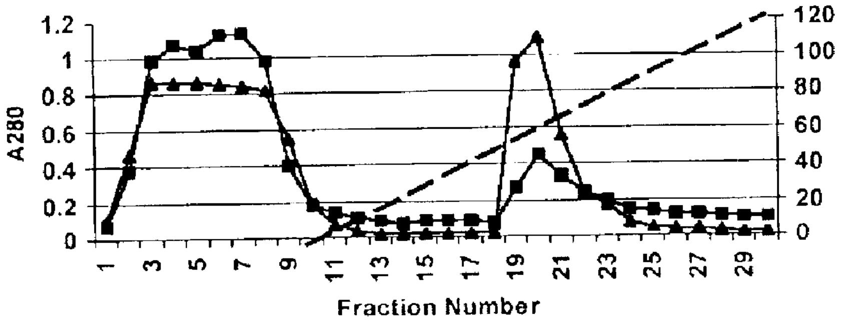
B
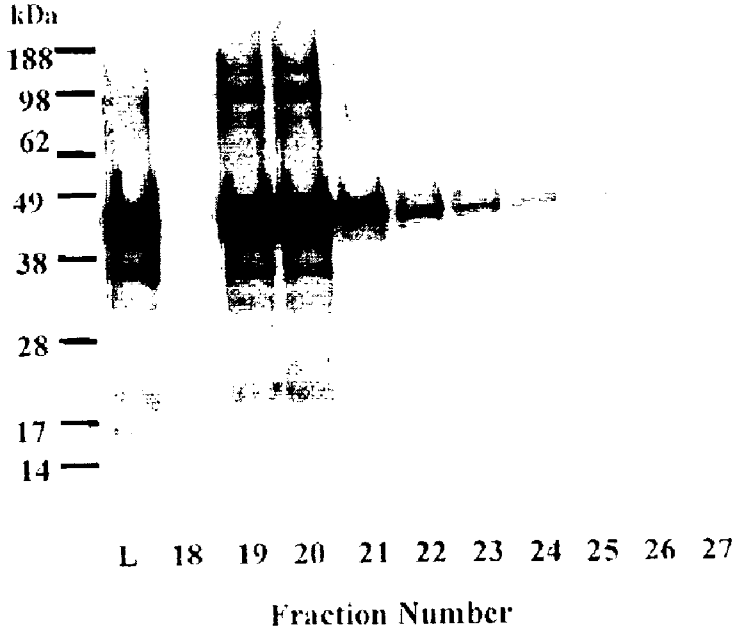

*Figure 8A - Subcellular localization of MetAP-3 in normal mouse liver*
A
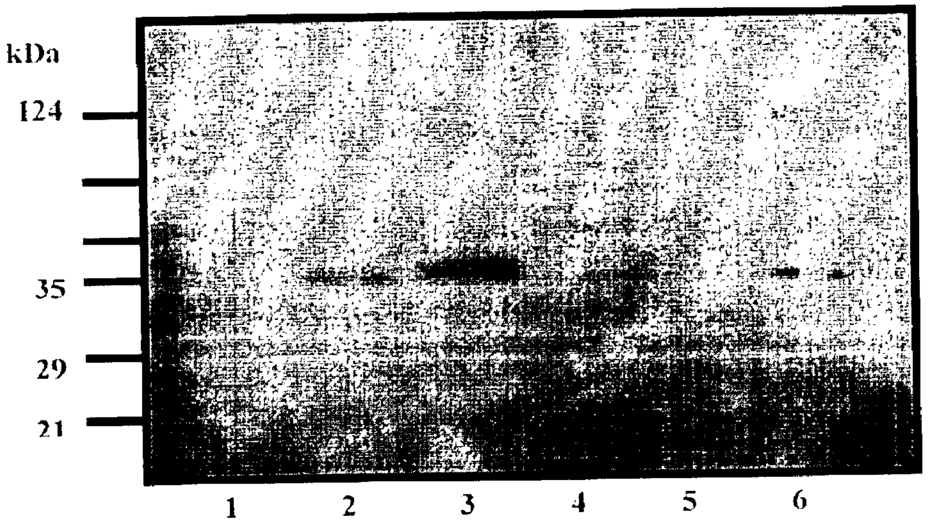

HUMAN METHIONINE AMINOPEPTIDASE TYPE 3

PRIORITY

The present application is a continuation-in-part of U.S. application Ser. No. 09/523,263, filed Mar. 10, 2000, now U.S. Pat. No. 6,638,750, which claims priority under Title 35, United States Code §119, to U.S. Provisional Application Ser. No. 60/125,139, filed Mar. 11, 1999.

FIELD OF THE INVENTION

Methionine aminopeptidases catalyse the co-translational removal of amino terminal methionine residues from nascent polypeptide chains. A newly-discovered enzyme, designated methionine aminopeptidase type-3 (MetAP-3), has a substrate specificity which is similar to MetAP-1 and MetAP-2, although it is not inhibited by fumagillin, an irreversible inhibitor of MetAP-2. MetAP-3 also preferentially localizes to mitochondria, unlike MetAP-1 and MetAP-2, which accumulate in the cytoplasm. One embodiment of the present invention relates to human cDNAs encoding polypeptides comprising MetAP-3. Other embodiments of the invention relate to nucleic acid molecules derived from these cDNAs, including complements, homologues, and fragments thereof, and methods of using these nucleic acid molecules, to generate polypeptides and fragments thereof. Other embodiments of the invention relate to antibodies directed against polypeptides comprising MetAP-3, and methods to screen for compounds or compositions that preferentially or specifically effect the activity of polypeptides comprising MetAP-3.

BACKGROUND

Angiogenesis

Angiogenesis, the process of new blood vessel formation, is essential for the exponential growth of solid tumors and tumor metastasis. Radiological and cytocidal treatments, combined with regimens involving selective inhibitors of angiogenesis should lead to dramatic reductions in tumor growth. One well-known angiogenesis inhibitor was first discovered as fungal contaminant in bovine endothelial cell cultures that inhibited cell proliferation (Ingber et al. *Nature* 348:555–557, 1990). The responsible organism was subsequently identified as *A. fumagatus*, and the product identified as fumagillin, a widely recognized amebicide and antibiotic (McCowen et al., *Science* 113:202–203 (1951)). Fumagillin was found to be a potent inhibitor of endothelial cell proliferation, but its therapeutic window was insufficient for further clinical advancement. TNP-470, a fumagillin-like derivative with 50-fold higher potency, was subsequently developed from a directed chemical approach (Ingber et al., *Nature* 348:555–557 (1990), Kusaka et al., *Biochem. Biophys. Res. Commun.* 174:1070–1076 (1991)). This compound's therapeutic use is limited, however, by its lack of oral availability and dose-limiting neurotoxicity.

Until recently, the molecular target for fumagillin or TNP-470 was unknown. In 1997, the target protein was isolated, purified, and identified by mass spectrometry as the type-2 methionine aminopeptidase (MetAP-2). Fumagillin, and its analogs TNP-470 and ovalicin, are now known to irreversibly bind and potently inhibit MetAP-2, but not the type-1 enzyme (Griffith, E. C., Su, Z., Turk, B. E., Chen, S., Chang, Y-.H., Wu, Z., Biemann, K., and Liu, J. O. (1997) Chem. Biol. 4, 461–471; Sin, N., Meng, L., Wang, M. Q. W., Wen, J. J., Bornmann, W. G., and Crews, C. M. (1997) Proc. Natl. Acad. Sci. USA 94, 6099–6103). Together, these results identified MetAP-2 as a target for the development of anti-angiogenesis agents.

TNP-470 is currently being studied in clinical trials as a therapy to treat cancer. TNP-470 has been shown to mediate its effects in animal models by inhibiting new blood vessel formation at the site of tumor growth (Kruger E. A., and Figg W. D. (2000) Expert Opin. Investig. Drugs 9, 1383–96). How this class of compounds suppresses de novo angiogenesis through inhibition of MetAP-2 remains unclear. Although MetAP-2 has been shown to be a target of these suicide inhibitors, other methionine aminopeptidase enzyme homologs may exist that could contribute to the efficacy or neurological side effects observed in the preclinical animal models and the clinical trials for TNP-470 (Castronovo, V., and Belotti, D. (1996) Eur. J. Cancer 32, 2520–2527).

Methionine Aminopeptidases

Most proteins are encoded by messenger RNAs that dictate that the amino terminus of a nascent polypeptide chain is methionine. More than 60% of all cytosolic proteins lose this initiator methionine, however, in a co-translational excision process catalyzed by methionine aminopeptidase enzymes (Arfin, S. M., Kendall, R. L., Hall, L., Weaver, L. H., Stewart, A. E., Matthews, B. W., and Bradshaw, R. A. (1995) Proc. Natl. Acad. Sci. USA 92, 7714–7718). Methionine aminopeptidases were first isolated from eubacteria and shown to be cobalt-containing enzymes with molecular masses of about 30 kDa (Ben-Bassat et al., J. Bacteriol. 169:751–757 (1987), Suh et al., Gene 169:17–23 (1996), and Miller et al., Proc. Natl. Acad. Sci. (U.S.A.) 91:2473–2477, 1987). Their structures include a novel protease fold, with pseudosymmetry around a pair of cobalt ions (Roderick and Matthews, Biochemistry 32:3907–3912, 1993).

Enzymes with the same substrate specificity, but with larger molecular masses, were isolated from yeast and pig. Highly homologous regions at the C-terminal domain (~30 kDa) of the eukaryotic and the prokaryotic forms were discovered, although the N-terminal domain of the eukaryotic enzymes was found to be unique (Kendall and Bradshaw, *J. Biol. Chem.* 267:20667–20673 (1992)). The N-terminal domain of the yeast enzyme contained sequences consistent with two zinc-finger structures, indicating a potential site of nucleic acid interaction. This class of enzyme was designated methionine aminopeptidase type I (MetAP-1). The porcine enzyme lacked the zinc-binding domains, but contained a block of polylysine and aspartic residues within the N-terminal domain, and was described as Type II (MetAP-2). Both isozymes have been found from Archebacteria to man, indicating a critical metabolic function (Arfin et al. *Proc. Natl. Acad. Sci.* (*U.S.A.*) 92:7714–7718 (1995), Bradshaw et al., *TIBS* 23: 263–267 (1998)).

The single prokaryotic and two eukaryotic methionine aminopeptidases that have been characterized extensively demonstrate a substrate preference for proteins that contain a small or uncharged amino acid (Ala, Cys, Gly, Pro, Ser, Thr, or Val) at the second position next to the initiator methionine. In prokaryotes the initiator methionine is formylated while still bound to the initiator tRNA. Removal of the formyl group from $tRNA^{fMet}$ by a peptide deformylase is an absolute prerequisite for methionine removal by MetAPs (Solbiati, J., Chapman-Smith, A., Miller, J. L., Miller, C. G., Cronan, J. E. (1999) J. Mol. Biol. 290, 607–614).

The biological consequence of amino terminal methionine removal is poorly understood, due in part to the essential nature of this process, as revealed by the lethality of bacterial and yeast MetAP deletion mutants (Chang, S. Y., McGary, E. C., and Chang, S. (1989) J. Bacteriol. 171, 4071–4072; Li, X and Chang Y.-H. (1995) Proc. Natl. Acad. Sci. USA 92, 12357–12361). The absolute requirement for methionine removal could be for any of a variety of reasons, including 1) exposure of a glycine residue for myristoylation, 2) destabilization of a protein by targeting its degradation and/or 3) optimal protein function due to stabilization by amino terminal acetylation.

Methionine aminopeptidase-2 is bi-functional. One action is the removal of the N-terminal methionine residues from their protein substrates. MetAP-2 can also bind to and prevent phosphorylation of the α-subunit of the peptide change initiation factor eIF-2 by one or more eIF-2 kinases (Datta et al., *Proc. Natl. Acad. Sci. USA* 85: 3324–2238 1(1988), Wu et al., *J. Biol. Chem.* 268:10796–10781 (1993)). This action promotes protein synthesis within the cell. The eIF-2 phosphorylation inhibitory activity of MetAP-2 is unaffected by TNP-470 binding, indicating that the loss of aminopeptidase activity is involved in the anti-angiogenic activity of TNP-470 (Griffith et al., *Chem. Biol.* 4:461–471 (1997)). The function of methionine aminopeptidase activity in endothelial cell proliferation during tumorigenesis is unclear, although inhibition of MetAP-2 may play a role in altering the stability of one or more protein(s) whose abnormal presence or absence results in endothelial cell dysregulation. Several signaling proteins also appear to be modified by the covalent attachment of myristic acid to a glycine residue which occurs only after the initial amino-terminal methionine removal by MetAP-2 (Peseckis et al., *J. Biol. Chem.* 267:5107–5114 (1993)). Inhibition of methionine aminopeptidase activity may prevent this covalent attachment, resulting in improper functioning of a signal component specific to endothelial cell cycle regulation (Sin et al. *Proc. Natl. Acad. Sci.* (*U.S.A.*) 94:6099–6103 (1997)).

The Use of Methionine Aminopeptidases and Inhibitors of Methionine Aminopeptidases N-terminal processing agents, such as the methionine aminopeptidases, also function to initiate post-translational peptide or protein modifications which may control or induce activation, translocation, or protein turnover (Bradshaw et al., *TIBS* 23: 263–267 (1998)). Because this initial processing is important for normal protein functioning, it is possible that alteration of methionine aminopeptidase activity is a factor in a variety of diseases, including angiogenesis. Therapies could then be developed which can modify methionine aminopeptidase activity to restore proper protein processing.

Methionine aminopeptidase activity can also be used to modify recombinant proteins expressed and harvested from *E. coli* or other expression systems. Recombinant proteins that retain the N-terminal methionine, in some cases, have biological characteristics that differ from the native species that retain the N-terminal methionine, including the induction of undesireable antibodies. Methionine aminopeptidases could lower the cost of manufacturing processes designed produce recombinant proteins that mimic the structure of native species which are used to treat or reduce the symptoms of various diseases (Sandman et al., *Biotechnology* 13:504–6 (1995)).

Clearly, an understanding of methionine aminopeptidase activity and its role in various tissues can provide useful therapeutic and diagnostic insight into angiogenesis and tumor metastasis. The known MetAP-2 inhibitors are not good candidates for clinical use as angiogenesis inhibitors due to their neurotoxic effects. Differential expression of mammalian MetAP-1, MetAP-2, or other unidentified methionine aminopeptidases may partially or totally account for the observed variation in sensitivity of different cell types to inhibition by TNP-470 and other MetAP-2 inhibitors, and thus account for the toxicity of these compounds.

SUMMARY OF THE INVENTION

A cDNA encoding a new human methionine aminopeptidase (MetAP-3) was cloned and characterized. Peptides to the predicted amino acid sequence were used to raise MetAP-3-specific antibodies. Immunoblotting experiments demonstrated that MetAP-3 is highly enriched within mitochondria. MetAP-3 was shown to be an active aminopeptidase not inhibited by fumagillin, a potent irreversible inhibitor of MetAP-2. These results, taken together, suggest that fumagillin and its clinical analogs do not exert their anti-angiogenic effects through a MetAP-3-dependent biological response.

One embodiment of the present invention relates to a purified and isolated polypeptide selected from the group consisting of: (a) methionine aminopeptidase type 3 (MetAP-3); (b) a polypeptide comprising MetAP-3; (c) a polypeptide having the amino acid sequence of SEQ ID NO 8; and (d) a polypeptide comprising the amino acids set forth in SEQ ID NO 8.

Other embodiments of the present invention relate to recombinant polypeptides comprising MetAP-3, isolated and purified antibodies having a binding specificity for polypeptides comprising MetAP-3, compositions comprising said antibodies, methods for detecting polypeptides comprising MetAP-3 in a biological fluid, nucleic acids encoding polypeptides comprising MetAP-3, vectors comprising said nucleic acids, host cells comprising said vectors; methods of expressing recombinant polypeptides comprising MetAP-3; compositions comprising said polypeptides; methods for determining levels of nucleic acids in a cell encoding MetAP-3 related polypeptides; and methods for using MetAP-3-related polypeptides to remove methionine from the amino terminus of a polypeptide and recovering the polypeptide.

BRIEF DESCRIPTION OF THE DRAWINGS

FIG. 1 displays phylogenetic trees showing the genetic relatedness of various methionine aminopeptidases Panel 1A shows the phylogenetic relationship, displayed as a tree diagram, between the amino acid sequences of various methionine aminopeptidases, including MetAP types 1, 2, and 3, and the relationship between full-length human MetAP-3 and mouse MetAP-3. Panel 1B shows a tree diagram without the mouse MetAP-3 sequence. Panel 1C show a similar tree diagram as Panel 1B, including the partial amino acid sequence encoded by the clone designated MAP-3 insertion (see text for details).

FIG. 2 shows multiple amino acid sequence alignments of various methionine aminopeptidases Panels 2Aa, 2Ab, and 2Ac show multiple amino acid sequence alignments and boxshade displays of various methionine aminopeptidases MetAP-Type 1, 2, and 3 and the close relationship between mouse and human MetAP-3 (MAP3).

| | |
|---|---|
| human MAP3 insertion | SEQ ID NO: 6 |
| human MAP3 full length | SEQ ID NO: 8 |
| mouse MAP3 | SEQ ID NO: 68 |
| AMPM_ECOLI | SEQ ID NO: 12 |
| AMPM_HAEN | SEQ ID NO: 13 |
| AMP1_HUMAN | SEQ ID NO: 2 |
| AMP1 YEAST | SEQ ID NO: 9 |
| AMP1 SYNY3 | SEQ ID NO: 10 |
| AMP2 SYNY3 | SEQ ID NO: 11 |
| AMP3 SYNY3 | SEQ ID NO: 14 |
| AMPM BACSU | SEQ ID NO: 15 |
| AMP2 MOUSE | SEQ ID NO: 16 |
| AMP2 RAT | SEQ ID NO: 17 |
| AMP2 HUMAN | SEQ ID NO: 4 |
| AMP2 YEAST | SEQ ID NO: 18 |
| AMPM METJA | SEQ ID NO: 20 |
| AMPM SULSO | SEQ ID NO: 21 |
| AMPM METFE | SEQ ID NO: 19 |
| AMPM HELPY | SEQ ID NO: 22 |

Panels 2Ba, 2Bb, and 2Bc show a similar Clustal multiple sequence alignment and display, including the partial amino acid sequence encoded by the clone designated MAP-3 insertion (see text for details).

FIG. 3 shows a sequence alignment between SEQ ID NO: 5 and SEQ ID NO: 7

A pairwise alignment was performed between SEQ ID NO: 5 and SEQ ID NO: 7 to show the position of the 50 base pair insert present in SEQ ID NO: 5. The ATG start codon and TGA stop codons are highlighted in bold. The positions of two PCR primers, SEQ ID NO: 24, and the reverse complement of SEQ ID NO: 25 used to amplify the 5' and 3' ends of the human MetAP-3 gene, respectively are also shown. Nucleotides in lower case indicate sequences outside the coding sequence. Underlined sequences show the recognition sites for EcoRI, StuI and NotI restriction enzymes. A portion of the amino terminal and carboxy terminal sequences of SEQ ID NO: 8 are also shown (with the intervening sequences omitted for clarity).

FIG. 4 shows the nucleotide and amino acid sequence of human methionine aminopeptidase-3

FIG. 4 shows the nucleotide sequence of a PCR fragment encoding human MetAP-3. The MetAP-3 coding region consists of 1,008 nucleotides. The protein initiation and stop codons are in bold. Nucleotides in lower case indicate sequences outside the coding sequence. Underlined sequences show the recognition sites for EcoRI, StuI and NotI restriction enzymes.

FIG. 5 shows a shows the protein sequence alignment of known human methionine aminopeptidases and the deduced amino acid sequence of hMetAP-3

Panel 5A shows the protein sequence alignment of known human methionine aminopeptidases and the deduced amino acid sequence of hMetAP-3. Identical amino acids have a black background and conservative changes are in a gray background. Four sets of amino acids, highlighted by an asterisk (*), are known to be critical for cobalt coordination in human MetAP-1 and MetAP-2.

FIG. 6 shows the expression analysis of MetAP-3 in normal human tissues

Panel 6A shows an RNA blotting (Northern) analysis using the complete coding region of human MetAP-3 cDNA as a probe against a multiple tissue blot. Each lane contains 2 μg PolyA$^+$ RNA from the following human tissues: lane 1, brain; 2, heart; 3, skeletal muscle; 4, colon; 5, thymus; 6, spleen; 7, kidney; 8, liver; 9, small intestine; 10, placenta; 11, lung; 12, peripheral blood leukocytes; 13, prostate; 14, testis; and 15, uterus. A prominent MetAP-3 messenger RNA band corresponded to a 3.62 kb size. Panel 6B, shows an immunoblotting (Western) analysis using a MetAP-3 specific peptide polyclonal antibody to evaluate the expression of MetAP-3 protein in various human tissues. Each lane contains 75 μg of total protein from the following tissues: lane 1, liver; 2, lung; 3, brain; 4, kidney; 5, testis; 6, ovary; 7, heart; and 8, spleen. Molecular weight size markers are indicated on the left. The MetAP-3 protein migrates with an apparent molecular weight of 43 kDa. The immunoreactivity detected at 17 kDa, 35 kDa, and 70 kDa found in lung, heart, and spleen total protein extracts was determined to be nonspecific proteins. Molecular weight size markers are indicated on the left.

FIG. 7 shows the expression and purification of recombinant human MetAP-3

Recombinant human MetAP-3 was expressed in *E. coli* as a N-terminal NusA-6×His tagged fusion protein and purified by sequential column purification using Q Sepharose HP, Sephacyl S-100HR, and a final Mono S column. The NusA fusion protein and 6×His tag were removed by thrombin cleavage prior to the Mono S column. Panel 7A, The absorbance (squares) and enzyme activity (triangles) were monitored from fractions eluted from the Mono S column using a 0–1 M NaCl gradient (diagonal line). Panel 7B, MetAP-3 Western analysis from the Mono S column fractions. The recombinant hMetAP-3 migrates with an apparent molecular weight of 45 kDa. Molecular weight size markers are indicated on the left.

FIG. 8 shows the sub-cellular localization of MetAP-3 in normal mouse liver

Panel 8A shows the distribution of MetAP-3 in various tissues by a sub-cellular fraction-specific Western blot. Each lane contains 50 μg of total protein from the following sub-cellular factions of normal mouse liver: lane 1, total liver protein; 2, nuclei; 3, mitochondria; 4, Golgi; 5, smooth endoplasmic reticulum; and 6, rough endoplasmic reticulum. The MetAP-3 protein migrates with an apparent molecular weight of 45 kDa. Molecular weight size markers are indicated on the left.

TERMS AND DEFINITIONS

The following is a list of abbreviations and the corresponding meanings as used interchangeably herein:

bp=base pair(s)

CDK=cyclin dependent kinase

HEPES=N-2-hydroxyethylpiperazine-N'-2-ethanesulfonic acid hMetAP, huMetAP, HMAP, or hMAP=human methionine aminopeptidase IPTG=isopropylthio-β-galactoside kb=kilobase(s)

kDa=kilodaltons

KLH=keyhole limpet hemacyanin

Mb=megabase(s)

MetAP or MAP=methionine aminopeptidase

MetAP-3, MetAP3, or MAP3=methionine aminopeptidase type 3 mg=milligram(s)

ml or mL=milliliter(s)

Ni-NTA=nickel-nitrilotriacetic acid

ODNs=oligonucleotides

PAGE=polyacrylamide gel electrophoresis

PCR=polymerase chain reaction

PMSF=phenylmethylsulfonyl fluoride

RP-HPLC=reverse phase high performance liquid chromatography

SDS=sodium dodecyl sulfate

SSC=saturated sodium chloride ug or μg=microgram(s)

ul or μl=microliter(s)

The following is a list definitions of various terms used herein:

The term "altered" means that expression differs from the expression response of cells or tissues not exhibiting the phenotype.

The term "amino acid(s)" means all naturally occurring L-amino acids, including norleucine, norvaline, homocysteine, and ornithine.

The term "chromosome walking" means a process of extending a genetic map by successive hybridization steps.

The term "complete complementarity" means that every nucleotide of one molecule is complementary to a nucleotide of another molecule.

The term "degenerate" means that two nucleic acid molecules encode for the same amino acid sequences but comprise different nucleotide sequences.

The term "exogenous genetic material" means any genetic material, whether naturally occurring or otherwise, from any source that is capable of being inserted into any organism.

The term "expression response" means a mutation affecting the level or pattern of the expression encoded in part or whole by one or more nucleic acid molecules.

The term "fragment" means a nucleic acid molecule whose sequence is shorter than the target or identified nucleic acid molecule and having the identical, the substantial complement, or the substantial homologue of at least 10 contiguous nucleotides of the target or identified nucleic acid molecule.

The term "fusion molecule" means a protein-encoding molecule or fragment thereof that upon expression, produces a fusion protein.

The term "fusion protein" means a protein or fragment thereof that comprises one or more additional peptide regions not derived from that protein.

The term "marker nucleic acid" means a nucleic acid molecule that is utilized to determine an attribute or feature (e.g., presence or absence, location, correlation, etc.) of a molecule, cell, or tissue.

A "MetAP-3 fragment" means a peptide or polypeptide whose amino acid sequence comprises a subset of the amino acid sequence of MetAP-3 protein.

The term "mimetic" refers to a compound having similar functional and/or structural properties to another known compound or a particular fragment of that known compound.

The term "phenotype" means any of one or more characteristics of an organism, tissue, or cell.

The term "probe" means an agent that is utilized to determine an attribute or feature (e.g. presence or absence, location, correlation, etc.) of a molecule, cell, tissue, or organism.

The term "promoter" is used in an expansive sense to refer to the regulatory sequence(s) that control mRNA production.

The term "protein fragment" means a peptide or polypeptide molecule whose amino acid sequence comprises a subset of the amino acid sequence of that protein.

The term "protein molecule/peptide molecule" means any molecule that comprises five or more amino acids.

The term "recombinant" means any agent (e.g., DNA, peptide, etc.), that is, or results from, however indirectly, human manipulation of a nucleic acid molecule.

The term "selectable or screenable marker genes" means genes whose expression can be detected by a probe as a means of identifying or selecting for transformed cells.

The term "specifically bind" means that the binding of an antibody or peptide is not competitively inhibited by the presence of non-related molecules.

The term "specifically hybridizing" means that two nucleic acid molecules are capable of forming an anti-parallel, double-stranded nucleic acid structure.

The term "substantial complement" means that a nucleic acid sequence shares at least 80% sequence identity with the complement.

The term "substantial fragment" means a nucleic acid fragment which comprises at least 100 nucleotides.

The term "substantial homologue" means that a nucleic acid molecule shares at least 80% sequence identity with another.

The term "substantially hybridizing" means that two nucleic acid molecules can form an anti-parallel, double-stranded nucleic acid structure under conditions (e.g. salt and temperature) that permit hybridization of sequences that exhibit 90% sequence identity or greater with each other and exhibit this identity for at least about a contiguous 50 nucleotides of the nucleic acid molecules.

The term "substantially-purified" means that one or more molecules that are or may be present in a naturally-occurring preparation containing the target molecule will have been removed or reduced in concentration.

DETAILED DESCRIPTION OF THE INVENTION

These detailed descriptions are presented for illustrative purposes only and are not intended to be, and should not be taken as, a restriction to the scope of the invention or the claims that follow. Rather, they are merely some of the embodiments that one skilled in the art would understand from the entire contents of this disclosure.

Overview

The present invention is directed, in part, to the isolation of a nucleic acid encoding a MetAP-3 protein, which exhibits sequence homology to the highly conserved residues that coordinate the cobalt ions in MetAP-1 and MetAP-2. The phylogenetic relationship between various methionine aminopeptidases is shown in FIG. 1, Panels A, B, and C. MetAP-3 and MetAP-1/MetAP-2 exhibit different expression profiles, suggesting additional or different roles for MetAP-3 in cellular metabolism and in an organism as a whole. The present invention, comprising novel MetAP-3 nucleic acids, proteins, peptides, homologues, and fragments of either, provides new and advantageous targets to screen for diagnostic and therapeutic agents and compositions useful for diagnosis or treatment of angiogenesis-related diseases. Such diseases include but are not limited to angiogenesis associated with tumor growth and tumor metastasis, neovascularization induced by retinopathy, or hypoxia resulting from ischemic injury.

As the new protein exhibits a similar primary sequence to MetAP-1 and MetAP-2, it is referred to herein as "MetAP-3." SEQ ID NO: 8 sets forth the amino acid sequence of human MetAP-3. FIG. 2, Panels A and B shows a comparison between the amino acid sequences of various MetAP-1, MetAP-2, and MetAP-3 polypeptides. FIG. 3 shows a pair-wise comparison between the nucleotide sequence of two clones, SEQ ID NO: 5 and SEQ ID NO: 7, encoding MetAP-3. FIG. 4 shows the amino acid translation of the nucleic acid sequence of encoding MetAP-3. FIG. 5 shows a comparison between the amino acid sequences of human MetAP-1, MetAP-2, and MetAP-3.

MetAP-1, MetAP-2 and MetAP-3 exhibit different expression profiles when various tissues were sampled. The expression patterns of MetAP-1, MetAP-2 and MetAP-3 are described in Example 4. The expression pattern of MetAP-3 closely correlates with the mitochondrial content of human tissues and MetAP-3 contains a putative mitochondrial signal peptide that directs its sub-cellular localization.

Methionine aminopeptidase activity has been found associated with microsomal and mitochondrial sub-cellular fractions of rat liver (Termignoni, C., Freitas, J. O., and Guimar ães (1991) *Mol. Cell. Biochem.* 102, 101–113). This enzyme, however, was described as a 74,000 Da protein that was incapable of cleaving the releasing methionine from the tripeptide substrate, MAS.

Recently, six aminopeptidase-like genes have been discovered in the *Arapidopsis thaliana* genome (Giglione, C., Serero, A, Pierre, M., Boisson, B., and Meinnel, T. (2000) *EMBO J.* 19, 5916–5929). Four of them have been classified as MetAP-1 homologs and two others as MetAP-2 homologs. All six were differentially expressed in various plant tissues and two of MetAP-1 homologs were found to localize to mitochondria and plant plastids (MetAP-1C and MetAP-1D). Two deformylases were also found that appear to localize to the mitochondria. These results suggest that co-translational protein modifications in the mitochondria are more complex than previously thought.

The human mitochondrial genome encodes 13 protein subunits of the enzymes responsible for electron transport and oxidative phosphorylation. Although no proteins have been sequenced from the human mitochondrial genome, several mitochondrial proteins have been sequenced from bovine, plant, and fungal sources. The initiator methionine is removed from the bovine and potato NADH dehydrogenase subunit 1 and mitochondrial-encoded potato cytochrome b proteins (Dupuis, A., Skehel, J. Ml, and Walker, J. E. (1991) *Biochem. J.* 277, 11–15; Gäbler, L, Herz, U., Liddell, A., Leaver, C. J., Schröder, W., Brennicke, A., and Grohmann, L. (1994) *Mol. Gen. Genet.* 244, 33–40; Braun, H-.P. and Schmitz, U. K. (1993) *FEBS Lett* 316, 128–132]). The initiator methionine is also absent on several mitochondrial or chloroplast encoded ribosomal proteins from broad bean or spinach plants (Maffey, L., Degand, H., and Boutry, M. (1997) *Mol Gen Genet* 254, 365–71; Schmidt, J., Herfurth, E., Subramanian, A. R. (1992) *Plant. Mol. Biol.* 20, 459–65).

ATP synthase F0 subunit 8, cytochrome oxidase subunit II and III, cytochrome b, and NADH dehydrogenase subunit 1, 4L, and 5 could all be potential substrates for a mitochondrial methionine aminopeptidase. The removal of N-terminal methionine from some cytoplasmic proteins by methionine aminopeptidase activity is thought to expose a new amino terminal sequence for myristoylation, proteosome targeting for protein degradation, or acetylation to stabilize the protein (Bradshaw, R. A., Brickey, W. W., and Walker, K. W. (1998) *Trends Biochem. Sci.* 23, 263–7). A methionine aminopeptidase localized within the mitochondria may play similar functions.

Very little is known about the myristoylation of mitochondrial proteins. N-myristoyl transferase (NMT), which requires glycine as a penultimate amino acid, is found only in the cytoplasm (Farazi, T. A., Waksman, G., Gordon, J. I. (2001) *J. Biol. Chem.* 276, 39501–39504). None of the 13 known human mitochondrial proteins should be a substrate for NMT, since they all lack glycine at the amino terminus or within seven residues of the amino terminus that could be exposed by sequential processing by an aminopeptidase.

Most of the mitochondrial proteins are encoded by the nuclear genome and imported into the mitochondria. The B18 subunit of the NADH:ubiquinone oxidoreductase enzyme is N-terminally modified by methionine removal followed by myristoylation of the adjacent glycine (Walker, J. E., Arizmendi, J. M., Dupuis, A., Fearnley, I. M., Finel, M., Medd, S. M., Pilkington, S. J., Runswick, M. J., and Skehel, J. M. (1992) *J. Mol. Biol.* 226, 1051–1072). Since these are co-translational events, they would be predicted to occur in the cytoplasm prior to transport into the mitochondria. Ceramidase was also reported to contain a putative myristoylation site (El Bawab, S., Roddy, P., Qian, T., Bielawska, A., Lemasters, J. J., Hannun, Y. A. (2000) *J. Biol. Chem.* 275, 21508–21513). Cytochrome c oxidase, a mitochondrial inner membrane protein encoded by the mitochondrial genome, was modified on an internal lysine residue by myristic acid (Vassilev, A. O, Plesofsk-Vig, N, and Brambl, R. (1995) *Proc. Natl. Acad. Sci. USA* 92, 8680–8684). This protein is never exposed to the cytoplasm, suggesting that the mitochondria may contain myristoyl transferase enzyme activity.

Proteins which are imported into the mitochondria could also serve as substrates for mitochondrial MetAP-3, if they lack a signal peptide. Mitochondrial signal peptidase recognizes and cleaves between an aromatic/hydrophobic amino acid and a hydrophilic/hydroxyl amino acid (Taylor, A. B., Smith, B. S., Kitada, S., Kojima, K., Miyaura, H., Otwinowski, Z., Ito, A., and Deisenhofer, J. (2001) *Structure* 9, 615–625). Proteins having an exposed N-terminal hydrophilic/hydroxyl amino acid may not be substrates for mitochondrial MetAP-3 until they are processed to have an N-terminal methionine followed by a small or uncharged amino acid residue.

Mitochondrial aminopeptidases could also control the stability of the processed protein, as dictated by the N-end rule of protein degradation. The mitochondrial machinery responsible for protein degradation, however, is a non-ubiquitin system that utilizes AAA peptidases (ATPases Associated with a variety of cellular Activities) (Kaser, M., Langer, T. (2000) *Semin. Cell Dev. Biol.* 11, 181–90). These enzymes do not appear to be sequence specific, but target misfolded integral membrane proteins as preferred substrates.

Mitochondrial MetAP-3 may also play a role in regulating the activity of cell death regulatory proteins that target the mitochondria. GRIM-19, for example, was recently identified as the B16.1 subunit of the NADH:ubiquinone oxidoreductase (complex I) (Fearnley, I. M., Carroll, J., Shannon, R. J., Runswick, M. J., Walker, J. E., Hirst, J. (2001) *J. Biol. Chem.* 276, 38345–38348). GRIM-19 lacks a mitochondrial target presequence, its initiator methionine is removed, and the resulting N-terminal alanine is blocked by acetylation.

Molecules of the Present Invention

The term "angiogenesis" has recognized meaning in the art. The methods of the present invention are particularly relevant in the monitoring of the expression of MetAP-3. The methods of the present invention are also relevant in the monitoring of the expression of MetAP-3 in cancer patients. Molecules of the present invention are capable of being used to diagnose MetAP-3 expression. Molecules of the present invention are also capable of being used to diagnose the level of MetAP-3 expression in cancer patients. Molecules of the present invention can also be used as therapeutic agents and in diagnostic methods.

The molecules of the present invention may be either naturally-occurring or non-naturally occurring. As used herein, a naturally-occurring molecule may be "substantially-pure" or "substantially-purified," if desired, such that one or more molecules that is or may be present in a naturally occurring preparation containing that molecule will have been removed or will be present at a lower concentration than that at which it would normally be found.

The molecules of the present invention will preferably be "biologically active" with respect to either a structural attribute, such as the capacity of a nucleic acid to hybridize to another nucleic acid molecule, or the ability of a protein to be bound by antibody (or to compete with another molecule for such binding). Alternatively, such an attribute may be catalytic, and thus involve the capacity of the agent to mediate a chemical reaction or response.

The molecules of the present invention comprise nucleic acid molecules, proteins, peptides, antibodies, and organic molecules.

Nucleic Acid Molecules

A preferred class of agents of the present invention comprise MetAP-3 nucleic acid molecules. Such molecules may be DNA or RNA.

In one embodiment, such nucleic acid molecules will encode all or a fragment of MetAP-3 protein, preferably human MetAP-3. These nucleic acids optionally contain a "promoter" or flanking gene sequences. As used herein, the term "promoter" is used in an expansive sense to refer to the regulatory sequence(s) that control mRNA production. Such sequences include RNA polymerase binding sites, enhancers, etc. All such MetAP-3 molecules may be used in a diagnostic or therapeutic context.

Fragments of MetAP-3 nucleic acid molecules may encode significant portion(s) of, or most of, the MetAP-3 protein. Preferably, a fragment MetAP-3 nucleic acid molecule is identical or complementary to at least about 12 contiguous nucleotides in SEQ ID NOS: 5, 7, or 69. More preferably it comprises at least about 25 nucleotides in SEQ ID NOS: 5, 7, or 69. Even more preferably it comprises at least about 50 nucleotides in SEQ ID NOS: 5, 7, or 69. Most preferably, it comprises at least about 100 nucleotides in SEQ ID NOS: 5, 7, or 69. Additionally, MetAP-3 nucleic acid molecules and fragment MetAP-3 nucleic acid molecules can possess about 70% to about 95% sequence identity over a region of 12, or about 50 to about 100 contiguous nucleotides of SEQ ID NOS: 5, 7, or 69 or their complements.

In a preferred embodiment, a fragment MetAP-3 nucleic acid molecule comprises at least one nucleotide that is not found in a corresponding position in MetAP-3. In another preferred embodiment, the fragment MetAP-3 protein exhibits MetAP-3 enzymatic activity.

MetAP-3 nucleic acid molecules and fragment MetAP-3 nucleic acid molecules can specifically hybridize with other nucleic acid molecules. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook, et al., *Molecular Cloning*, A Laboratory Manual, 2nd Ed., Cold Spring Harbor Press, Cold Spring Harbor, N.Y. (1989), and by Haymes, et al. *Nucleic Acid Hybridization, A Practical Approach*, IRL Press, Washington, D.C., 1985). Departures from complete complementarity are therefore permissible, as long as such departures do not completely preclude the capacity of the molecules to form a double-stranded structure.

Appropriate stringency conditions which promote DNA hybridization are, for example, 6× sodium saline citrate (SSC) at about 45° C., followed by a wash of 2×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a moderately low stringency of about 2×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to a nucleic acid molecule having SEQ ID NOS: 5, 7, or 69 or their complements under moderately stringent conditions, for example at about 2×SSC and about 40° C. about 50° C.

In a particularly preferred embodiment, a nucleic acid of the present invention will specifically hybridize to SEQ ID NOS: 5, 7, or 69 or their complement under high stringency conditions, such as about 0.2×SSC and about 45° C. to about 65° C. In one aspect of the present invention, a nucleic acid molecule of the present invention will comprise SEQ ID NOS: 5, 7, or 69 or their complement.

Fragment nucleic acid molecules can be determined and selected such that, under specified conditions, such as high stringency, they can be used to specifically hybridize to MetAP-3 sequences and not, for example, to MetAP-1 or MetAP-2 sequences. Furthermore, specific sequences that hybridize to MetAP-3 and not to MetAP-1 or MetAP-2 can be deduced from the sequences using algorithms which are known and available in the art.

In another aspect of the present invention, a nucleic acid molecule of the present invention shares between about 100% and about 70% sequence identity with the nucleic acid sequence set forth in SEQ ID NOS: 5, 7, or 69 or their complements. In a further aspect of the present invention, a nucleic acid molecule of the present invention shares between about 100% and about 95% sequence identity with the nucleic acid sequence set forth in SEQ ID NOS: 5, 7, or 69 or their complements. In a more preferred aspect of the present invention, a nucleic acid molecule of the present invention shares between about 100% and about 98% sequence identity with SEQ ID NOS: 5, 7, or 69 or their complements. In the most preferred aspect of the present invention, a nucleic acid molecule of the present invention shares between about 100% and about 99% sequence identity with SEQ ID NOS: 5, 7, or 69 or their complements.

Homologues and polymorphic sequences, especially single polymorphic sequences, of the human nucleic acids of SEQ ID NOS: 5, 7, or 69 are also provided. A subset of the nucleic acid molecules of the invention includes hybridization or PCR probes which can be used, for example, to identify mammalian MetAP-3 homologue nucleic acids and genes. These probes can also be used to identify genomic clones of MetAP-3, especially human genomic clones, or to identify genomic regions flanking the MetAP-3 gene.

The degeneracy of the genetic code, which allows different nucleic acid sequences to code for the same protein or peptide, is known in the literature. (U.S. Pat. No. 4,757,006). As used herein, a nucleic acid molecule is degenerate of another nucleic acid molecule when the nucleic acid molecules encode for the same amino acid sequences, but comprise different nucleotide sequences. An aspect of the present invention is that the nucleic acid molecules of the present invention include nucleic acid molecules that are degenerate of SEQ ID NOS: 5, 7, or 69 and their complements.

Apart from their other uses, such as those described below, the nucleic acid molecules of the present invention can be employed to obtain other MetAP-3 molecules. Nucleic acid molecules and fragments thereof of the present invention may be employed to obtain other nucleic acid molecules from humans. Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules, or fragments thereof, to screen cDNA or genomic libraries obtained from humans or to search databases of sequence information. Methods for forming such libraries and searching databases are well known in the art.

Nucleic acid molecules and fragments thereof of the present invention may also be employed to obtain nucleic acid homologues. Such homologues include the nucleic acid molecule of other organisms (e.g., monkey, mouse, rat, dog, cat) including the nucleic acid molecules that encode, in whole or in part, protein homologues of other species or other organisms, and sequences of genetic elements such as promoters and transcriptional regulatory elements from other species or organisms. Such molecules can be readily obtained by using the above-described nucleic acid molecules or fragments thereof to screen cDNA or genomic libraries obtained from such species. Methods for forming such libraries are well known in the art. Such homologue molecules may differ in their nucleotide sequences from those found SSEQ ID NOS: 5, 7, or 69 or complement thereof. The nucleic acid molecules of the present invention therefore also include molecules that, although capable of specifically hybridizing with the nucleic acid molecules may lack "complete complementarity."

Any of a variety of methods may be used to obtain one or more of the above-described nucleic acid molecules (Zamechik et al., *Proc. Natl. Acad. Sci.* (*U.S.A.*) 83:4143–4146 (1986); Goodchild et al., *Proc. Natl. Acad. Sci.* (*U.S.A.*) 85:5507–5511 (1988); Wickstrom et al., *Proc. Natl. Acad. Sci.* (*U.S.A.*) 85:1028–1032 (1988); Holt et al., *Molec. Cell. Biol.* 8:963–973 (1988); Gerwirtz et al., *Science* 242:1303–1306 (1988); Anfossi et al., *Proc. Natl. Acad. Sci.* (*U.S.A.*) 86:3379–3383 (1989); Becker et al., *EMBO J.* 8:3685–3691 (1989)). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51:263–273 (1986); Erlich et al., European Patent 50,424; European Patent 84,796, European Patent 258,017, European Patent 237,362; Mullis, European Patent 201,184; Mullis et al., U.S. Pat. No. 4,683,202; Erlich, U.S. Pat. No. 4,582,788; and Saiki, R. et al., U.S. Pat. No. 4,683,194) to amplify and obtain any desired nucleic acid molecule or fragment.

The MetAP-3 promoter sequence(s) and MetAP-3 flanking sequences can also be obtained using the SEQ ID NOS: 5, 7, or 69 sequences provided herein. In one embodiment, such sequences are obtained by incubating oligonucleotide probes of MetAP-3 oligonucleotides with members of genomic human libraries and recovering clones that hybridize to the probes. In a second embodiment, methods of "chromosome walking," or 3' or 5' RACE may be used (Frohman, M. A. et al., *Proc. Natl. Acad. Sci.* (*U.S.A.*) 85:8998–9002 (1988); Ohara, O. et al., *Proc. Natl. Acad. Sci.* (*U.S.A.*) 86:5673–5677 (1989)) to obtain such sequences.

Proteins and Peptides

A second class of preferred agents comprises MetAP-3 protein, shorter polypeptides, or peptide fragments, fusion proteins, and analogs. MetAP-3 protein may be produced via chemical synthesis, or more preferably, by expressing MetAp-3-encoding cDNA in a suitable bacterial or eukaryotic host. Most preferably, the subsequence of such cDNA that encodes MetAP-3 may be used for this purpose (SEQ ID NOS: 5, 7, or 69). Suitable methods for expression are described by Sambrook et al., (In: *Molecular Cloning, a Laboratory Manual*, *2nd Edition*, Cold Spring Harbor Press, Cold Spring Harbor, N.Y. (1989)), or similar texts.

A "MetAP-3 fragment" is a peptide or polypeptide whose amino acid sequence comprises a subset of the amino acid sequence of MetAP-3 protein. Preferably a fragment MetAP-3 molecule is identical or complementary to at least one region which corresponds to a contiguous 10 amino acids of SEQ ID NO: 8; more preferably, at least one region which corresponds to a contiguous 50 amino acids of SEQ ID NO: 8; even more preferably, at least one region which responds to a contiguous 100 amino acids of SEQ ID NO: 8. A MetAP-3 protein or fragment thereof that comprises one or more additional non-MetAP-3 peptide regions or amino acids is a "MetAP-3 fusion" protein. Such molecules may be derivatized to contain carbohydrate or other moieties (such as keyhole limpet hemocyanin, etc.). As in the case of MetAP-3 protein, the fragments and fusions of the present invention are preferably produced via recombinant means.

Additionally, variant MetAP-3 proteins or fragments can be generated by known mutagenesis techniques so that one or more amino acids can be substituted, deleted, or added and the methionine aminopeptidase activity retained. Mutations that avoid or employ conservative substitutions within the known functional region, the C-terminal aminopeptidase domain, the residues that coordinate the cobalt ions, or domains possessing the same position in the amino acid chain as the aminopeptidase domain are preferred. Mutations that avoid changing amino acids at the known methionine aminopeptidase enzymatic active sites are also preferred. Methods to generate banks of mutant proteins, such as molecular evolution or DNA shuffling or the like, can be used. Assays for the methionine aminopeptidase activity that can identify these variant MetAP-3 molecules are also known. Such assays may involve an in vitro peptide substrate analysis (Freitas et al., *Int. J. Biochem.* 17:1285–1291 (1985), Xuo et al., *Mol. Gen. Genet.* 246:247–253 (1995), and Kendall and Bradshaw, *J. Biol. Chem.* 267:20667–10673 (1992)).

The analogs of the MetAP-3 molecules comprise MetAP-3 proteins, fragments or fusions in which nonessential, or non-relevant, amino acid residues have been added, replaced, or deleted. An example of such an analog is the MetAP-3 protein of non-human species, such as primates, mice, rats, dogs, cats, etc. Such analogs can readily be obtained by any of a variety of methods. Most preferably, as indicated above, the disclosed SEQ ID NOS: 5, 7, or 69 will be used to define a pair of primers that may be used to isolate the MetAP-3-encoding nucleic acid molecules from any desired species. Such molecules can be expressed to yield MetAP-3 analogs by recombinant means.

Antibodies Reactive Against MetAP-3

One aspect of the present invention concerns antibodies, single-chain antigen binding molecules, or other proteins that specifically bind to MetAP-3 protein and its analogs, fusions or fragments. Such antibodies are "anti-MetAP-3 antibodies," and may be used, for example to measure MetAP-3 protein. As used herein, an antibody or peptide is said to "specifically bind" to MetAP-3 if such binding is not competitively inhibited by the presence of non-MetAP-3 molecules.

Nucleic acid molecules that encode all or part of the MetAP-3 protein can be expressed, via recombinant means, to yield MetAP-3 protein or peptides that can in turn be used to elicit antibodies that are capable of binding MetAP-3. Such antibodies may be used in immunodiagnostic assays. Such MetAP-3-encoding molecules, or their fragments may be a "fusion" molecule (i.e. a part of a larger nucleic acid molecule) such that, upon expression, a fusion protein is produced.

The antibodies that specifically bind MetAP-3 proteins and protein fragments may be polyclonal or monoclonal, and may comprise intact immunoglobulins, of antigen binding portions of immunoglobulins (such as (F(ab'), $F(ab')_2$) fragments, or single-chain immunoglobulins generated, for example, via recombinant means. It is understood that practitioners are familiar with the standard resource materials which describe specific conditions and procedures for the construction, manipulation and isolation of antibodies (e.g., Harlow and Lane, *In Antibodies: A Laboratory Manual*, Cold Spring Harbor Press, Cold Spring Harbor, N.Y. (1988)).

Murine monoclonal antibodies are particularly preferred. BALB/c mice are preferred for this purpose, however, equivalent strains may also be used. The animals are preferably immunized with approximately 25 $\mu$g of purified MetAP-3 protein (or fragment thereof) that has been emulsified with a suitable adjuvant (such as TiterMax adjuvant (Vaxcel, Norcross, Ga.)). Immunization is preferably conducted at two intramuscular sites, one intraperitoneal site, and one subcutaneous site at the base of the tail. An additional i.v. injection of approximately 25 $\mu$g of antigen is preferably given in normal saline three weeks later. After approximately 11 days following the second injection, the mice may be bled and the blood screened for the presence of anti-MetAP-3 antibodies. Preferably, a direct binding ELISA is employed for this purpose.

Most preferably, the mouse having the highest antibody titer is given a third i.v. injection of approximately 25 $\mu$g of MetAP-3 protein or fragment. The splenic leukocytes from this animal may be recovered 3 days later, and are then permitted to fuse, most preferably, using polyethylene glycol, with cells of a suitable myeloma cell line (such as, for example, the P3X63Ag8.653 myeloma cell line). Hybridoma cells are selected by culturing the cells under "HAT" (hypoxanthine-aminopterin-thymine) selection for about one week. The resulting clones may then be screened for their capacity to produce monoclonal antibodies ("mAbs) to MetAP-3 protein, preferably by direct ELISA.

In one embodiment, anti-MetAP-3 monoclonal antibodies are isolated using MetAP-3 fusions, or conjugates, as immunogens. Thus, for example, a group of mice can be immunized using a MetAP-3 fusion protein emulsified in Freund's complete adjuvant (approximately 50 $\mu$g of antigen per immunization). At three week intervals, an identical amount of antigen is emulsified in Freund's incomplete adjuvant and used to immunize the animals. Ten days following the third immunization, serum samples are taken and evaluated for the presence of antibody. If antibody titers are too low, a fourth booster can be employed. Polysera capable of binding MetAP-3 at 1:5,000 dilution can also be obtained using this method.

In a preferred procedure for obtaining monoclonal antibodies, the spleens of the above-described immunized mice are removed, disrupted, and immune splenocytes are isolated over a Ficoll gradient. The isolated splenocytes are fused, using polyethylene glycol with BALB/c-derived HGPRT (hypoxanthine guanine phosphoribosyl transferase)-deficient P3x63xAg8.653 plasmacytoma cells. The fused cells are plated into 96 well microtiter plates and screened for hybridoma fusion cells by their capacity to grow in culture medium supplemented with hypothanthine, aminopterin and thymidine for approximately 2–3 weeks. On average, out of every $10^6$ spleen cells subjected to fusion yields a viable hybridoma. A typical spleen yields 5–10×$10^7$ spleen cells.

Hybridoma cells that arise from such incubation are preferably screened for their capacity to produce an immunoglobulin that binds to MetAP-3 protein. An indirect ELISA may be used for this purpose. In brief, the supernatants of hybridomas are incubated in microtiter wells that contain immobilized MetAP-3 protein. After washing, the titer of bound immunoglobulin can be determined using, for example, a goat anti-mouse antibody conjugated to horseradish peroxidase. After additional washing, the amount of immobilized enzyme is determined (for example, through the use of a chromogenic substrate). Such screening is performed as quickly as possible after the identification of the hybridoma in order to ensure that a desired clone is not overgrown by non-secreting neighbors. Preferably, the fusion plates are screened several times since the rates of hybridoma growth vary. In a preferred embodiment, a different antigenic form of MetAP-3 may be used to screen the hybridoma. Thus, for example, the splenocytes may be immunized with one MetAP-3 immunogen, but the resulting hybridomas can be screened using a different MetAP-3 immunogen.

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as fluorescent group, a radioisotope or an enzyme).

The ability to produce antibodies that bind MetAP-3 molecules permits the identification of mimetic compounds of MetAP-3. A "mimetic compound" of MetAP-3 is a compound that is not MetAP-3 or a fragment of MetAP-3, but which nonetheless exhibits an ability to specifically bind to anti-MetAP-3 antibodies. Such molecules can be used to elicit anti-MetAP-3 antibodies, and thus, may be used to assist diagnosis of MetAP-3 related disorders.

Uses of the Molecules of the Invention

An aspect of the present invention provides plasmid DNA vectors for use in the expression of the MetAP-3 protein. These vectors contain the DNA sequences described above which code for the polypeptides of the invention. Appropriate vectors which can transform eukaroytic cells, including mammalian cells and microorganisms capable of expressing the MetAP-3 protein include expression vectors comprising nucleotide sequences coding for the MetAP-3 protein joined to transcriptional and translational regulatory sequences which are selected according to the host cells used.

Vectors incorporating modified sequences as described above are included in the present invention and are useful in the production of the MetAP-3 polypeptides. The vector employed in the method also contains selected regulatory sequences in operative association with the DNA coding sequences of the invention which are capable of directing the replication and expression thereof in selected host cells.

Transfer of a nucleic acid that encodes for a protein can result in overexpression of that protein in a transformed cell. One or more of the proteins or fragments thereof encoded by nucleic acid molecules of the present invention may be overexpressed in a transformed cell. Particularly, any of the MetAP-3 proteins or fragments thereof may be overexpressed in a transformed cell. Such overexpression may be the result of transient or stable transfer of the exogenous genetic material. "Exogenous genetic material" is any genetic material, whether naturally occurring or otherwise, from any source that is capable of being inserted into any organism.

A construct or vector may include a promoter to express the protein or protein fragment of choice. Some promoters that can be used in the present invention may include the interleukin-1 alpha promoter (Mori and Prager, *Leuk. Lymphoma* 26:421–433 (1997)), CMV promoter (Tong et al., *Anticancer Res.* 18:719–725 (1998); Norman et al., *Vaccine* 15:801–803 (1997)); RSV promoter (Elshami et al., *Cancer Gene Ther.* 4:213–221 (1997); Baldwin et al., *Gene Ther.* 4:1142–1149 (1997)); SV40 promoter (Harms and Splitter, *Hum. Gene Ther.* 6:1291–1297 (1995)), CD11c integrin gene promoter (Corbi and Lopez-Rodriguez, *Leuk. Lymphoma* 25:415–425 (1997),), GM-CSF promoter (Shannon et al., *Crit. Rev. Immunol.* 17:301–323 (1997)), interleukin-5R alpha promoter (Sun et al., *Curr. Top. Microbiol. Immunol* 211:173–187 (1996)), interleukin-2 promoter (Serfing et al., *Biochim. Biophys. Acta* 1263:181–200 (1995); O'Neill et al., *Transplant Proc.* 23:2862–2866 (1991)), c-fos promoter (Janknecht, *Immunobiology* 193:137–142 (1995); Janknecht et al., *Carcinogenesis* 16:443–450 (1995); Takai et al., *Princess Takamatsu Symp.* 22:197–204 (1991)), h-ras promoter (Rachal et al., *EXS* 64:330–342 (1993)), and DMD gene promoter (Ray et al., *Adv. Exp. Med. Biol.* 280:107–111 (1990)).

Promoters suitable for expression of the MetAP-3 protein or fragment thereof of the present invention in bacteria have been described by Hawley and McClure, *Nucleic Acids Res.* 11:2237–2255 (1983), and Harley and Reynolds, *Nucleic Acids Res.* 15:2343–2361 (1987). Such promoters include, for example, the recA promoter (Fernandez de Henestrosa et al., *FEMS Microbiol. Lett.* 147:209–213 (1997); Nussbaumer et al., *FEMS Microbiol. Lett.* 118:57–63 (1994); Weisemann et al., *Biochimie* 73: 457–470 (1991)), the Ptac promoter (Hasan et al., *Gene* 56:141–151 (1987); Marsh, *Nucleic Acids Res.* 14:3603 (1986)); and a Ptac-recA hybrid promoter.

It is preferred that the particular promoter selected is capable of causing sufficient expression to result in the production of an effective amount of the MetAP-3 protein or fragment thereof to cause the desired phenotype.

Constructs or vectors may also include with the coding region of interest a nucleic acid sequence that acts, in whole or in part, to terminate transcription of that region.

Translational enhancers may also be incorporated as part of the vector DNA. DNA constructs could contain one or more 5' non-translated leader sequences that may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence.

A vector or construct may also include a screenable marker. Screenable markers may be used to monitor expression. Exemplary screenable markers include β-glucuronidase (GUS) encoded by the uidA/gusA gene (Jefferson, *Plant Mol. Biol. Rep.* 5: 387–405 (1987); Jefferson et al., *EMBO J.* 6: 3901–3907 (1987)); β-lactamase (Sutcliffe et al., *Proc. Natl. Acad. Sci.* (*U.S.A.*) 75: 3737–3741 (1978)), luciferase (Clontech, Palo Alto, Calif., USA) (Ow et al., *Science* 234: 856–859 (1986)); β-galactosidase (Clontech, Palo Alto, Calif., USA); GST (Stratagene); Protein A (Calbiochem); and blue and green fluorescent proteins and similar proteins (Clontech, Palo Alto, Calif., USA).

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected by catalytic reactions. Secretable proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell membrane (such as proteins which include a leader sequence). Other possible selectable and/or screenable marker genes are apparent to those of skill in the art.

As another aspect of the present invention, there is provided a method for producing the MetAP-3 protein. Suitable cells or cell lines may be bacterial cells. For example, the various strains of *E. coli* are well-known as host cells in the field of biotechnology. Examples of such strains include *E. coli* strains JM101 (Yanish-Perron et al. *Gene* 33:103–119 (1985)) and MON105 (Obukowicz et al., *Applied Environmental Microbiology* 58:1511–1523 (1992)). Also included in the present invention is the expression of the MetAP-3 protein or fragment thereof utilizing a chromosomal expression vector for *E. coli* based on the bacteriophage Mu (Weinberg et al., *Gene* 126:25–33 (1993)). Various strains of *B. subtilis* may also be employed in this method. Many strains of yeast cells known to those skilled in the art are also available as host cells for expression of the polypeptides of the present invention.

When expressed in the *E. coli* cytoplasm, the gene encoding the MetAP-3 protein or fragment thereof of the present invention may also be constructed such that the 5' end of the gene codons are added to encode $Met^{-2}$-$Ala^{-1}$- or $Met^{-1}$ at the N-terminus of the protein. The N termini of proteins made in the cytoplasm of *E. coli* are affected by post-translational processing by methionine aminopeptidase (Bassat et al., *J. Bacteriol.* 169:751–757 (1987)) and possibly by other peptidases so that upon expression the methionine is cleaved off the N-terminus. The MetAP-3 protein of the present invention may be MetAP-3 polypeptides having $Met^{-1}$, $Ala^{-1}$ or $Met^{2}$-$Ala^{-1}$ at the N-terminus. Other typically small amino acids may also be substituted for alanine.

These MetAP-3 polypeptides may also be expressed in *E. coli* by fusing a secretion signal peptide of the N-terminus. This signal peptide can be cleaved from the polypeptide as part of the secretion process.

Under another embodiment, the MetAP-3 protein or fragment thereof of the present invention is expressed in a yeast cell, preferably *Saccharomyces cerevisiae*. The MetAP-3 protein or fragment thereof of the present invention can be expressed in *S. cerevistae* by fusing it to the N-terminus of the URA3, CYC1 or ARG3 genes (Guarente and Ptashne, *Proc. Natl. Acad. Sci.* (*U.S.A.*) 78:2199–2203 (1981); Rose et al., *Proc. Natl. Acad. Sci.* (*U.S.A.*) 78:2460–2464 (1981); and Crabeel et al., *EMBO J.* 2:205–212 (1983)). Alternatively, the MetAP-3 protein or fragment thereof of the present invention can be fused to either the PGK or TRP1 genes (Tuite et al., *EMBO J.* 1:603–608 (1982); and Dobson et al., *Nucleic Acids. Res.* 11:2287–2302 (1983)). More preferably, the MetAP-3 protein or fragment thereof of the present invention is expressed as a mature protein (Hitzeman et al., *Nature* 293:717–722 (1981); Valenzuela et al., *Nature* 298:347–350 (1982); and Derynck et al., *Nucleic Acids Res.* 11:1819–1837 (1983)).

Native and engineered yeast promoters suitable for use in the present invention have been reviewed by Romanos et al., *Yeast* 8:423–488 (1992). Most preferably, the MetAP-3 protein or fragment thereof of the present invention is secreted by the yeast cell (Blobel and Dobberstein, *J. Cell Biol.* 67:835–851 (1975); Kurjan and Herskowitz, *Cell* 30:933–943 (1982); Bostian et al., *Cell* 36:741–751 (1984); Rothman and Orci, *Nature* 355:409–415 (1992); Julius et al., *Cell* 32:839–852 (1983); and Julius et al., *Cell* 36:309–318 (1984)).

Where desired, insect cells may be utilized as host cells in the method of the present invention. See, e.g., V. A. Luckow, *Protein Eng.* J. L. Cleland., Wiley-Liss, New York, N.Y.: 183–2180 (1996) and references cited therein. In addition, general methods for expression of foreign genes in insect cells using baculovirus vectors are described in: O'Reilly et al., *Baculovirus Expression Vectors: A Laboratory Manual*. New York, W.H. Freeman and Company (1992), and King and Possee, *The Baculovirus Expression System: A Laboratory Guide*, London, Chapman & Hall, (1992). An expression vector is constructed comprising a baculovirus transfer vector, in which a strong baculovirus promoter (such as the polyhedrin promoter) drives transcription of a eukaryotic secretion signal peptide coding region, which is translationally joined to the coding region for the MetAP-3 protein. For example, the plasmid pVL1393 (Invitrogen Corp., San Diego, Calif., U.S.A.) can be used. After construction of the vector carrying the gene encoding the MetAP-3 protein, two micrograms of this DNA is co-transfected with one microgram of baculovirus DNA into *Spodoptera frugiperda* insect cells, strain Sf9. Alternatively, recombinant baculoviruses can be created using a baculovirus shuttle vector system (Luckow et al., *J. Virol.* 67: 4566–4579 (1993)), now marketed as the Bac-To-Bac™ Expression System (Life Technologies, Inc. Rockville, Md.). Pure recombinant baculoviruses carrying the MetAP-3 protein is used to infect cells cultured, for example, in Excell 401 serum-free medium (JRH Biosciences, Lenexa, Kans.) or Sf900-II (Life Technologies, Inc.). The MetAP-3 protein secreted into the medium can be recovered by standard biochemical approaches. Supernatants from mammalian or insect cells expressing the MetAP-3 proteins can be first concentrated using a variety of commercial concentration units.

Mammalian cells can also be used to express the nucleic acid molecules of the present invention. Preferably, the nucleic acid molecules of the present invention are cloned into a suitable retroviral vector (see, e.g., Dunbar et al., *Blood* 85:3048–3057 (1995); Baum et al., *J. Hematother.* 5: 323–329 (1996); Bregni et al., *Blood* 80:1418–1422 (1992); Boris-Lawrie and Temin, *Curr. Opin. Genet. Dev.* 3:102–109 (1993); Boris-Lawrie and Temin, *Annal. New York Acad. Sci.* 716:59–71 (1994); Miller, *Current Top. Microbiol. Immunol.* 158:1–24 (1992)), adenovirus vector (Berkner, *BioTechniques* 6:616–629 (1988); Berkner, *Current Top. Microbiol. Immunol.* 158:39–66 (1992); Brody and Crystal, *Annal. New York Acad. Sci.* 716:90–103 (1994); Baldwin et al., *Gene Ther.* 4:1142–1149 (1997)), RSV, MuSV, SSV, MuLV (Baum et al., *J. Hematother.* 5: 323–329 (1996)), AAV (Chen et al., *Gene Ther.* 5:50–58 (1998); Hallek et al., *Cytokines Mol. Ther.* 2: 69–79 (1996)), AEV, AMV, or CMV (Griffiths et al., *Biochem. J.* 241: 313–324 (1987)).

Alternatively, direct peptide synthesis can be achieved using solid-phase techniques (In: *Solid Phase Peptide Synthesis*, WH Freeman Co., San Francisco Calif., Stewart et al. Eds. (1969), Merrifield, *J. Am Chem. Soc.* 85:2149–2154 (1963)). Automated synthesis may be achieved, for example, using 421A Peptide Synthesizer (Applied Biosystems/Perkin Elmer, Foster City, Calif.) in accordance with the instructions provided by the manufacturer. Chemical protein synthesis can also be an effective way of obtaining functional proteins directly from sequence data. One such approach is chemical ligation, a chemoselective reaction of unprotected peptide segments (Wilken and Kent, Curr. Opin. Biotechnol. 9:412–426 (1998)).

In another aspect, the invention provides a transformed cell having a nucleic acid molecule which comprises an exogenous promoter region which functions in a cell to cause the production of an mRNA molecule which is linked to a structural nucleic acid molecule, wherein the structural nucleic acid molecule encodes a MetAP-3 gene or fragment thereof. This nucleic acid molecule is linked to a 3' non-translated sequence that functions in a cell to cause termination of transcription and addition of polyadenylated ribonucleotides to a 3' end of the mRNA molecule.

Methods and compositions for transforming a eukaryotic cell, bacteria and other microorganisms are known in the art (see, for example, Sambrook et al., *Molecular Cloning: A Laboratory Manual*, Second Edition, Cold Spring Harbor Laboratory Press, Cold Spring Harbor, N.Y., (1989)).

Technology for introduction of DNA into cells is well known to those of skill in the art. Four general methods for delivering a gene into cells have been described: (1) chemical methods (Graham and van der Eb, *Virology* 54:536–539 (1973)); (2) physical methods such as microinjection (Capecchi, *Cell* 22:479–488 (1980)), electroporation (Wong and Neumann, *Biochem. Biophys. Res. Commun.* 107:584–587 (1982); Fromm et al., *Proc. Natl. Acad. Sci.* (*U.S.A.*) 82:5824–5828 (1985); U.S. Pat. No. 5,384,253); and the gene gun (Johnston and Tang, *Methods Cell Biol.* 43:353–365 (1994); (3) viral vectors (Clapp, *Clin. Perinatol.* 20:155–168 (1993); Lu et al., *J. Exp. Med.* 178:2089–2096 (1993); Eglitis and Anderson, *Biotechniques*, 6:608–614 (1988)); and (4) receptor-mediated mechanisms (Curiel et al., *Hum. Gen. Ther.* 3:147–154 (1992), Wagner et al., *Proc. Natl. Acad. Sci.* (*U.S.A.*) 89:6099–6103 (1992)). Other methods well known in the art can also be used.

Transformation can be achieved using methods based on calcium phosphate precipitation, polyethylene glycol treatment, electroporation, and combinations of these treatments (see for example Potrykus et al., *Mol. Gen. Genet.* 205:193–200 (1986); Lorz et al., *Mol. Gen. Genet.* 199:178

(1985); Fromm et al., *Nature* 319:791 (1986); Uchimiya et al., *Mol. Gen. Genet*. 204:204 (1986); Marcotte et al., *Nature* 335:454–457 (1988)).

Assays for gene expression based on the transient expression of cloned nucleic acid constructs have been developed by introducing the nucleic acid molecules into cells by polyethylene glycol treatment, electroporation, or particle bombardment (Marcotte et al., *Nature* 335: 454–457 (1988); McCarty et al., *Cell* 66: 895–905 (1991); Hattori et al., *Genes Dev*. 6: 609–618 (1992); Goff et al., *EMBO J*. 9: 2517–2522 (1990)). Transient expression systems may be used to functionally dissect gene constructs.

In one embodiment, the MetAP-3 molecules of the present invention are used to determine whether an individual has a mutation affecting the level (i.e., the concentration of MetAP-3 mRNA or protein in a sample, etc.) or pattern (i.e., the kinetics of expression, rate of decomposition, stability profile, etc.) of the MetAP-3 expression (collectively, the "MetAP-3 response" of a cell or bodily fluid) (for example, a mutation in the MetAP-3 gene, or in a regulatory region(s) or other gene(s) that control or affect the expression of MetAP-3), and being predictive of individuals who would be predisposed to, for example tumor angiogenesis, and other disorders. As used herein, the MetAP-3 response manifested by a cell or bodily fluid is said to be "altered" if it differs from the MetAP-3 response of cells or of bodily fluids of normal individuals. Such alteration may be manifested by either abnormally increased or abnormally diminished MetAP-3 response. To determine whether a MetAP-3 response is altered, the MetAP-3 response manifested by the cell or bodily fluid of the patient is compared with that of a similar cell sample (or bodily fluid sample) of normal individuals. As will be appreciated, it is not necessary to re-determine the MetAP-3 response of the cell sample (or bodily fluid sample) of normal individuals each time such a comparison is made; rather, the MetAP-3 response of a particular individual may be compared with previously obtained values of normal individuals.

In one sub-embodiment, such an analysis is conducted by determining the presence and/or identity of polymorphism(s) in the MetAP-3 gene or its flanking regions which are associated with a disorder.

Any of a variety of molecules can be used to identify such polymorphism(s). In one embodiment, the MetAP-3 cDNA sequence (or a sub-sequence thereof) may be employed as a marker nucleic acid molecule to identify such polymorphism(s). Alternatively, such polymorphisms can be detected through the use of a marker nucleic acid molecule or a marker protein that is genetically linked to (i.e., a polynucleotide that co-segregates with) such polymorphism(s). In a preferred aspect of this embodiment, such marker nucleic acid molecules will have the nucleotide sequence of a polynucleotide that is closely genetically linked to such polymorphism(s). Polynucleotide markers that map to such locations are well known and can be employed to identify such polymorphism(s).

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 Mb of the polymorphism(s), and more preferably within 100 kb of the polymorphism(s), and most preferably within 10 kb of the polymorphism(s) can be employed.

The genomes of animals and plants naturally undergo spontaneous mutation in the course of their continuing evolution (Gusella, *Ann. Rev. Biochem*. 55:831–854 (1986)).

A "polymorphism" in the MetAP-3 gene or its flanking regions is a variation or difference in the sequence of the MetAP-3 gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e. the original "allele") whereas other members may have the variant sequence (i.e. the variant "allele"). In the simplest case, only one variant sequence may exist, and the polymorphism is thus said to be di-allelic. In other cases, the species' population may contain multiple alleles, and the polymorphism is termed tri-allelic, etc. A single gene may have multiple different unrelated polymorphisms. For example, it may have a di-allelic polymorphism at one site, and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity and paternity analysis (Weber, U.S. Pat. No. 5,075,217; Armour, et al., *FEBS Lett*. 307:113–115 (1992); Jones, et al., *Eur. J. Haematol*. 39:144–147 (1987); Horn, et al., PCT Application WO91/14003; Jeffreys, European Patent Application 370,719; Jeffreys, U.S. Pat. No. 5,175,082); Jeffreys. et al., *Amer. J. Hum. Genet*. 39:11–24 (1986); Jeffreys. et al., *Nature* 316:76–79 (1985); Gray, et al., *Proc. R. Acad. Soc. Lond*. 243:241–253 (1991); Moore, et al., *Genomics* 10:654–660 (1991); Jeffreys, et al., *Anim. Genet*. 18:1–15 (1987); Hillel, et al., *Anim. Genet*. 20:145–155 (1989); Hillel, et al., *Genet*. 124:783–789 (1990)).

The detection of polymorphic sites in a sample of DNA may be facilitated through the use of nucleic acid amplification methods. Such methods specifically increase the concentration of polynucleotides that span the polymorphic site, or include that site and sequences located either distally or proximally to it. Such amplified molecules can be readily detected by gel electrophoresis or other means.

The most preferred method of achieving such amplification employs the polymerase chain reaction ("PCR") (Mullis, et al., *Cold Spring Harbor Symp. Quant. Biol*. 51:263–273 (1986); Erlich et al., European Patent Appln. 50,424; European Patent Appln. 84,796, European Patent Application 258,017, European Patent Appln. 237,362; Mullis, European Patent Appln. 201,184; Mullis et al., U.S. Pat. No. 4,683,202; Erlich, U.S. Pat. No. 4,582,788; and Saiki, et al., U.S. Pat. No. 4,683,194), using primer pairs that are capable of hybridizing to the proximal sequences that define a polymorphism in its double-stranded form.

In lieu of PCR, alternative methods, such as the "Ligase Chain Reaction" ("LCR") may be used (Barany, *Proc. Natl. Acad. Sci*. (*U.S.A*.) 88:189–193 (1991). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069).

The "Oligonucleotide Ligation Assay" ("OLA") may alternatively be employed (Landegren, et al., *Science* 241:1077–1080 (1988)). The OLA protocol uses two oligonucleotides which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson et al. have described a nucleic acid detection assay that combines attributes of PCR and OLA (Nickerson et al., *Proc. Natl. Acad. Sci.* (*U.S.A.*) 87:8923–8927 (1990). In this method, PCR is used to achieve the exponential amplification of target DNA, which is then detected using OLA. In addition to requiring multiple, and separate, processing steps, one problem associated with such combinations is that they inherit all of the problems associated with PCR and OLA.

Schemes based on ligation of two (or more) oligonucleotides in the presence of nucleic acid having the sequence of the resulting "di-oligonucleotide", thereby amplifying the di-oligonucleotide, are also known (Wu et al., *Genomics* 4:560 (1989)), and may be readily adapted to the purposes of the present invention.

Other known nucleic acid amplification procedures, such as allele-specific oligomers, branched DNA technology, transcription-based amplification systems, or isothermal amplification methods may also be used to amplify and analyze such polymorphisms (Malek et al., U.S. Pat. No. 5,130,238; Davey et al., European Patent Application 329,822; Schuster et al., U.S. Pat. No. 5,169,766; Miller et al., PCT appln. WO 89/06700; Kwoh et al., *Proc. Natl. Acad. Sci.* (*U.S.A.*) 86:1173 (1989); Gingeras et al., PCT application WO 88/10315; Walker et al., *Proc. Natl. Acad. Sci.* (*U.S.A.*) 89:392–396 (1992)). All the foregoing nucleic acid amplification methods could be used.

The identification of a polymorphism in the MetAP-3 gene can be determined in a variety of ways. By correlating the presence or absence of tumor angiogenesis in an individual with the presence or absence of a polymorphism in the MetAP-3 gene or its flanking regions, it is possible to diagnose the predisposition of an asymptomatic patient to tumor angiogenesis or other diseases. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms" ("RFLPs"). RFLPs have been widely used in human and animal genetic analyses (Glassberg, UK Patent Application 2135774; Skolnick, M. H. et al., *Cytogen. Cell Genet.* 32:58–67 (1982); Botstein, et al., *Ann. J. Hum. Genet.* 32:314–331 (1980); Fischer, et al. (PCT Application WO90/13668); Uhlen, PCT Application WO 90/11369).

In accordance with this embodiment of the invention, a sample DNA is obtained from a patient's cells. In a preferred embodiment, the DNA sample is obtained from the patient's blood. However, any source of DNA may be used. The DNA is subjected to restriction endonuclease digestion. MetAP-3 is used as a probe in accordance with the above-described RFLP methods.

The polymorphism obtained in this approach can then be cloned to identify the mutation at the coding region which alters the protein's structure, or at the regulatory region of the gene which affects its expression level. Changes involving promoter interactions with other regulatory proteins can be identified by, for example, gel shift.

Several different classes of polymorphisms may be identified through such methods. Examples of such classes include: (1) polymorphisms present in the MetAP-3 cDNA of different individuals; (2) polymorphisms in non-translated MetAP-3 gene sequences, including the promoter or other regulatory regions of the MetAP-3 gene; (3) polymorphisms in genes whose products interact with MetAP-3 regulatory sequences; (4) polymorphisms in gene sequences whose products interact with the MetAP-3 protein, or to which the MetAP-3 protein binds.

In an alternate sub-embodiment, the evaluation is conducted using oligonucleotide "probes" whose sequence is complementary to that of a portion of MetAP-3 mRNA. Such molecules are then incubated with cell extracts of a patient under conditions sufficient to permit nucleic acid hybridization. For this sub-embodiment, cells of the trabecular meshworks are preferred. The detection of double-stranded probe-mRNA hybrid molecules is indicative of the presence of MetAP-3 mRNA; the amount of such hybrid formed is proportional to the amount of MetAP-3 mRNA. Thus, such probes may be used to ascertain the level and extent of MetAP-3 mRNA production in a patient's cells. Such nucleic acid hybridization may be conducted under quantitative conditions (thereby providing a numerical value of the amount of MetAP-3 mRNA present). Alternatively, the assay may be conducted as a qualitative assay that indicates either that MetAP-3 mRNA is present, or that its level exceeds a user set, predefined value.

In a second embodiment, the previously described "anti-MetAP-3 antibodies" are employed in an immunodiagnostic assay.

In one sub-embodiment of this aspect of the present invention, one can ascertain the MetAP-3 Response in a biopsy (or a macrophage or other blood cell sample), or other cell sample, or more preferably, in a sample of bodily fluid (especially, blood, serum, plasma, tears, etc.).

The anti-MetAP-3 antibodies of the present invention may thus be used in an immunoassay to assess the presence of MetAP-3. Any of a wide array of immunoassays formats may be used for this purpose (Fackrell, *Clin. Immunoassay* 8:213–219 (1985)), Yolken, *Rev. Infect. Dis.* 4:35 (1982); Collins, In: *Alternative Immunoassays*, John Wiley & Sons, NY (1985); Ngo, et al., In: *Enzyme Mediated Immunoassay*, Plenum Press, NY (1985)).

The simplest immunoassay involves merely incubating an antibody that is capable of binding to a predetermined target molecule with a sample suspected to contain the target molecule. The presence of the target molecule is determined by the presence, and proportional to the concentration, of any antibody bound to the target molecule. In order to facilitate the separation of target-bound antibody from the unbound antibody initially present, a solid phase is typically employed. Thus, for example the sample can be passively bound to a solid support, and, after incubation with the antibody, the support can be washed to remove any unbound antibody.

In more sophisticated immunoassays, the concentration of the target molecule is determined by binding the antibody to a support, and then permitting the support to be in contact with a sample suspected of containing the target molecule. Target molecules that have become bound to the immobilized antibody can be detected in any of a variety of ways. For example, the support can be incubated in the presence of a labeled, second antibody that is capable of binding to a second epitope of the target molecule. Immobilization of the labeled antibody on the support thus requires the presence of the target, and is proportional to the concentration of the target in the sample. In an alternative assay, the target is incubated with the sample and with a known amount of labeled target. The presence of target molecule in the sample competes with the labeled target molecules for antibody binding sites. Thus, the amount of labeled target molecules that are able to bind the antibody is inversely proportional to the concentration of target molecule in the sample.

In general, immunoassay formats employ either radioactive labels ("RIAs") or enzyme labels ("ELISAs"). RIAs have the advantages of simplicity, sensitivity, and ease of use. Radioactive labels are of relatively small atomic dimension, and do not normally affect reaction kinetics. Such assays suffer, however, from the disadvantages that, due to radioisotopic decay, the reagents have a short shelf-life, require special handling and disposal, and entail the use of complex and expensive analytical equipment. RIAs are described in *Laboratory Techniques and Biochemistry in Molecular Biology*, by Work, et al., North Holland Publishing Company, NY (1978), with particular reference to the chapter entitled "An Introduction to Radioimmune Assay and Related Techniques" by Chard. ELISAs have the advantage that they can be conducted using inexpensive equipment, and with a myriad of different enzymes, such that a large number of detection strategies (colorimetric, pH, gas evolution, etc.) can be used to quantitate the assay. In addition, the enzyme reagents have relatively long shelf-lives, and lack the risk of radiation contamination that attends to RIA use. ELISAs are described in *ELISA and Other Solid Phase Immunoassays* (Kemeny, et al., Eds.), John Wiley & Sons, NY (1988).

Anti-MetAP-3 antibodies or MetAP-3 binding molecules may be administered to a patient, and their capacity to bind to MetAP-3 in vivo may be determined by ocular examination. Significantly, since such a diagnostic test is relatively rapid, immune responses that require significant time, such as the potential eliciting of anti-[anti-MetAP-3]antibodies, or the complexing of such antibodies with anti-MetAP-3 antibodies, is not important. In a preferred embodiment, the antibody will be fluorescently labeled, and will be provided to a patient by injection into the patient's circulatory system.

In another aspect of the present invention, a MetAP-3 protein or fragment thereof can be used in assays for screening test substances for the ability to modulate or maintain MetAP-3 activity. For example, a specific inhibitor of MetAP-3 can be identified using an assay comprising a MetAP-3 protein, fragment, fusion protein, or a cell containing a MetAP-3 protein, fragment, or fusion protein, adding a test compound or composition, and comparing MetAP-1 and MetAP-2 activity to a control. By comparing the effect of a compound or composition on both a MetAP-3 protein and other methionine aminopeptidase proteins, one can identify compounds that specifically effect MetAP-3, or preferentially effect MetAP-3. Thus, specific MetAP-3 inhibitors can be identified using these methods. Conversely, compounds or compositions that specifically or preferentially effect either MetAP-1, MetAP-2, or both can be identified. In similar ways, assays for compounds and compositions that promote, reduce, irreversibly inhibit, or reversibly inhibit methionine aminopeptidase activity in a MetAP-3 protein, fragment, or fusion protein can be screened for. In a sub-embodiment, the test substance is an agonist, antagonist, or small molecule inhibitor of the MetAP-3 protein. In another sub-embodiment, the test substance may bind to MetAP-3 substrate. The test substance may also be an agonist, antagonist, or small molecule inhibitor of MetAP-1 or MetAP-2.

Assays for screening MetAP-3 activity comprise incubating the enzyme with an amount of peptide substrate, stopping the reaction, and quantifying the amount of released methionine. One such assay uses precolumn derivatization and high performance liquid chromatography to measure protease activity (Zuo et al., *Analytical Biochem.* 222:514–516 (1994)).

In another embodiment, the present invention provides a method of using a MetAP-3 protein or fragment thereof in an assay for screening test substances for the ability to modulate or maintain MetAP-3 activity comprising contacting the MetAP enzyme to a peptide substrate, incubating this reaction, then stopping the reaction and determining the amount of released methionine. This assay would be repeated for the other MetAP isozymes to compare activities.

Compositions which modulate or maintain MetAP-3 activity can be tested using cellular assays, such as endothelial cell assays (Rhim et al., *Carcinogenesis* 19:673–81 (1998); Zimrin et al., *Biochem. Biophys. Res. Commun.* 213:630–8 (1995); Madri and Pratt, *J. Histochem. Cytochem.* 34:85–91 (1986)); the chick chorioallantoic membrane assay (CAM) (Ribatti et al., *Int. J. Dev. Biol.* 40:1189–97 (1996); Ribatti et al., *J. Vasc. Res.* 34:455–63 (1997)); or in assays using tumor or other tissues (Montesano et al., Cell. Biol. Int. Rep. 9:8169–75 (1985); Moore et al., *Microvasc. Res.* 56:145–53 (1998)). Animal models of angiogenesis also can be used to evaluate such compositions, including the mouse tumor-induced angiogenesis model (Robertson et al., *Cancer Res.* 51:1339–44 (1991), Carmeliet et al., *Cardiovasc. Res.* 39:8–33 (1998)); the rabbit corneal micropocket model (Ryu and Albert, *Invest Ophthalmol Vis. Sci.* 18:831–41 (1979)); and the rat subcutaneous air sac model (SAS) (Lichtenberg et al., *Pharmacol. Toxicol.* 84:43–40 (1999)). Further, models utilizing human tumor xenografts, such as a variety of tumors xenografted into SCID, nu/nu, or Balb/c mice (Rofstad, *Br. J. Cancer* 70:804–12 (1995); Rofstad, *Mol. Med. Today* 2:394–403 (1996); Lichtenbeld et al., *Int. J. Cancer* 77:455–9 (1998); and Marvin et al., *Eur. J. Pediatr. Surg.* 8:295–8 (1998); Pot-Deprun and Chouroulinkov, *C R Acad Sci Hebd Seances Acad Sci* 280:685–8 (1975)); the Leydig (testicular) tumor implant in rat (Carron et al., *Cancer Res.* 58(9):1930–5 (1998)) can be used to evaluate a compound's ability to modulate or maintain MetAP-3 activity.

Pharmaceutical Compositions

The agents of the present invention can be formulated according to known methods to prepare pharmacologically acceptable compositions, whereby these materials, or their functional derivatives, having the desired degree of purity, are combined in admixture with a physiologically acceptable carrier, excipient, or stabilizer. Such materials are non-toxic to recipients at the dosages and concentrations employed.

The active component of such compositions may MetAP-3 protein, MetAP-3 fusion proteins or fragments of MetAP-3 protein or analogs or mimetics of such molecules. Where nucleic acid molecules are employed, such molecules may be sense, antisense or triplex oligonucleotides of the MetAP-3 cDNA or gene.

A composition is said to be "pharmacologically acceptable" if its administration can be tolerated by a recipient patient. An agent is physiologically significant if its presence results in a detectable change in the physiology of a recipient patient.

Suitable vehicles and their formulation, inclusive of other human proteins, e.g., human serum albumin, are described, for example, in Remington's Pharmaceutical Sciences (16th ed., Osol, Ed., Mack, Easton Pa. (1980).

If the composition is to be water soluble, it may be formulated in a buffer such as phosphate or other organic acid salt preferably at a pH of about 7 to 8. If the composition is only partially soluble in water, it may be prepared as a microemulsion by formulating it with a nonionic surfactant such as Tween, Pluronics, or PEG, e.g., Tween 80, in an amount of, for example, 0.04–0.05% (w/v), to increase its solubility. The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K or Cs salts.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinyl pyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

Additional pharmaceutical methods may be employed to control the duration of action. Controlled or sustained release preparations may be achieved through the use of polymers to complex or absorb the MetAP-3 molecule(s) of the composition. The controlled delivery may be exercised by selecting appropriate macromolecules (for example polyesters, polyamino acids, polyvinyl pyrrolidone, ethylenevinylacetate, methylcellulose, carboxymethylcellulose, or protamine sulfate) and the concentration of macromolecules as well as the methods of incorporation in order to control release.

Sustained release formulations may also be prepared, and include the formation of microcapsular particles and implantable articles. For preparing sustained-release compositions, the MetAP-3 molecule(s) of the composition is preferably incorporated into a biodegradable matrix or microcapsule. A suitable material for this purpose is a polylactide, although other polymers of poly-(a-hydroxycarboxylic acids), such as poly-D-(−)-3-hydroxybutyric acid (EP 133,988A), can be used. Other biodegradable polymers include poly(lactones), poly (orthoesters), polyamino acids, hydrogels, or poly (orthocarbonates) poly(acetals). The polymeric material may also comprise polyesters, poly(lactic acid) or ethylene vinylacetate copolymers. For examples of sustained release compositions, see U.S. Pat. No. 3,773,919, EP 58,481A, U.S. Pat. No. 3,887,699, EP 158,277A, Canadian Patent No. 1176565, Sidman, U. et al., *Biopolymers* 22:547 (1983), and Langer, R. et al., *Chem. Tech.* 12:98 (1982).

Alternatively, instead of incorporating the MetAP-3 molecule(s) of the composition into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

In an alternative embodiment, liposome formulations and methods that permit intracellular uptake of the molecule will be employed. Suitable methods are known in the art; see, for example, Chicz, et al. PCT Application WO 94/04557, Jaysena, et al. (PCT Application WO93/12234, Yarosh, U.S. Pat. No. 5,190,762, Callahan, et al. U.S. Pat. No. 5,270,052 and Gonzalezro, PCT Application WO 91/05771.

The pharmaceutical compositions of the present invention may be sterilized, as by filtration through sterile filtration membranes (e.g., 0.2 micron membranes). The compositions may be stored in lyophilized form or as a liquid solution. It will be understood that use of certain of the foregoing excipients, carriers, or stabilizers will result in the formation of salts of the molecules.

Aspects of the Invention

One aspect of the present invention is to provide a novel methionine aminopeptidase, MetAP-3, and its nucleic acids, proteins, peptides, fragments, homologues, and antibodies to MetAP-3.

Another aspect of the invention is to provide new and advantageous targets to screen for diagnostic and therapeutic agents and compositions useful for diagnosis or treatment of angiogenesis-related diseases.

One embodiment of the present invention relates to a purified and isolated polypeptide selected from the group consisting of: (a) methionine aminopeptidase type 3 (MetAP-3); (b) a polypeptide comprising MetAP-3; (c) a polypeptide having the amino acid sequence of SEQ ID NO 8; and (d) a polypeptide comprising the amino acids set forth in SEQ ID NO 8.

Preferably the purified and isolated polypeptide is MetAP-3.

Preferably the purified and isolated polypeptide is a polypeptide comprising MetAP-3.

Preferably the purified and isolated polypeptide is a polypeptide having the amino acid sequence of SEQ ID NO 8.

Preferably the purified and isolated polypeptide is a polypeptide comprising the amino acid sequence of SEQ ID NO 8.

Another embodiment of the present invention relates to a recombinant polypeptide selected from the group consisting of: (a) MetAP-3; (b) a polypeptide comprising MetAP-3; (c) a polypeptide having the amino acid sequence of SEQ ID NO: 8; and (d) a polypeptide comprising the amino acids set forth in SEQ ID NO: 8.

Preferably the recombinant polypeptide is MetAP-3.

Preferably the recombinant polypeptide is a polypeptide comprising MetAP-3.

Preferably the recombinant polypeptide is a polypeptide having the amino acid sequence of SEQ ID NO: 8.

Preferably the recombinant polypeptide is a polypeptide comprising the amino acid sequence of SEQ ID NO: 8.

Another embodiment of the present invention relates to an isolated and purified antibody having a binding specificity for a polypeptide selected from the group consisting of: (a) MetAP-3; (b) a polypeptide comprising MetAP-3; (c) a polypeptide having the amino acid sequence of SEQ ID NO: 8; and (d) a polypeptide comprising the amino acids set forth in SEQ ID NO: 8.

More preferably the antibody is a polyclonal antibody.

More preferably the antibody is labeled.

Another embodiment relates to a composition comprising said antibody and a solution.

Another embodiment relates to a composition comprising said antibody and an effective carrier, vehicle, or auxiliary agent.

Preferably the antibody binds to a region selected from the group consisting of: (a) MetAP3 peptide antigen-1 (SEQ ID NO: 59); (b) MetAP3 blocking peptide antigen (SEQ ID NO: 62); and (c) MetAP3 peptide antigen-2 (SEQ ID NO: 63).

More preferably the antibody is a polyclonal antibody.

More preferably the antibody is labeled.

Another embodiment relates to a composition comprising said antibody and a solution.

Another embodiment relates to a composition comprising said antibody and an effective carrier, vehicle, or auxiliary agent.

Another embodiment relates to a method for detecting a polypeptide in a biological fluid, wherein said polypeptide is selected from the group consisting of: (a) MetAP-3; (b) a polypeptide comprising MetAP-3; (c) a polypeptide having the amino acid sequence of SEQ ID NO: 8; and (d) a polypeptide comprising the amino acids set forth in SEQ ID NO: 8; comprising the following steps: (i) contacting said fluid with an antibody, having a binding specificity for said polypeptide, and (ii) assaying the presence of said antibody to determine the level of said polypeptide.

Preferably the antibody is labeled.

Another embodiment relates to a method for detecting a first polypeptide in a biological fluid, wherein said first polypeptide is selected from the group consisting of: (a) MetAP-3; (b) a polypeptide comprising MetAP-3; (c) a polypeptide having the amino acid sequence of SEQ ID NO: 8; and (d) a polypeptide comprising the amino acids set forth in SEQ ID NO: 8; comprising the following steps: (i) contacting said fluid with (A) an antibody, having a binding specificity for said first polypeptide, and (B) a second polypeptide capable of binding said antibody, and (ii) assaying the presence of said second polypeptide to determine the level of said first polypeptide.

Preferably the second polypeptide is an antibody.

Preferably the second polypeptide is labeled.

Another embodiment of the invention relates to an isolated nucleic acid molecule selected from the group consisting of: (a) a nucleic acid molecule encoding MetAP-3; (b) a nucleic acid molecule encoding a polypeptide comprising MetAP-3; (c) a nucleic acid molecule encoding a polypeptide having the amino acid sequence of SEQ ID NO: 8; (d) a nucleic acid molecule encoding a polypeptide comprising the amino acids set forth in SEQ ID NO: 8; (e) a nucleic acid molecule comprising the nucleotides set forth in SEQ ID NO: 5; (f) a nucleic acid molecule comprising the nucleotides set forth SEQ ID NO: 7; (g) a nucleic acid molecule comprising the nucleotides set forth SEQ ID NO: 69; (h) a nucleic acid comprising nucleotides 10 through 30 of SEQ ID NO: 24 and nucleotides 30 through 1004 of SEQ ID NO: 7; (includes the ATG start and TGA stop codon) (i) a nucleic acid comprising nucleotides 10 through 30 of SEQ ID NO: 24 and nucleotides 30 through 1001 of SEQ ID NO: 7; (includes the ATG start but excludes the TGA stop codon) (j) a nucleic acid comprising nucleotides 13 through 30 of SEQ ID NO: 24 and nucleotides 30 through 1004 of SEQ ID NO: 7; and (excludes the ATG start and includes the TGA stop codon) (k) a nucleic acid comprising nucleotides 13 through 30 of SEQ ID NO: 24 and nucleotides 30 through 1001 of SEQ ID NO: 7 (excludes the ATG start codon and the TGA stop codon).

The invention also relates to an isolated nucleic acid consisting of a nucleotide sequence that is completely complementary to an nucleic acid molecule selected from the group consisting of: (a) a nucleic acid molecule encoding MetAP-3; (b) a nucleic acid molecule encoding a polypeptide comprising MetAP-3; (c) a nucleic acid molecule encoding a polypeptide having the amino acid sequence of SEQ ID NO: 8; (d) a nucleic acid molecule encoding a polypeptide comprising the amino acids set forth in SEQ ID NO: 8; (e) a nucleic acid molecule comprising the nucleotides set forth in SEQ ID NO: 5; (f) a nucleic acid molecule comprising the nucleotides set forth SEQ ID NO: 7; (g) a nucleic acid molecule comprising the nucleotides set forth SEQ ID NO: 69; (h) a nucleic acid comprising nucleotides 10 through 30 of SEQ ID NO: 24 and nucleotides 30 through 1004 of SEQ ID NO: 7; (i) a nucleic acid comprising nucleotides 10 through 30 of SEQ ID NO: 24 and nucleotides 30 through 1001 of SEQ ID NO: 7; (j) a nucleic acid comprising nucleotides 13 through 30 of SEQ ID NO: 24 and nucleotides 30 through 1004 of SEQ ID NO: 7; and (k) a nucleic acid comprising nucleotides 13 through 30 of SEQ ID NO: 24 and nucleotides 30 through 1001 of SEQ ID NO: 7.

Another embodiment of the invention relates to an isolated nucleic acid molecule encoding MetAP-3.

Another embodiment of the invention relates to an isolated nucleic acid molecule encoding a polypeptide comprising MetAP-3.

Another embodiment of the invention relates to an isolated nucleic acid molecule encoding a polypeptide having the amino acid sequence of SEQ ID NO: 8.

Another embodiment of the invention relates to an isolated nucleic acid molecule encoding a polypeptide comprising the amino acids set forth in SEQ ID NO: 8.

Another embodiment of the invention relates to an isolated nucleic acid molecule comprising the nucleotides set forth in SEQ ID NO: 5.

Another embodiment of the invention relates to an isolated nucleic acid molecule comprising the nucleotides set forth SEQ ID NO: 7.

Another embodiment of the invention relates to an isolated nucleic acid molecule comprising the nucleotides set forth SEQ ID NO: 69.

Another embodiment of the invention relates to an isolated nucleic acid comprising nucleotides 10 through 30 of SEQ ID NO: 24 and nucleotides 30 through 1004 of SEQ ID NO: 7.

Another embodiment of the invention relates to an isolated nucleic acid comprising nucleotides 10 through 30 of SEQ ID NO: 24 and nucleotides 30 through 1001 of SEQ ID NO: 7.

Another embodiment of the invention relates to an isolated nucleic acid comprising nucleotides 13 through 30 of SEQ ID NO: 24 and nucleotides 30 through 1004 of SEQ ID NO: 7.

Another embodiment of the invention relates to an isolated nucleic acid comprising nucleotides 13 through 30 of SEQ ID NO: 24 and nucleotides 30 through 1001 of SEQ ID NO: 7.

A preferred embodiment of the invention relates to an isolated nucleic acid consisting of a nucleotide sequence that is completely complementary to a nucleotide sequence comprising nucleotides 10 through 30 of SEQ ID NO: 24 and nucleotides 30 through 1004 of SEQ ID NO: 7.

A preferred embodiment of the invention relates to an isolated nucleic acid consisting of a nucleotide sequence that is completely complementary to a nucleotide sequence comprising nucleotides 13 through 30 of SEQ ID NO: 24 and nucleotides 30 through 1001 of SEQ ID NO: 7.

A preferred embodiment of the invention relates to vector comprising a nucleic acid selected from the group consisting of: (a) a nucleic acid molecule encoding MetAP-3; (b) a nucleic acid molecule encoding a polypeptide comprising MetAP-3; (c) a nucleic acid molecule encoding a polypeptide having the amino acid sequence of SEQ ID NO: 8; (d) a nucleic acid molecule encoding a polypeptide comprising the amino acids set forth in SEQ ID NO: 8; (e) a nucleic acid molecule comprising the nucleotides set forth in SEQ ID NO: 5; (f) a nucleic acid molecule comprising the nucleotides set forth SEQ ID NO: 7; (g) a nucleic acid molecule comprising the nucleotides set forth SEQ ID NO: 69; (h) a nucleic acid comprising nucleotides 10 through 30 of SEQ ID NO: 24 and nucleotides 30 through 1004 of SEQ ID NO: 7; (i) a nucleic acid comprising nucleotides 10 through 30 of SEQ ID NO: 24 and nucleotides 30 through 1001 of SEQ ID NO: 7; (j) a nucleic acid comprising nucleotides 13 through 30 of SEQ ID NO: 24 and nucleotides 30 through 1004 of SEQ ID NO: 7; and (k) a nucleic acid comprising nucleotides 13 through 30 of SEQ ID NO: 24 and nucleotides 30 through 1001 of SEQ ID NO: 7.

Preferably the vector is selected from the group consisting of a plasmid, a virus, and a bacteriophage.

Preferably the vector of further comprises a promoter operably-linked to said nucleic acid.

More preferably said nucleic acid is inserted into said vector in a proper, sense orientation with respect to said promoter and correct reading frame such that a polypeptide encoded by said nucleic acid may be expressed by a host cell comprising said vector.

A preferred embodiment relates to a method of producing a cell capable of overexpressing a polypeptide comprising introducing into the cell said vector and culturing the cell.

More preferably said nucleic acid is inserted into said vector in an improper, anti-sense orientation with respect to said promoter.

A preferred embodiment relates to a method of producing a cell capable of expressing reduced levels of a polypeptide comprising introducing into the cell said vector wherein said nucleic acid is capable of hybridizing to a mRNA encoding said polypeptide, and culturing the cell.

A preferred embodiment relates to a host cell comprising a vector comprising a nucleic acid selected from the group consisting of: (a) a nucleic acid molecule encoding MetAP-3; (b) a nucleic acid molecule encoding a polypeptide comprising MetAP-3; (c) a nucleic acid molecule encoding a polypeptide having the amino acid sequence of SEQ ID NO: 8; (d) a nucleic acid molecule encoding a polypeptide comprising the amino acids set forth in SEQ ID NO: 8; (e) a nucleic acid molecule comprising the nucleotides set forth in SEQ ID NO: 5; (f) a nucleic acid molecule comprising the nucleotides set forth SEQ ID NO: 7; (g) a nucleic acid molecule comprising the nucleotides set forth SEQ ID NO: 69; (h) a nucleic acid comprising nucleotides 10 through 30 of SEQ ID NO: 24 and nucleotides 30 through 1004 of SEQ ID NO: 7; (i) a nucleic acid comprising nucleotides 10 through 30 of SEQ ID NO: 24 and nucleotides 30 through 1001 of SEQ ID NO: 7; (j) a nucleic acid comprising nucleotides 13 through 30 of SEQ ID NO: 24 and nucleotides 30 through 1004 of SEQ ID NO: 7; and (k) a nucleic acid comprising nucleotides 13 through 30 of SEQ ID NO: 24 and nucleotides 30 through 1001 of SEQ ID NO: 7.

Preferably the host cell is selected from the group consisting of a mammalian cell, a human endothelial cell, an insect cell, a bacterial cell, a plant cell, a fungal cell, a yeast cell, or an Archaeabacterial cell.

More preferably the host cell is a mammalian cell.

More preferably the host cell that is an insect cell.

More preferably the host cell that is a bacterial cell.

A preferred embodiment relates to a host cell which comprises a vector wherein said nucleic acid is inserted into said vector in a proper, sense orientation with respect to said promoter and correct reading frame such that a polypeptide encoded by said nucleic acid may be expressed by a host cell comprising said vector.

Preferably the host cell is selected from the group consisting of a mammalian cell, a human endothelial cell, an insect cell, a bacterial cell, a plant cell, a fungal cell, a yeast cell, or an Archaeabacterial cell.

More preferably the host cell is a mammalian cell.

More preferably the host cell that is an insect cell.

More preferably the host cell that is a bacterial cell.

A preferred embodiment relates to process for producing a polypeptide comprising culturing a host cell under conditions sufficient for the production of said polypeptide, and isolating said polypeptide.

A preferred embodiment relates to a polypeptide produced by said process.

A preferred embodiment relates to a composition consisting essentially of a buffer and a polypeptide produced by said process.

Another embodiment of the invention relates to a composition consisting essentially of a buffer and a polypeptide selected from the group consisting of: (a) MetAP-3; (b) a polypeptide comprising MetAP-3; (c) a polypeptide having the amino acid sequence of SEQ ID NO 8; and (d) a polypeptide comprising the amino acids set forth in SEQ ID NO 8.

Another embodiment of the invention relates to a method for determining the presence of nucleic acid encoding MetAP-3 in a cell comprising: (a) incubating a marker nucleic acid with a nucleic acid derived from or within said cell, said marker nucleic acid capable of specifically hybridizing to a nucleic acid encoding MetAP-3 protein, or a complement thereof, under high stringency conditions, and said marker nucleic acid substantially incapable of specifically hybridizing to a nucleic acid encoding a MetAP-1 or a MetAP-2 protein, or complements of either, under substantially-similar high stringency conditions; (b) permitting hybridization between said marker nucleic acid molecule and said complementary nucleic acid molecule derived from or within said cell; and (c) detecting the presence or amount of hybridized marker nucleic acid.

Another embodiment of the invention relates to a method of removing an N-terminal methionine from a recombinant protein which comprises contacting said recombinant protein with MetAP-3 such that said N-terminal methionine is removed and recovering the resulting recombinant protein.

The invention also provides for a substantially-pure nucleic acid comprising a nucleic acid sequence selected from the group consisting of: SEQ ID NOS: 5, 7, or 69 or complements thereof; nucleic acid sequences that specifically hybridize to SEQ ID NOS: 5, 7, or 69 or complements thereof, especially those that hybridize under stringent conditions; nucleic acid sequences encoding a MetAP-3 protein or fragment thereof, or complement of these nucleic acid sequences; and nucleic acid sequences encoding the amino acid sequence of SEQ ID NO: 8, or complements thereof.

In one embodiment, the present invention relates to a substantially-pure nucleic acid selected from the group consisting of: a nucleic acid molecule comprising SEQ ID NOS: 5, 7, or 69 or their complements, and fragments of either having a length of about 12 to about 650 nucleotides, and a nucleic acid molecule that encodes a protein having a sequence of SEQ ID NO: 8 or a fragment of any having a length of about 10 to about 215 amino acids.

The present invention also relates to a nucleic acid encoding a fragment of a MetAP-3 protein, wherein the nucleic acid is about 12 to 650 nucleotides in length and has from about 99% to about 70% identity to a fragment of SEQ ID NOS: 5, 7, or 69.

In a particularly useful embodiment, a substantially-pure nucleic acid of the invention will specifically hybridize to a nucleic acid molecule encoding MetAP-3 or a complement thereof and fail to specifically hybridize to a nucleic acid molecule encoding MetAP-1, MetAP-2 or a complement of either.

The present invention also provides a substantially-pure MetAP-3 nucleic acid molecule which comprises a nucleic acid sequence that is identical to at least about 12 contiguous nucleotides of SEQ ID NOS: 5, 7, or 69 or their complements.

In a further embodiment, the present invention relates to a substantially-pure MetAP-3 protein or fragment thereof encoded by a nucleic acid sequence encoding a protein having an amino acid sequence of SEQ ID NO: 8 or a fragment of SEQ ID NO: 8 having a length of about 10 to 215 amino acids.

The present invention further relates to a substantially-pure MetAP-3 protein or fragment thereof comprising at least 10 consecutive amino acids of SEQ ID NO: 8, wherein the protein possesses a MetAP activity.

In another embodiment, the present invention relates to a transformed cell having a nucleic acid molecule which comprises a structural nucleic acid molecule, wherein said structural nucleic acid molecule encodes a MetAP-3 protein, peptide, or fragment thereof.

In yet another embodiment, the present invention provides a method for determining a level or pattern of MetAP-3 expressed in a cell comprising: (A) incubating, under conditions permitting nucleic acid hybridization, a marker nucleic acid molecule, the marker nucleic molecule capable of specifically hybridizing to a nucleic acid molecule that encodes MetAP-3 or complement thereof under high stringency conditions and the marker nucleic acid molecule incapable of specifically hybridizing to a nucleic acid molecule that encodes MetAP-1 or MetAP-2 complements of either under high stringency conditions, with a nucleic acid molecule derived from or within the cell; (B) permitting hybridization between the marker nucleic acid molecule and the complementary nucleic acid molecule derived from or within the cell; and (C) detecting the level or pattern of the hybridization. The level or pattern of the hybridized complementary nucleic acid is predictive of the level or pattern of the MetAP-3 protein.

The present invention also relates to a method for detecting the presence of a mutation affecting the level or pattern of MetAP-3 expression comprising the steps: (A) incubating, under conditions permitting nucleic acid hybridization, a marker nucleic acid molecule, the marker nucleic acid molecule comprising a nucleic acid molecule that is linked to a gene, the gene specifically hybridizes to a nucleic acid molecule having a nucleic acid sequence of SEQ ID NO: 8 or the complement thereof, with a nucleic acid molecule derived from or within said cell, wherein hybridization between the marker nucleic acid molecule and the nucleic acid molecule derived from or within the cell permits the detection of a polymorphism whose presence is predictive of a mutation affecting the level or pattern of the MetAP-3 protein in the cell; (B) permitting hybridization between the marker nucleic acid molecule and the nucleic acid molecule derived from or within the cell; and (C) detecting the presence of the hybridization.

In another embodiment, the present invention provides a method for detecting the presence or absence of angiogenic activity in a mammal which comprises assaying the concentration of a molecule whose concentration is dependent upon the expression of a MetAP-3 gene, the molecule being present in a sample of cells or bodily fluid of said mammal, and comparing the concentration of that molecule in the angiogenesis model animal with the concentration of the molecule in a sample of cells or bodily fluid of a control mammal.

In a further embodiment, the present invention relates to a prognostic or diagnostic method for identifying angiogenesis of a tumor in a patient which comprises the steps: (A) incubating, under conditions permitting nucleic acid hybridization, a marker nucleic acid molecule, said marker nucleic acid molecule comprising a nucleotide sequence that specifically hybridizes to a polynucleotide that is linked to a MetAP-3 gene, with a nucleic acid molecule derived from or within a cell or a bodily fluid of said patient, wherein nucleic acid hybridization between said marker nucleic acid molecule and said nucleic acid molecule derived from or within a cell or bodily fluid of said patient is capable of detecting a polymorphism whose presence is predictive of a mutation affecting MetAP-3 response in said patient; (B) permitting hybridization between said marker nucleic acid molecule and said nucleic acid molecule derived from or within a cell or bodily fluid of said patient; and (C) detecting the presence hybridization.

In another embodiment, the present invention relates to a method of determining an association between a polymorphism and a trait comprising: (A) hybridizing a nucleic acid molecule specific for the polymorphism to genetic material of a cell, wherein said nucleic acid molecule comprises a nucleotide sequence of SEQ ID NOS: 5, 7, or 69 or complements thereof; and (B) calculating the degree of association between the polymorphism and the trait.

The present invention also relates to a method of producing a cell capable of overexpressing a MetAP-3 protein comprising: (A) introducing into a cell with a functional nucleic acid molecule, comprising a nucleic acid sequence of SEQ ID NOS: 5, 7, or 69, and (B) culturing the cell. The invention also provides a cell and progeny of a cell produced by such a method.

In another embodiment, the present invention relates to a method for detecting a modification in the methionine-removal activity of cells in a mammal, comprising assaying the concentration of a molecule whose concentration is dependent upon the expression of a MetAP-3 protein, the molecule being present in a sample of cells or bodily fluid of the mammal, and comparing to the concentration of that molecule with that in a sample of cells or bodily fluid from a control mammal.

The present invention also relates to a composition comprising an oligodeoxynucleotide and a pharmaceutically acceptable carrier, the oligodeoxynucleotide comprising a sequence set forth in one of: SEQ ID NOS: 5, 7, or 69 or their complements or fragment of either, having a length of about 12 to about 650 nucleotides.

The present invention further relates to a composition comprising a polypeptide and a pharmaceutically acceptable carrier, said polypeptide comprising an amino acid sequence encoded by a nucleic acid comprising SEQ ID NOS: 5, 7, or 69, or their complement or a fragment of either, having a length of about 12 to about 650 nucleotides; a nucleic acid encoding a protein having a sequence of SEQ ID NO: 8 or a fragment of SEQ ID NO: 8 having a length of about 10 to about 215 amino acids.

In another embodiment, the present invention provides a method of producing a cell capable of expressing reduced levels of a MetAP-3 protein comprising: (A) introducing into a cell a functional nucleic acid molecule, comprising a nucleic acid sequence of SEQ ID NOS: 5, 7, or 69, wherein the functional nucleic acid molecule results in co-suppression of the MetAP protein; and (B) culturing the cell. The invention also provides a cell and progeny of a cell produced by such a method.

In a further embodiment, the present invention provides a method for reducing expression of a MetAP-3 protein in a cell comprising: (A) introducing into a cell with a nucleic acid molecule, said nucleic acid molecule having an exogenous promoter region which functions in a cell to cause the production of a mRNA molecule, wherein said exogenous promoter region is linked to a transcribed nucleic acid molecule having a transcribed strand and a non-transcribed strand, wherein the transcribed strand is complementary to a nucleic acid molecule having a nucleic acid sequence of SEQ ID NOS: 5, 7, or 69 or their complements and said transcribed strand is complementary to an endogenous mRNA molecule; and (B) culturing said cell. The invention also provides a cell and progeny of a cell produced by such a method.

The present invention also provides a method for detecting a compound or composition that modifies the protein phosphorylation activity of a MetAP-3 protein, or a fragment or fusion thereof comprising contacting the compound or composition with a MetAP-3 protein in the presence of a phosphorylating activity and a substrate, allowing a phosphorylation to occur, and detecting the phosphorylation of the substrate in comparison to a control.

The invention also provides a method of isolating a nucleic acid that encodes a MetAP-3 protein or fragment thereof comprising: (A) incubating, under conditions permitting hybridization, a first nucleic acid molecule comprising SEQ ID NOS: 5, 7, or 69, or the complement thereof, with a second nucleic acid molecule obtained or derived from a cell; (B) permitting hybridization between said first nucleic acid molecule and said second nucleic acid molecule; and (C) isolating said second nucleic acid molecule. The invention also provides a cell and progeny of a cell produced by such a method.

In a further embodiment, the present invention provides a method for identifying a molecule, compound, or composition that effects the MetAP activity of a MetAP-3 protein, comprising providing a MetAP-3 protein, contacting the MetAP-3 protein with a test sample comprising a molecule, compound, or composition, and comparing the MetAP activity with a control.

The invention further provides a method of using a MetAP-3 protein or fragment thereof in an assay for screening test substances for the ability to modulate or maintain an activity possessed by a MetAP-3 protein, comprising contacting a MetAP-3 protein or fragment with a test substance, and determining the presence or level of MetAP-3 activity compared to a control.

EXAMPLES

The following examples will illustrate the invention in greater detail, although it will be understood that the invention is not limited to these specific examples. Various other examples will be apparent to the person skilled in the art after reading the present disclosure without departing from the spirit and scope of the invention. It is intended that all such other examples be included within the scope of the appended claims.

General Methods

General methods of cloning, expressing, and characterizing proteins are found in T. Maniatis, et al., *Molecular Cloning, A Laboratory Manual*, Cold Spring Harbor Laboratory, 1982, and references cited therein, incorporated herein by reference; J. Sambrook, et al., *Molecular Cloning, A Laboratory Manual*, $2^{nd}$ edition, Cold Spring Harbor Laboratory, 1989, and references cited therein, incorporated herein by reference; and J. Sambrook, et al., *Molecular Cloning, A Laboratory Manual* (3 *volume set*), $3^{rd}$ edition, Cold Spring Harbor Laboratory, 2001, and references cited therein, incorporated herein by reference. General methods for the culture and biochemical analysis of cells, microscopy, and subcellular location of genes and their products are found in Spector et al., *Cells, A Laboratory Manual* (3 *volume set*), $3^{rd}$ edition, Cold Spring Harbor Laboratory, 1997, and references cited therein, incorporated herein by reference. General and specific conditions and procedures for the construction, manipulation and isolation of antibodies are well known in the art (see, for example, Harlow and Lane, *In Antibodies: A Laboratory Manual*, Cold Spring Harbor Press, Cold Spring Harbor, N.Y. (1988)).

Materials

Unless noted otherwise, all specialty chemicals were obtained from Sigma Chemical Co. (St. Louis, Mo.). Restriction endonucleases and T4 DNA ligase were obtained from Life Technologies, Inc. (Rockville, Md.), New England Biolabs (Beverly, Mass.), Boehringer Mannheim (Indianapolis, Ind.), or Promega (Madison, Wis.). Taq polymerase, EcoRI, HindIII, and NotI restriction enzymes, pFastBacHta and pFastBac-1 vectors, and the GeneTrapper kit were from Gibco/BRL. The QIAquick gel extraction kit was from Qiagen. The pET43a vector and (DE3)plysS *E. coli* strain were from Novagen. Northern blots and ExpressHyb hybridization solutions were from Clontech and the [$^{32}$P]-dATP was a product from Amersham. The Random-Prime It II kit for nick translation and the NucTrap probe purification columns were from Stratagene. Protein gels, running and transfer buffers, and nitrocellulose membranes were purchased from Novex. The stirred-cell concentrator was from Amicon. The hydroxyapatite (type 1) and High Q resins were products of BioRad. The sub-cellular fraction-specific blot was from Calbiochem and the multiple human tissue blot was from DNA Technologies. The goat anti-rabbit peroxidase conjugated antibody was a Jackson ImmunoResearch product. The antibody for detection of the histidine tag was purchase from Santa Cruz Biotechnology. The Pico Western chemiluminescent kit was a Pierce product. The fumagillin, MAS tripeptide, protease inhibitor cocktail, L-amino acid oxidase, and horseradish peroxidase were from Sigma. The Amplex Red was from Molecular Probes, Inc. A SpectraMax 190 plate reader from Molecular Devices was used to monitor the production of resorufin in the MetAP-3 activity assay. All parts are by weight and temperatures are in degrees Centigrade (° C.) unless otherwise indicated.

Plasmids, Viral Expression Vectors, and Sequences

Plasmids and viral expression vectors used in or constructed for this study are listed in Tables 1. A summary of the nucleotide sequences of cloned genes or gene fragments, primers, and amino acid sequences of polypeptides, peptide substrates, and peptides used to generate antibodies are listed in Table 2.

TABLE 1

Plasmids

| Plasmid | Marker | Description | Source |
| --- | --- | --- | --- |
| pFastBac1 | $Amp^R$ $Gent^R$ | Baculovirus donor plasmid containing multiple cloning site downstream of an AcNPV polyhedrin promoter within a mini-Tn7 transposable element capable of being transposed to a baculovirus shuttle vector | Life Technologies Inc. (Rockville, MD) |
| pMON56500 | $Amp^R$ $Gent^R$ | pFastBac1 NotI/EcoRI + MetAP2 PCR fragment EcoRI/NotI encoding untagged MetAP2 | This work |
| pMON56502 | $Amp^R$ $Gent^R$ | pFastBac1 NotI/EcoRI + MetAP-3 PCR fragment EcoRI/NotI encoding untagged MetAP3 | This work |
| pMON56503 | $Amp^R$ $Gent^R$ | pFastBacHTa NotI/EcoRI + MetAP-3 PCR fragment EcoRI/NotI encoding His-tagged MetAP3 | This work |
| pMON57800 | $Amp^R$ $Gent^R$ | pFastBac1 NotI/EcoRI + MetAP-1-HZ PCR fragment EcoRI/NotI encoding untagged MetAP1 | This work |
| pMON57801 | $Amp^R$, $Gent^R$ | pFastBacHTa NotI/EcoRI + MetAP-1-HZ PCR fragment EcoRI/NotI encoding His-tagged MetAP-1 | This work |
| pET43a | $Amp^R$ | *E. coli* expression vectors designed for cloning and high-level expression of peptide sequences fused with the 491 aa Nus-Tag ™ protein | Novagen |
| pET43a-Nus-His-hMetAP-3 | $Amp^R$ | pET43a EcoRI/NotI + EcoRI/NotI MetAP-3 PCR fragment encoding Nus-His-tag fused to MetAP-3 | This work |

TABLE 2

Sequences

| SEQ ID NO | Name or Brief Description | Full or Partial Sequence or Detailed Description | Size | Type |
| --- | --- | --- | --- | --- |
| 1 | *homo sapiens* MetAP1 | | 2671 | DNA |
| 2 | *homo sapiens* MetAP1 | ALFQR . . . | 394 | Protein |
| 3 | *homo sapiens* MetAP2 | | 1908 | DNA |
| 4 | *homo sapiens* MetAP2 | MAGVE . . . | 478 | Protein |
| 5 | *homo sapiens* MetAP3 clone GT9D Insert | | 3114 | DNA |
| 6 | *homo sapiens* MetAP3 insert | MTTEE . . . | 217 | Protein |
| 7 | *homo sapiens* MetAP3HZ2 - full length | | 1529 | DNA |
| 8 | *homo sapiens* MetAP3HZ2 - full length | MAAPS . . . | 388 | Protein |

TABLE 2-continued

Sequences

| SEQ ID NO | Name or Brief Description | Full or Partial Sequence or Detailed Description | Size | Type |
|---|---|---|---|---|
| 9 | *Saccharomyces cerevisiae* MetAP1 | MSTAT . . . | 387 | Protein |
| 10 | *Synechocystis* sp. MetAP1 | | 253 | Protein |
| 11 | *Synechocystis* sp. MetAP2 | | 274 | Protein |
| 12 | *E. coil* MetAP | | 264 | Protein |
| 13 | *Haemophilus influenzae* MetAP | MAIPI . . . | 268 | Protein |
| 14 | Synechocystis sp. MetAP | | 305 | Protein |
| 15 | *Bacillus subtilus* MetAP | MIICK . . . | 248 | Protein |
| 16 | *MUS musculus* MetAP2 | MAGVE . . . | 478 | Protein |
| 17 | Rattus MetAP2 | MAGVE . . . | 478 | Protein |
| 18 | *Saccharomyces cerevisiae* MetAP2 | MTDAE . . . | 421 | Protein |
| 19 | *Methanothermus fervidus* MetAP | MEKFK . . . | 188 | Protein |
| 20 | Methanothermus *jannaschii* MetAP | MEIEG . . . | 294 | Protein |
| 21 | *Sulfolobus solfataricus* MetAP | MTEDE . . . | 301 | Protein |
| 22 | *Helicobacter pylori* MetAP | MAISI . . . | 250 | Protein |
| 23 | *Homo sapiens* MetAP-3 for1 primer | 5'- AGGACGAATGTGGTAAAAAG - 3' | 20 | DNA |
| 24 | *homo sapiens* MAP3 FOR+ADAPT+ATG primer | 5'- CTAGAATTCATGGCGGCGCCCAGTGGCGTC - 3' | 30 | DNA |
| 25 | *homo sapiens* MAP3 REV-NotI primer | 5'- TGCGGCCGCTCAGGCCTCATGGGGTAG - 3' | 27 | DNA |
| 26 | *homo sapiens* MAP3 FOR2 primer | 5'- ACAATCAGCCACATAAC - 3' | 17 | DNA |
| 27 | *homo sapiens* MAP3 FOR3 primer | 5'- TTCTCTTCACCACTCAATC - 3' | 19 | DNA |
| 28 | *homo sapiens* MAP3 FOR4 primer | 5'- GTTTCTCTTTCCCTTGC - 3' | 17 | DNA |
| 29 | *homo sapiens* MAP3 FOR5 primer | 5'- GCCACATTCAGCCTTCAAGGC - 3' | 21 | DNA |
| 30 | *homo sapiens* MAP3 REV1 primer | 5'- ATCCCTCCGTGATGATTGGC - 3' | 20 | DNA |
| 31 | *homo sapiens* MAP3 REV2 primer | 5'- GCAAGGGAAAGAGAAAC - 3' | 17 | DNA |

TABLE 2-continued

Sequences

| SEQ ID NO | Name or Brief Description | Full or Partial Sequence or Detailed Description | Size | Type |
|---|---|---|---|---|
| 32 | *homo sapiens* MAP3 REV1.2 primer | 5'- AGCCCCTGCTCTGCAAGCTGCA - 3' | 22 | DNA |
| 33 | *homo sapiens* MAP3 REV3 primer | 5'- TCCATAGCCTAGAGGTGAGGG - 3' | 21 | DNA |
| 34 | *homo sapiens* MAP3 REV4 primer | 5'- AAGGCCAGCTGAACCCT - 3' | 17 | DNA |
| 35 | *homo sapiens* hmap1F1 primer | 5'- AAGCGGTCTGCTCAGTTTGAG - 3' | 21 | DNA |
| 36 | *homo sapiens* hmap1R1 primer | 5'- GGCCGTGCACTGTCAAGT - 3' | 18 | DNA |
| 37 | *homo sapiens* hmap1P1 | 5'- ACACCCTCCTGGTCACAGACACTGGC - 3' | 26 | DNA |
| 38 | *homo sapiens* hmap2F1 primer | 5'- GACCCTCCCTCAGTTCCAATATG -3' | 23 | DNA |
| 39 | *homo sapiens* hmap2R1 primer | 5'- GTGGGTGGGTATTCGCATTC - 3' | 20 | DNA |
| 40 | *homo sapiens* hmap2P2 primer | 5'- ACCTGTATCCTAATGGTGTATTTCCCAAAGGACA - 3' | 34 | DNA |
| 41 | *homo sapiens* hmap3F1 primer | 5'- GGCATCATGCAAACGACAGT - 3' | 20 | DNA |
| 42 | *homo sapiens* hmap3R1 primer | 5'- ACTGCGCCGACCTTTGATT - 3' | 19 | DNA |
| 43 | *homo sapiens* hmap3R1 primer | 5'- AGAGCCAATCATCACGGAGGGATCC - 3' | 25 | DNA |
| 44 | *homo sapiens* map2bF primer | 5'- TTGGAAGACTGTTCACGCAAGT - 3' | 22 | DNA |
| 45 | *homo sapiens* map2bR primer | 5'- GTCACCGGCATTCGGAGTAT - 3' | 20 | DNA |
| 46 | *homo sapiens* map2bP primer | 5'- TGGATGTTCTCTCAATAATTGTGCTGCCCAT - 3' | 31 | DNA |
| 47 | *homo sapiens* mp3bF primer | 5'- AACGTGCTCTGTCATGGTATTCC - 3' | 23 | DNA |
| 48 | *homo sapiens* mp3bR primer | 5'- AGCCATTGTAATAGACTGTGACATCAA - 3' | 27 | DNA |
| 49 | *homo sapiens* mp3bP primer 3' | 5'- ACAGTCGACCTCTTCAGGATGGAGATATTATCAAC - | 35 | DNA |
| 50 | *homo sapiens* mp3cF primer | 5'- CATGGAGACACCTCTGAAACATTT - 3' | 24 | DNA |
| 51 | *homo sapiens* mp3cR primer | 5'- CCTGGCAACCTCCACTAACTTT - 3' | 22 | DNA |
| 52 | *homo sapiens* mp3cP primer | 5'- CACATTCGTCCTCATTGCCCACCA - 3' | 24 | DNA |
| 53 | *homo sapiens* hcycmesF primer | 5'- CCCACCGTGTTCTTCGACAT - 3' | 20 | DNA |
| 54 | *homo sapiens* hcycmesR primer | 5'- TTTCTGCTGTCTTTGGGACCTT - 3' | 22 | DNA |
| 55 | *homo sapiens* hcycmesP primer | 5'- CGCGTCTCCTTTGAGCTGTTTGCA - 3' | 24 | DNA |

TABLE 2-continued

Sequences

| SEQ ID NO | Name or Brief Description | Full or Partial Sequence or Detailed Description | Size | Type |
|---|---|---|---|---|
| 56 | *homo sapiens* revmp3cP primer | 5'- CACATTCGTCCACATTGCCCACCA - 3' | 24 | DNA |
| 57 | MetAP1 peptide antigen 1 | Asn Glu Thr Phe Phe Val Gly Glu Val Asp Asp Gly Ala Arg Lys Leu Val Gln Thr Thr | 20 | Protein |
| 58 | MetAP2 peptide antigen | Cys Ala Phe Thr Val Thr Phe Asn Pro Lys Tyr Asp Thr Leu Leu Lys Ala Val Lys Asp | 20 | Protein |
| 59 | MetAP3 peptide antigen-1 | Ser Glu Thr Phe Leu Val Gly Asn Glu Asp Glu Ala Gly Lys Lys Leu Val Glu Val Ala | 20 | Protein |
| 60 | MetAP1 blocking peptide antigen | Gly Trp Gln Asp Glu Thr Trp Pro Asp Gly Trp Thr Ala Val Thr Arg Asp Gly Lys Arg | 20 | Protein |
| 61 | MetAP2 blocking peptide antigen | Cys Ser His Tyr Met Lys Asn Phe Asp Val Gly His Val Pro Ile Arg Leu Pro Arg Thr | 20 | Protein |
| 62 | MetAP3 blocking peptide antigen | Gly Ser Pro Glu Phe Lys Val Leu Glu Asp Ala Trp Thr Val Val Ser Leu Asp Asn Gln | 20 | Protein |
| 63 | MetAP3 peptide antigen-2 | Ser Glu Thr Phe Leu Val Gly Asn Val Asp Glu Cys Gly Lys Lys Leu Val Glu Val Ala | 20 | Protein |
| 64 | MetAP-1 forward primer | 5'- ACTTGCATCAAGCTGGGCAT - 3' | 20 | DNA |
| 65 | MetAP-2 5' primer | 5'- CTAGAATTCATGGCGGGTGTGGAGGAGGTA - 3' | 30 | DNA |
| 66 | MetAP-2 3' primer | 5'- TGCGGCCGCTTAATAGTCATCTCCTCTGCT - 3' | 30 | DNA |
| 67 | MAP substrate | Met Gly Met Met Lys | 5 | Protein |
| 68 | Mouse MetAP-3 | | 334 | Protein |
| 69 | Human MetAP-3 PCR fragment | nucleotides 1-30 of PCR primer SEQ ID NO: 24; Nucelotides 18-1004 of MetAP-3 clone SEQ ID NO: 7 with majority of CDS and stop codon; Reverse complement of nucleotides 1-9 of PCR primer SEQ ID NO: 25 | 1026 | DNA |

Transformation of *E. coli* Strains

*E. coli* strains such as DH5 alpha and DH10B (Life Technologies, Rockville, Md.), and TG1 (Amersham Corp., Arlington Heights, Ill.) are routinely used for transformation of ligation reactions and are the hosts used to prepare plasmid DNA for transfecting mammalian cells. *E. coli* strains, such as JM101 (Yanisch-Perron et al., *Gene*, 33: 103–119, 1985) and MON105 (Obukowicz, et al., *Appl. and Envir. Micr.*, 58: 1511–1523, 1992) can be used for expressing the proteins of the present invention in the cytoplasm or periplasmic space.

DH10B and DH5alpha subcloning efficiency cells are purchased as competent cells and are ready for transformation using the manufacturer's protocol. Other *E. coli* strains are rendered competent to take up DNA using a $CaCl_2$ method. Typically, 20 to 50 mL of cells are grown in LB medium (1% Bacto-tryptone, 0.5% Bacto-yeast extract, 150 mM NaCl) to a density of approximately 1.0 absorbance unit at 600 nanometers (OD600) as measured by a Baush & Lomb Spectronic spectrophotometer (Rochester, N.Y.). The cells are collected by centrifugation and resuspended in one-fifth culture volume of $CaCl_2$ solution (50 mM $CaCl_2$, 10 mM Tris-Cl, 10 mM 2-amino-2-(hydroxymethyl) 1,3-propanediol hydrochloride, pH7.4) and are held at 4° C. for 30 minutes. The cells are again collected by centrifugation and resuspended in one-tenth culture volume of $CaCl_2$ solution. Ligated DNA is added to 0.2 mL of these cells, and the samples are held at 4° C. for 30–60 minutes. The samples are shifted to 42° C. for two minutes and 1.0 mL of LB is added prior to shaking the samples at 37° C. for one hour. Cells from these samples are spread on plates (LB medium plus 1.5% Bacto-agar) containing either ampicillin (100 micrograms/mL, ug/mL) when selecting for ampicillin-resistant transformants, or spectinomycin (75 ug/mL) when selecting for spectinomycin-resistant transformants. The plates are incubated overnight at 37° C.

Colonies are picked and inoculated into LB plus appropriate antibiotic (100 ug/mL ampicillin or 75 ug/mL spectinomycin) and are grown at 37° C. while shaking.

DNA Isolation and Characterization

Plasmid DNA can be isolated by a number of different methods and using commercially available kits known to those skilled in the art. Plasmid DNA is isolated using the Promega Wizard™ Miniprep kit (Madison, Wis.), the Qiagen QIAwell Plasmid isolation kits (Chatsworth, Calif.) or Qiagen Plasmid Midi or Mini kit. These kits follow the same general procedure for plasmid DNA isolation. Briefly, cells are pelleted by centrifugation (5000×g), the plasmid DNA released with sequential NaOH/acid treatment, and cellular debris is removed by centrifugation (10000×g). The supernatant (containing the plasmid DNA) is loaded onto a column containing a DNA-binding resin, the column is washed, and plasmid DNA eluted. After screening for the colonies with the plasmid of interest, the *E. coli* cells are inoculated into 50–100 ml of LB plus appropriate antibiotic for overnight growth at 37° C. in an air incubator while shaking. The purified plasmid DNA is used for DNA sequencing, further restriction enzyme digestion, additional subcloning of DNA fragments and transfection into *E. coli*, mammalian cells, or other cell types.

DNA Sequencing Protocol

DNA samples were prepared containing 500 ng of template DNA and 100 ng of primer of choice in thin-walled 0.2 mL PCR tubes that have been brought to 12 uL with Millipore milli-Q (mQ)-quality water. 2 uL of 2 mM $Mg^{+2}$ was added to each tube. Tubes were denatured for 5 minutes at 96 degrees in a Perkin-Elmer System 9700 thermal cycler. After denaturation, the tubes were chilled to a temperature of 4 degrees Celsius by the thermal cycler. 6 uL of ABI Prism Big Dye Terminator Cycle Sequencing Ready Reaction Kit was added to each tube. The samples were returned to the thermal cycler and cycle-sequenced using the following program: (1) 96° C. for 30 (2) 50° C. for 5 sec; (3) 60° C. for 4 min, followed by step (1) for 24 additional cycles and then held at 4° C. Cycle sequencing was complete after about 2.5 hours. Samples were purified through a Millipore MAHV N45 50 Multiscreen-HV filtration plate which had been filled with 25 uL Sephadex G-50 superfine resin and 300 uL mQ water. Before loading samples onto filtration plates, the plate was prespun in a centrifuge at 750×G for 2 min to remove excess water. The samples were loaded onto the resin and the plate spun again at 750×G for 4 min. The purified sample was collected into a 96-well plate that was placed directly underneath the Sephadex-filled plate during the spin. The liquid in the 96-well plate was dried at room temperature in a Speed Vac. After 45–60 min the DNA was dried and pelleted at the bottom of the plate. Samples were resuspended in 3 uL of a formamide/blue Dextran loading dye and were heated for 2 minutes (see p. 33 of Perkin-Elmer Big Dye manual for loading buffer recipe). Samples were loaded onto a 48 cm well-to-read length 4.5% acrylamide gel and were sequenced for 7 hr using run module Seq Run 48E-1200 and dye set DT (BD Set Any-Primer). The Perkin-Elmer Data Collection and Sequence Analysis programs assign bases to the data collected.

Example 1

Cloning of a Partial cDNA Encoding MetAP-3

Cloning of Human MetAP-3

When the catalytic domains of human MetAP-1 and MetAP-2 were used in search strings in a Blast search (Altschul, S. F., Gish, W., Miller, W., Myers, E. W. and Lipman, D. J. (1990) *J. Mol. Biol.*, 215, 403–410) of an Incyte human cDNA database, a partial clone (with an incomplete open reading frame) was identified (ID 2937276). This sequence was used to design a forward oligonucleotide primer, (MetAP-3 for 1) 5'-AGGACGAATGTGGTAAAAAG-3' (SEQ ID NO: 23)

that was biotinylated and used as a probe to identify and enrich for the similar cDNAs from human brain, heart, muscle, and transformed baby hamster kidney fibroblast (BHK-HS-5) cDNA libraries using a GeneTrapper protocol (See Example 3, below). The HS-5 cDNA library provided the strongest signals, and an apparent full length clone (with a full length coding region), designated MetAP-3A (MetAP3-GT9D) was isolated. The clone had a ~3 kb insert which was sequenced (SEQ ID NO: 5). Analysis of the sequence, however, suggested that this clone contained an incomplete coding region. This sequence was used to search the Incyte database for related clones with more upstream sequence. A second MetAP-3 clone was found, ID 2480296, which aligned with the MetAP-3A (MetAP3-GT9D) clone. Sequence comparison revealed that the MetAP-3A clone contained a 50 bp insert and that the Incyte clone ID 2480296 was also missing the 'AT' of the apparent ATG start codon present in the MetAP-3A clone. If the insert is removed, a larger open reading frame, ORF, in frame with the original ORF is created.

Example 2

Cloning of a Full-length cDNA Clone Encoding Human MetAP-3

A second clone, MetAP-3B (MetAP3-HZ2), was obtained from a human brain cDNA library using the GeneTrapper protocol (See Example 3, below) and the same biotinylated forward primer, (MetAP-3 for1) 5'-AGGACGAATGTGGTAAAAAG-3' (SEQ ID NO: 23)

The resulting clone, designated MetAP-3B, contained a 1.5 kb insert, which was fully sequenced. It did not contain the 50 bp insert present in the MetAP3A clone, had a truncated 3' untranslated region, and was also missing the entire ATG initiation codon (SEQ ID NO: 7).

Two oligonucleotides, designated

```
MAP3 FOR + ADAPT + ATG:  CTAGAATTC ATG GCG GCG CCC AGT GGC GTC  (SEQ ID NO: 24)
and                         EcoRI

MAP3 REV-NotI:           TGCGGCCGCTCAGGCC TCA TGG GGT AG        (SEQ ID NO: 25)
                            NotI  ***  StuI
```

were then designed and used to incorporate restriction sites, rebuild the ATG start codon, and amplify just the coding region of this new MetAP-3 gene. The EcoRI site in SEQ ID NO: 24 and the NotI and StuI sites in SEQ ID NO: 25 are underlined, above. The ATG codon (shown in bold) and subsequent codons in SEQ ID NO: 24 are separated by spaces, and the reverse complement of the TGA codon (indicated by a ***) and preceding codons in SEQ ID NO: 25, separated by spaces, are shown above. Using this primer set, the MetAP3B (MetAP3-HZ2) clone served as the template to amplify the apparent 1008 base pair coding region of human MetAP-3 by polymerase chain reaction (PCR). The resulting product, having a sequence beginning and ending as shown below,

```
ctagaattc ATG GCG GCG CCC AGT GGC GTC . . . . . . CTA CCC CAT GAG GCC TGA gcggccgca
   EcoRI                                                         StuI      NotI
```

was verified to be the correct size by visualization on a 1% agarose, 1×TAE gel (lowercase letters indicate noncoding regions). The PCR product was digested with EcoRI and NotI, verified to be the correct size by visualization on a 1% agarose gel, and purified using the QIAquick gel extraction kit. The nucleotide sequence of the PCR product is SEQ ID NO: 69. The amino acid sequence encoded by this fragment is SEQ ID NO: 8.

The baculovirus expression vectors pFASTBAC-1 and pFASTBAC-HTa (Life Technologies, Inc., Rockville, Md.) were prepared for ligation by restriction enzyme digestion with EcoRI and NotI and gel purification of the resulting linearized vector. pFASTBAC-1 and pFASTBAC-HTa were individually ligated with the prepared coding region of MetAP3-HZ2. The HT series of vectors encode histidine tags that facilitate of fusion proteins on nickel columns. *E. coli* strain DH10B (Life Technologies, Inc., Rockville, Md.) was transformed with the ligation products. The resulting colonies were screened by restriction enzyme analysis with EcoRI and NotI, for constructs containing the correct insert size, 1008 bp. Positives, by size screen, were analyzed by sequence analysis at 5' and 3' ends using vector-specific oligonucleotides which flank the insert site containing bacteriophage T7 and SP6 promoters. Inserts having the correct sequence were fully sequenced using gene-specific oligonucleotides.

A summary of the oligonucleotides used as PCR gene amplification and sequencing primers in this and subsequent examples are shown below.

| | | |
|---|---|---|
| Met AP3-For1: | 5'- AGGACGAATGTGGTAAAAAG - 3' | (SEQ ID NO: 23) |
| MAP3 FOR + ADAPT + ATG: | 5'- CTAGAATTCATGGCGGCGCCCAGTGGCGTC - 3' | (SEQ ID NO: 24) |
| MAP3 REV-NotI: | 5'- TGCGGCCGCTCAGGCCTCATGGGGTAG - 3' | (SEQ ID NO: 25) |
| MAP3 FOR2: | 5'- ACAATCAGCCACATAAC - 3' | (SEQ ID NO: 26) |
| MAP3 FOR3: | 5'- TTCTCTTCACCACTCAATC - 3' | (SEQ ID NO: 27) |
| MAP3 FOR4: | 5'- GTTTCTCTTTCCCTTGC - 3' | (SEQ ID NO: 28) |
| MAP3 FOR5: | 5'- GCCACATTCAGCCTTCAAGGC - 3' | (SEQ ID NO: 29) |
| MAP3 REV1: | 5'- ATCCCTCCGTGATGATTGGC - 3' | (SEQ ID NO: 30) |
| MAP3 REV2: | 5'- GCAAGGGAAAGAGAAAC - 3' | (SEQ ID NO: 31) |
| MAP3 REV1.2: | 5'- AGCCCCTGCTCTGCAAGCTGCA - 3' | (SEQ ID NO: 32) |
| MAP3 REV3: | 5'- TCCATAGCCTAGAGGTGAGGG - 3' | (SEQ ID NO: 33) |
| MAP3 REV4: | 5'- AAGGCCAGCTGAACCCT - 3' | (SEQ ID NO: 34) |

Sequence Analysis

A comparison of portions of the nucleotide sequences of the MetAP3B (MetAP3-HZ2; SEQ ID NO: 7) and MetAP-3A (MetAP3-GT9D; SEQ ID NO: 5) is shown in FIG. 3. The amino acid sequence for human MetAP-3 encoded by the PCR product (SEQ ID NO: 8) is shown in FIGS. 2A, 2B, and 4.

As shown in FIG. 4, the 1,008 base pair open reading frame of hMetAP-3 codes for a putative protein of 335 amino acids with a predicted molecular weight of approximately 37,500 Da. The human MetAP-3 protein shares 37% and 13% sequence identity to human MetAP-1 and human MetAP-2, respectively. The predicted sequence of mouse MetAP-3-like protein (MetAPL1, accession number NM 025633) (SEQ ID NO: 67) is 92% identical to human MetAP-3 (FIG. 2A).

FIGS. 1A, 1B, and 1C show phylogenetic trees comparing the amino acid sequences of various aminopeptidases. In FIG. 1A, human MetAP-3 is most closely related to a mouse MetAP-3-like enzyme. In FIG. 1B, (like FIG. 1A, but lacking the mouse enzyme) human MetAP-3 is most closely related to human MetAP-1. In FIG. 1C, (like FIG. 1B, but including a partial MetAP-3, encoded by the cDNA containing the 50 base insert) full-length human MetAP-3 is most closely related to the partial human MetAP-3.

MetAP-3 should be active as an aminopeptidase since there is absolute conservation of the critical residues known for cobalt coordination within hMetAP-1 and hMetAP-2 (Liu, S., Widon, J., Kemp, C. W., Crews, C. M., and Clardy, J. (1998) *Science* 282, 1324–1327). Like hMetAP-1, hMetAP-3 does not contain the carboxy terminal extension of hMetAP-2 that is known to interact with the eukaryotic initiation factor, eIF2α (Wu, S., Gupta, S., Chatterjee, N., Hileman, R. E., Kinzy, T. G., Denslow, N. D., Merrick, W. C., Chakrabarti, D., Osterman, J. C., and Gupta N. K. (1993) *J. Biol. Chem.* 268, 10796–81).

Example 3

Isolation of MetAP cDNAs Using a GeneTrapper Selection System

The GeneTrapper cDNA Positive Selection System (Catalog No.10356-046) marketed by Life Technologies, Inc. (Rockville, Md.) was used to identify clones encoding methionine aminopeptidase types 1, 2, and 3 with minor changes in the protocol noted below. The GeneTrapper cDNA Positive Selection System facilitates the rapid (1 to 2 days) isolation of cDNA clones from DNA prepared from a cDNA library (representing $10^{12}$ DNA molecules). In this system, an oligonucleotide, complementary to a segment of the target cDNA, is biotinylated at the 3'-end with biotin-14-dCTP using terminal deoxynucleotidyl transferase (TdT). Simultaneously, a complex population of double-stranded (ds) phagemid DNA containing cDNA inserts ($10^6$ to $10^7$ individual members) is converted to ssDNA using Gene II (phage F1 endonuclease) and *E. coli* Exonuclease III (Exo III). Hybrids between the biotinylated oligonucleotide and ssDNA are formed in solution and then captured on streptavidin-coated paramagnetic beads. A magnet is used to retrieve the paramagnetic beads from the solution, leaving nonhybridized ssDNA behind. Subsequently, the captured ssDNA target is released from the biotinylated oligonucleotide that remains attached to the para-magnetic beads. After release, the desired cDNA clone is further enriched by using a non-biotinylated target oligonucleotide to specifically prime conversion of the recovered ssDNA target to dsDNA. Following transformation and plating, typically, 20% to 100% of the colonies represent the cDNA clone of interest.

PAGE Purification of Oligonucleotides

Oligonucleotides contaminated by significant amounts of aborted synthesis products (e.g., n-1, n-2, n-3) will yield a high percentage of background colonies if used for cDNA capture and repair. To avoid this problem, gene-specific oligonucleotides, purified by gel purification on a denaturing acrylamide preparative gel (PAGE purification), were purchased from Life Technologies. The PAGE-purified oligonucleotide was diluted to 100 μM with TE buffer [10 mM Tris-HCl (pH 8.0), 1 mM EDTA). Approximately 2 to 5 OD ($A_{260}$) of oligonucleotide (33 ug=1 OD) was used and the total volume brought to 100 ul with TE buffer. 100 μl of phenol/chloroform/isoamyl alcohol (25:24:1), was added, vortexed thoroughly, and centrifuged at room temperature for 5 min at 14,000×g to separate the phases. About 90 μl of the upper, aqueous layer was removed transferred to a fresh 1.5-ml microcentrifuge tube. 45 μl of 7.5 M $NH_4OAc$ was added, followed by 350 μl of absolute ethanol (−20° C.). The mixture was vortexed thoroughly, stored on dry ice for 10 min, and centrifuged at 4° C. for 10 min at 14,000×g. The supernatant was removed carefully and the pellet overlayed with 100 μl of 70% ethanol (−20° C.), centrifuged for 2 min at 14,000×g and the supernatant removed. The oligonucleotide was dried at room temperature for 10 min, or until residual ethanol has been evaporated, and dissolved in 40 μl of TE buffer. The oligonucleotide concentration was determined by measuring $OD_{260}$. The oligonucleotide concentration should be greater than 0.5 μg/μl.

Biotinylation Reaction

Oligonucleotides were biotinylated using the following protocol:

TABLE 3

Biotinylation reaction conditions

| Component | Amount |
|---|---|
| 5 × TdT Buffer | 5 μl |
| oligonucleotide | 3 μg |
| Biotin-14-dCTP | 5 μl |
| autoclaved, distilled water | sufficient to bring the volume to 23 μl |
| TdT | 2 μl |

The components were added to a 1.5-ml microcentrifuge tube, vortexed gently and centrifuged for 2 s at 14,000×g. The tube was incubated for 1 h at 30° C. After 1 h, 1 μl of glycogen (20 μg/μl), 26 μl of 1 M Tris-HCl (pH 7.5), and 120 μl of ethanol were added to the oligonucleotide biotinylation reaction. The tube was vortexed and stored on dry ice for 10 min, then centrifuged at 4° C. for 30 min at 14,000×g. The supernatant was carefully and immediately removed from the microcentrifuge tubes and 200 μl of 70% ethanol (−20° C.) layered over the pellet before centrifuging at 4° C. for 2 min at 14,000×g. The ethanol wash was carefully removed from the microcentrifuge tubes. The ethanol wash was repeated once and the pellets dried at room temperature for 10 min or until completely dry. The biotinylated oligonucleotide was dissolved in 20 μl TE buffer. To determine the labeling efficiency and the concentration of the labeled oligonucleotide, 4 μl was removed for gel analysis and the remainder stored at −20° C.

Analysis of the Oligonucleotide Biotinylation Reaction Products

4 μl of formamide stop buffer was added to the 4 μl of biotinylated oligonucleotide. The tube was vortexed and centrifuged for 2 s at 14,000×g to collect the contents of the tube. The unbiotinylated oligonucleotide was diluted to 50 ng/ml, so that 4 μl contains 200 ng. 4 μl of the dilution was then mixed with 4 μl of formamide stop buffer. Samples were loaded with flat pipette tips onto a pre-poured 15% TBE-7 M Urea acrylamide/bisacrylamide gel (Catalog No. EC6885, NOVEX, San Diego, Calif.). The samples were separated by electrophoresis at 100 V for 1.5 h or until the blue dye migrates to the middle of the gel. The gel was stained in ethidium bromide solution (0.5 μg/ml) for 15 min. The gel was transferred to clear plastic wrap and photographed using transmitted ultraviolet light. The biotinylated products in each lane containing the desired oligonucleotide were compared with samples of titrated, unbiotinylated oligonucleotide in adjacent lanes. More than 80% of the oligonucleotides should be biotinylated, corresponding to 1–6 (predominantly 3–4) biotin residues per oligonucleotide.

GeneTrapper Protocol for Semi-solid Amplification of Plasmid cDNA Libraries

Semi-solid amplification of primary cDNA transformants minimizes representational biases that can occur during the expansion of plasmid cDNA libraries (Kriegler, M. (1990) Gene Transfer and Expression: A Laboratory Manual. Stockton Press, New York, N.Y.). Ordinarily unstable clones are stabilized however when the amplification is performed at 30° C. (Hanahan, D., Jessee, J., and Bloom, F. R. (1991) Plasmid Transformation of *Escherichia coli* and other Bacteria. Methods Enzymol. 204:63–113.).

A large stir bar and 1.35 g SeaPrep agarose (Catalog No. 50302, FMC Bioproducts, Rockland, Me.) are placed into each of four 500 ml autoclavable bottles and 450 ml of 2×LB added to each bottle. The bottles of 2×LB agarose are autoclaved for 30 minutes, cooled in a 37° C. water bath for ~2 hours until media reaches 37° C. and Ampicillin added to a concentration of 200 ug/ml. $4\times10^5$–$6\times10^5$ primary cDNA transformants (colonies from the original pSPORT1 brain library) are added to each bottle, and mixed thoroughly on a stir plate for 2 min. (The actual inoculation was calculated to be $5.4\times10^5$ primary human brain cDNA transformants.) The caps are tightened and the bottles are placed in an ice water bath (0° C.) such that the level of water in the bath is at the same level as the upper level of media in the bottle for 1 hour. The bottles are then removed from the ice bath, the caps loosened, and the bottles incubated at 30° C. without disturbance for 61.5 hours (40–45 hours recommended) in a gravity flow incubator. The contents of bottles were poured into centrifuge bottles and centrifuged at 8,000 rpm for 20 min at room temperature. The supernatent is discarded and the cells resuspended in a total volume of 50 ml 2×LB/12.5% Glycerol (175 ml 2×LB, 25 ml Glycerol (100%)). Two 100 μl aliquots were removed for plating, further analysis, and colony estimate. Cells can be filtered through sterile cheesecloth to remove agarose clumps if present. The final titer was $3.9\times10^6$ cfu per ul stock. The cells were subdivided into 100 ul, 1 ml, and ~10 ml aliquots and stored at −70° C. The frozen cells can be used to prepare DNA for GeneTrapper experiments or can be further amplified in liquid at 30° C. to obtain DNA. $2.5\times10^9$ cells per 100 ml growth medium are used for further expansion of the library.

Preparation of dsDNA from a Plasmid cDNA Library 100 ml of Terrific Broth containing 100 ug/ml ampicillin were inoculated with $2.5\times10^9$ cells from an amplified library in a 1-L side-baffled flask and the cells grown the cells to saturation at 30° C. Cell density is measured at $A_{590}$. Cells are diluted 1:10 to 1:20 when appropriate to ensure that the observed $A_{590}$ value is between 0.2 and 0.8. No more than 500 $OD_{590}$ units are processed at a given time. The sample is divided into two 50-ml centrifuge tubes and centrifuged at 4,800×g for 15 min at 4° C. The supernatant is poured off and the cell pellets resuspend in a total volume of 10 ml of buffer I with RNase (15 mM Tris-HCl (pH 8.0), 10 mM EDTA, RNase A (100 μg/ml), RNase T1 (1,200 units/ml)). 10 ml of freshly-prepared Buffer II (0.2 M NaOH, 1% SDS) was added to the resuspended cells, inverted gently to mix and incubated for 5 min at room temperature. 10 ml of cold 7.5 M $NH_4OAc$ was added to the cell mixture, gently inverted to mix and incubated on ice for 10 min. The sample was centrifuged at 3,000×g for 15 min at 4° C. and the supernatant poured through coffee filter into a fresh 50-ml centrifuge tube. The white flocculant material was avoided. An equal volume of cold isopropanol (−20° C.) was added, mixed well, and centrifuged at 3,000×g for 15 min at 4° C. The supernatant was discarded and the pellet resuspended in 1 ml of buffer I with RNase and transferred to a microcentrifuge tube. The solution was clarified by centrifugation at 4° C. for 1 min at 14,000×g and the supernatant transferred to a fresh microcentrifuge tube. The tube was incubated at 37° C. for 30 min, and at 65° C. for 5 min. The sample was then divided into two equal parts (~500 μl each) in 1.5-ml microcentrifuge tubes. An equal volume of phenol:chloroform:isoamyl alcohol (25:24:1) was added to each sample, vortexed, and centrifuged at room temperature for 5 min at 14,000×g. 450 μl of the upper aqueous phase was transferred to fresh microcentrifuge tubes. The phenol:chloroform:isoamyl alcohol extraction was repeated at least 3 times. An equal volume of isopropanol (−20° C.) was added to each tube and centrifuged at 4° C. for 15 min at 14,000×g. The supernatant was discarded. 500 μl of 70% ethanol was carefully added to each tube, and centrifuged at 4° C. for 5 min at 14,000×g. The supernatant was discarded and the pellet dried at room temperature for 10 min. The two pellets were dissolved in a total volume of 200 μl TE buffer. The concentration of the ds plasmid DNA library concentration should be ~1 μg/μl. The dsDNA is stored at −20° C.

Generation of ssDNA with Gene II and Exo III

The following components are added to a 1.5-ml microcentrifuge tube at room temperature for each hybridization reaction:

TABLE 4

Generation of ssDNA

| Component | Amount |
|---|---|
| 10 × Gene II Buffer | 4 μl |
| ds phagemid cDNA (~1 μg/μl) | 5 μg |
| autoclaved, distilled water | sufficient to bring the volume to 38 μl |

2 μl of Gene II was added to each tube, vortexed, and centrifuged at room temperature for 2 s at 14,000×g to collect the contents to the bottom of the tube, before incubating at 30° C. in a water bath for 25 min. The mixture is incubated at 65° C. for 5 min and immediately chilled on ice for 1 min. 2 μl of the mixture is transferred to a microcentrifuge tube containing 8 μl of TE buffer and 2 μl of gel loading dye. These samples are saved on ice for subsequent gel analysis. 4 μl of Exo III are added to the remaining 38 μl in each tube, vortexed, and centrifuged at room temperature for 2 s at 14,000×g. The samples are incubated at 37° C. for 60 min. An equal volume (40 μl) of phenol:chloroform:isoamyl alcohol (25:24:1) is added to each tube, vortexed thoroughly, and centrifuged at room temperature for 5 min at 14,000×g to separate the phases. 36 μl of the upper aqueous phase are transferred to a fresh 1.5-ml microcentrifuge tube. The ssDNA can be stored at 4° C. for several days. 2 μl of each sample are transferred to a microcentrifuge tube containing 8 μl of TE buffer and 2 μl of gel loading dye and stored on ice. The samples to be analyzed are separated by electrophoresis at 1.5 h at 80 V, or until the blue dye migrates 3–4 cm, on a 0.8% agarose gel containing 0.5 μg/ml ethidium bromide in 1×TAE buffer. 250 ng of the original ds phagemid DNA and 1 μg of 1 Kb DNA Ladder are loaded into separate lanes as a control and a molecular weight marker, respectively.

Analysis of Gene II and Exo III Digestion Products

The Gene II and Gene II-Exo III-treated samples are compared to the undigested ds phagemid DNA. More than 50% of the supercoiled DNA should be nicked by the Gene II protein and migrate as open-circle DNA (the slowly migrating band). The nicked form of ds phagemid DNA generated by Gene II treatment should be completely converted to the ssDNA after the Exo III digestion (migrates faster than supercoiled). If the dsDNA was converted to ssDNA, the cDNA Capture Hybridization step (described below) was followed.

Oligonucleotide Hybridization

The biotinylated oligonucleotide (e.g., MetAP-3 for1) 5'-AGGACGAATGTGGTAAAAAG-3' (SEQ ID NO: 23)

was diluted to 20 ng/μl (1:1 dilution) in TE buffer. The 4× Hybridization Buffer was incubated at 37° C. for 2 min, mixed well, and added to the remaining 34 μl of Gene II/Exo III-treated DNA. The DNA sample was mixed by pipetting up and down, denatured in a 95° C. water bath for 1 min and chilled immediately on ice for 1 min. 1 μl of diluted biotinylated oligonucleotide (MetAP-3 for 1) 5'-AGGACGAATGTGGTAAAAAG-3' (SEQ ID NO: 23)

(20 ng) was added to the denatured DNA and mixed by pipetting up and down with a pipette setting of 25 μl. The tube was incubated in a water bath or air incubator for 1 h at 37° C.

Streptavidin Bead Preparation

Streptavidin paramagnetic beads were prepared twenty min before the hybridization was complete. The beads were gently mixed by pipetting until the beads at the bottom were completely resuspended and 45 μl of the mixed beads transferred to the bottom of a microcentrifuge tube for each reaction. The tubes were inserted into the magnet and allowed to sit for 2 min. The supernatant was carefully removed from the tubes present in the magnetic tube holder and 100 μl of TE buffer immediately added to the beads. The tube was removed from the magnet and the beads gently resuspend by finger tapping or vortexing at the lowest setting. The tube was reinserted into the magnet for 2 min, and the supernatant removed again. The beads were resuspended in 30 μl of TE buffer and the tubes placed into a microcentrifuge tube rack.

cDNA Capture

The hybridization mixture was removed from a 37° C. water bath and centrifuged at room temperature for 2 s at 14,000×g. The prepared paramagnetic beads were pipetted into the mixture and gently mixed by pipetting. The suspension was incubated for 30 min at room temperature and gently mixed frequently (every 2 to 3 min) by finger tapping or gently vortexing at the lowest setting for 10 s to resuspend the beads. The tubes were reinserted into the magnet. After 2 min, the supernatent was removed and discarded. 100 μl of Wash Buffer was added to the beads and resuspended by finger tapping or gently vortexing at the lowest setting. The wash step was repeated two additional times. 100 μl of Wash Buffer was added to the beads and the beads resuspended gently by pipetting up and down. The solution was transferred to a clean tube. The tubes were inserted into the magnet for 5 min. The supernatent was remove and discarded. 100 μl of Wash Buffer was added to each tube and gently tapped or vortexed. The tubes were inserted into the magnet again for 5 min. The supernatent was removed and discarded and 20 ul of freshly-prepared 1× Elution buffer was added to the beads and mixed well by pipetting. The beads were incubated at room temperature for 5 min, tapping the beads for about 10 s every minute. The tube was inserted into the magnet for 5 min. The supernatant (containing the captured cDNA clone) was transferred and saved in a fresh tube. The beads were resuspended in 15 μl of TE buffer. The tube was inserted into the magnet for 5 min and the supernatent combined with the supernatent from the previous step. The tube containing the combined supernatants was inserted into the magnet for 10 min to remove any remaining paramagnetic beads and the supernatant transferred to a fresh microcentrifuge tube. To the supernatant (~35 μl), add 1 μl of Glycogen, 18 μl of 7.5 M $NH_4OAc$, and 135 μl of ethanol (−20° C.). The sample was mixed well and store on ice for 10 min or at 4° C. overnight. The sample was centrifuged at 4° C. for 30 min at 14,000×g. The supernatant was carefully removed from the small pellets and 100 μl of 70% ethanol added to each tube. The tubes were centrifuged at room temperature for 2 min at 14,000×g. The ethanol was removed and the pellets dried at room temperature for about 10 min. The pellets were dissolved in 5 μl of TE buffer and stored at 4° C.

Repair of Captured cDNA

A DNA primer/repair mix was prepared for each capture reaction using reagents in the following proportions:

TABLE 5

Reaction conditions for repair of captured cDNA

| Component | Amount |
|---|---|
| captured DNA | 5 μl |
| autoclaved, distilled water | 11 μl |
| 50 ng oligonucleotide (MAP3-F1, not biotinylated) | 1 μl |
| 10 mM dNTP Mix | 0.5 μl |
| 10 × Repair Buffer | 2 μl |
| Repair Enzyme | 0.5 μl |
| final volume | 20 μl |

The sample was mixed by pipetting and centrifuged at room temperature for 2 s at 14,000×g. The sample was incubated for a single cycle in a DNA thermal cycler: 90° C. denature step for 1 min, 55° C. annealing step for 30 s, 70° C. extension step for 15 min. The tubes were removed and centrifuged at room temperature for 2 s at 14,000×g. The repaired DNA is stored −20° C. until needed.

Transformation of Captured/Repaired DNA with ULTRAMAX DH5a-FT Cells

Frozen competent ULTRAMAX DH5a-FT *E. coli* cells were thawed on wet ice, mixed, and 100 ul aliquots dispensed into chilled polypropylene test tubes. 5 ul of each DNA sample were added to the cells, gently mixed with the cells, and incubated on ice for 30 min. The cells were heat-shocked for 45 s in a 42° C. water bath without shaking, and placed on ice for 2 min. 0.9 ml of room temperature S.O.C medium was added to each tube. The tube were shaken at 225 rpm (37° C.) for 1 h. 250 μl of the transformed cell mixture were plated on LB agar plates containing 100 μg/ml ampicillin. The plates were incubated overnight at 37° C.

Colony Hybridization to Identify Clones Containing for Full Length MetAP-3

Digoxigenin-labeled oligonucleotides were used as probes to screen recombinant bacterial libraries for specific DNA sequences. Briefly, bacterial colonies were transferred to a nylon membrane. Colonies were lysed by alkaline treatment and the denatured DNA was immobilized on the membrane. Proteinase K treatment was used to digest interfering proteins. Hybridization is carried out using a digoxigenin-labeled DNA, RNA, or oligonucleotide probe and colorimetric or chemiluminescent immunoassays are used to facilitate detection of hybridization products.

DIG-labeled probes were generated using PCR DIG Probe Synthesis Kit, Catalog #1636-090, Roche Molecular Biochemicals/Boehringer Mannheim, Indianapolis, Ind. Upstream and downstream gene-specific primers (e.g., GSP-F, GSP-R) at a concentration of 1–10 uM, and template DNAs diluted 1:100 (1–50 ng) are not provided in the kit. The following components are added to a sterile microcentrifuge tube placed on ice.

TABLE 6

Reaction conditions for preparing DIG-labeled probes

| Reagents | Volume | Final Concentration |
|---|---|---|
| $H_2O$ | variable | |
| PCR buffer without $MgCl_2$ (Vial 3 from kit) | 10 μl | 1 × (10 mM Tris-HCl, 50 mM KCl) |
| PCR DIG Probe Synthesis Mix (Vial 2 from kit) | 10 μl | 200 μM dNTP |
| Upstream Primer @ 10 μM | 2 μl | 0.2 μM of each primer |

TABLE 6-continued

Reaction conditions for preparing DIG-labeled probes

| Reagents | Volume | Final Concentration |
|---|---|---|
| DownstreamPrimer @ 10 μM | 2 μl | |
| Taq DNA Polymerase @ 5 U/μl (Vial 1 from kit) | 1.5 μl | 7.5 U/100 μl |
| Template DNA @ 1:100 (Previous MAP3) | 2 μl | |
| Total Volume | 100 μl | |

The reagents were mixed and centrifuged briefly to collect the sample at the bottom of the tube. The DNA was then amplified in a DNA thermal cycler using the following program: (1) denature at 94° C. for 2 min before the first cycle; (2) for 30 cycles (denature at 94° C. for 30 sec; anneal at 55° C. for 30 sec; extend at 72° C. for 1 min); and (3) complete the cycles with a single cycle at 72° C. for 7 min. An aliquot of each reaction mixture (10 μl) was analyzed by agarose gel electrophoresis to ensure that a specific band was amplified and was suitable as a probe for subsequent hybridization procedures.

TABLE 7

Solutions needed for DNA hybridization

| Solution | Description |
|---|---|
| Denaturation solution 1 | 0.5 N NaOH, 1.5 m NaCl |
| Neutralization solution 2 | 1.0 M Tris-HCl, pH 7.5; 1.5 M NaCl |
| 20 × SSC buffer | 3 M NaCl, 300 mM sodium citrate, pH 7.0 |
| 2 × SSC buffer | 0.3 mM NaCl, 30 mM sodium citrate, pH 7.0 |
| Proteinase K | 2 mg/ml Proteinase K in 2 × SSC buffer dilute Proteinase K (>600 U/ml, 14–22 mg/ml; 1 to 10 in 2 × SSC) |
| Prehybridization solution | DIG Easy Hyb |
| Hybridization solution | DIG-labeled probe, diluted in DIG Easy Hyb |
| 2 × Wash solution | 2 × SSC, containing 0.1% SDS |
| 0.5 × Wash solution | 0.5 × SSC, containing 0.1% SDS |

Two layers of Whatman 3MM filter paper are used for each different solution: denaturation solution, neutralization solution, and 2×SSC. Colonies on agarose plates were cooled to 4° C. for approx. 30 min. A membrane disc (Ø 82 mm) was placed onto the surface of each plate for about 1 min and the orientation of each membrane was appropriately marked. The membrane disc was carefully removed with tweezers and blotted briefly (colonies side up) on dry Whatman 3MM paper. The membrane discs (colonies side up) were placed on the prepared filter paper soaked with denaturation solution and incubated for 15 min. The membrane was blotted briefly on Whatman 3MM paper and placed (colonies side up) on the prepared filter paper soaked with neutralization solution for 15 min. The membrane was blotted briefly on Whatman 3MM paper and placed on filter paper soaked with 2×SSC for 10 min. The DNA was crosslinked to the membrane with UV-light or by baking at 80° C. for 2 hours.

Proteinase K Treatment

Membranes were placed in a clean sealable dish containing 0.5 ml of 2 mg/ml Proteinase K on each membrane disc (0.5 ml for the Ø 82 mm discs). The solution was distributed evenly, and incubated for 1 h at 37° C. Cellular and agar debris on the membranes were removed by wiping with paper towels soaked with 2×SSC.

Hybridization

Up to 3 membrane discs (Ø 82 mm) were placed in a roller bottle, containing 60 ml DIG Easy Hyb solution prewarmed to 42° C. The samples were pre-hybridized for 1 h in a hybridization oven at 42° C. The labeled probe (90 ul) was denatured (double-stranded probes only) by boiling for 10 min at 95–100° C. and rapidly cool on ice. The denatured probe was mixed with 20 ml DIG Easy Hyb solution per each roller bottle, prewarmed to hybridization temperature. The prehybridization solution was removed and discarded. The hybridization solution was added to the membranes and incubated overnight at 42° C. in hybridization oven. At the end of the hybridization, the hybridization solution was poured into a tube that can withstand freezing and boiling (e.g., a 50 ml polypropylene tube).

Stringency Washes

The membranes were washed twice for 5 min in ample 2×SSC, 0.1% SDS min at room temperature with gentle agitation. The membranes were then transferred to 0.5×SSC, 0.1% SDS and washed twice for 15 min at 68° C. with gentle agitation.

Detection of DIG-Labeled Nucleic Acids

A DIG Luminescent Detection Kit (Catalog No. 1363 514) and a DIG Wash and Block Buffer Set (Cat. No. 1585762), Roche Molecular Biochemicals/Boehringer Mannheim, Indianapolis, was used for the chemiluminescent detection of digoxigenin-labeled nucleic acids. Briefly, membranes are treated with Blocking Reagent to prevent nonspecific attraction of antibody to the membrane. Then, membranes are incubated with a dilution of Anti-Digoxigenin, Fab fragments, which are conjugated to alkaline phosphatase. In the third step, the membrane carrying the hybridized probe and bound antibody conjugate is reacted with a chemiluminescent substrate and exposed to X-ray film to record the chemiluminescent signal.

TABLE 8

Reagents needed for detection of digoxigenin-labeled nucleic acids

| Reagent | Description |
|---|---|
| Washing buffer (Bottle 1; dilute 1:10 with $H_2O$) | 100 mM maleic acid, 150 mM NaCl; pH 7.5 (+20° C.); 0.3% (v/v) Tween ® 20 |
| Maleic acid buffer (Bottle 2; dilute 1:10 with $H_2O$) | 100 mM maleic acid, 150 mM NaCl; pH 7.5 (+20° C.) |
| Blocking solution (Bottle 3; dilute 1:10 with 1 × Maleic acid buffer) | 1% (w/v) Blocking reagent for nucleic acid hybridization dissolved in Maleic acid buffer. Blocking solution is cloudy and should not be filtered. It is stable for at least two weeks when stored at +4° C., but must then be brought to room temperature before use. |
| Detection buffer (Bottle 4; dilute 1:10 with $H_2O$) | 100 mM Tris-HCl, 100 mM NaCl; pH 9.5 (+20° C.) |

Detection

All incubations were performed at room temperature in clean plastic trays. After the hybridization and post-hybridization stringency washes, the membrane was equilibrated in washing buffer for 1 min. The membrane was first blocked by gently agitating it in blocking solution for 30–60 min. Longer blocking times are acceptable. The blocking solution was discarded and the membrane incubated for 30 min in antibody solution containing a 1:10,000 dilution of Anti-Digoxigenin-AP antibody. The antibody solution was discarded and the membrane washed twice, 15 min per wash, in washing buffer. The washing buffer was poured off and the membrane equilibrated in detection buffer for 2 min. The membrane was placed between two sheets of acetate (plastic page protectors). Approximately 0.5 ml (per $cm^2$) of the chemiluminescent substrate, CSPD, was placed on top of the membrane, the top sheet replaced, and any bubbles removed. The filter was incubated for 5 min. The semi-dry membranes were sealed in a plastic bag and exposed Lumi-Film standard X-ray film.

Colony Selection

Positive colonies were selected by aligning the autoradiograph to the original LB+Amp plates from which the membranes lifts were generated. Colonies were picked with a sterile Pipet tip and used to inoculate small volumes of culture broth (3 ml LB+Amp 100 ug/ml) that were incubated overnight at 37° C. with shaking. Plasmid DNA was isolated from 1.5 ml cultures using Promega Wizard Plus Miniprep DNA Purification kits, Cat No. A7500, Promega Corporation, Madison, Wis. Plasmid DNAs were screened by restriction analysis and/or DNA sequencing using vector specific oligonucleotide primers.

fluorogenic probe. The assay allows the detection of target messages using two oligonucleotides and a DNA probe. The probe contains a fluorescent reporter at the 5' end and a fluorescent quencher at the 3' end. The fluorescent reporter is released during the exponential phase of PCR by the 5'-3' nuclease activity of Taq polymerase. An initial RT step is followed by 40 PCR cycles. Fluorescence is measured real-time during the extension phase of each PCR cycle.

TaqMan Primer/Probe Design and Optimization

TaqMan primers and probes were designed using Primer Express Software (P.E. Biosystems, Foster City, Calif.) based on the nucleotide sequences of MetAP-1, -2, and -3. Forward and reverse primers are unlabeled and oligonucleotide probes are labeled with FAM (reporter dye) at the 5' end and with TAMRA (quencher dye) at the 3' end.

<u>MetAP-1 primer set</u>

| | | |
|---|---|---|
| hmap1F1: | 5'- AAGCGGTCTGCTCAGTTTGAG - 3' | (SEQ ID NO: 35) |
| hmap1R1: | 5'- GGCCGTGCACTGTCAAGT - 3' | (SEQ ID NO: 36) |
| hmap1P1: | 5'- ACACCCTCCTGGTCACAGACACTGGC - 3' | (SEQ ID NO: 37) |

<u>MetAP-2 primer set</u>

| | | |
|---|---|---|
| hmap2F1: | 5'- GACCCTCCCTCAGTTCCAATATG - 3' | (SEQ ID NO: 38) |
| hmap2R1: | 5'- GTGGGTGGGTATTCGCATTC - 3' | (SEQ ID NO: 39) |
| hmap2P2: | 5'- ACCTGTATCCTAATGGTGTATTTCCCAAAGGACA - 3' | (SEQ ID NO: 40) |

<u>MetAP-3 primer set</u>

| | | |
|---|---|---|
| hmap3F1: | 5'- GGCATCATGCAAACGACAGT - 3' | (SEQ ID NO: 41) |
| hmap3R1: | 5'- ACTGCGCCGACCTTTGATT - 3' | (SEQ ID NO: 42) |
| hmap3P1: | 5'- AGAGCCAATCATCACGGAGGGATCC - 3' | (SEQ ID NO: 43) |

<u>MetAP-2b alternate primer set</u>

| | | |
|---|---|---|
| map2bF: | 5'- TTGGAAGACTGTTCACGCAAGT - 3' | (SEQ ID NO: 44) |
| map2bR: | 5'- GTCACCGGCATTGGGAGTAT - 3' | (SEQ ID NO: 45) |
| map2bP: | 5'- TGGATGTTCTCTCAATAATTGTGCTGCCCAT - 3' | (SEQ ID NO: 46) |

<u>MetAP-3b alternate primer set</u>

| | | |
|---|---|---|
| mp3bF: | 5'- AACGTGCTCTGTCATGGTATTCC - 3' | (SEQ ID NO: 47) |
| mp3bR: | 5'- AGCCATTGTAATAGACTGTGACATCAA - 3' | (SEQ ID NO: 48) |
| mp3bP: | 5'- ACAGTCGACCTCTTCAGGATGGAGATATTATCAAC - 3' | (SEQ ID NO: 49) |

<u>MetAP-3c alternate primer set</u>

| | | |
|---|---|---|
| mp3cF: | 5'- CATGGAGACACCTCTGAAACATTT - 3' | (SEQ ID NO: 50) |
| mp3cR: | 5'- CCTGGCAACCTCCACTAACTTT - 3' | (SEQ ID NO: 51) |
| mp3cP: | 5'- CACATTCGTCCTCATTGCCCACCA - 3' | (SEQ ID NO: 52) |

Example 4

Tissue Distribution of MetAP-1, MetAP-2, and MetAP-3 by TaqMan Analysis

Taqman is a PCR-based assay which achieves great specificity and sensitivity by introducing a dual-labeled All TaqMan primers and probes were synthesized by P.E. Biosystems (Foster City, Calif.). Primers were supplied lyophilized and reconstituted with RNase-free water (Sigma Company, St. Louis, Mo.). Primers were supplied already reconstituted at 100 $\mu$M. All TaqMan reactions were performed in a 25 $\mu$l volume using One-Step RT-PCR kits, PCR Core kits, MuLV reverse transcriptase and RNase inhibitor from P.E. Biosystems (Foster City, Calif.). Reactions were performed according to manufacturer's instructions and analyzed using the ABI 7700 Sequence Detector System and Sequence Detection Software from P.E. Biosystems.

HUVEC total RNA was isolated using the ABI 6700 High-Throughput Sample Preparation workstation according to manufacturer's instructions. The RNA was then DNase treated to remove trace amounts of contaminating genomic DNA by incubating with RNase-free DNase (Promega, Madison, Wis. or Roche Molecular Biochemicals, Indianapolis, Ind. or Life Technologies, Gaithersburg, Md.) for at least 15 minutes at 37BC. DNase was then removed by purification over RNeasy minispin columns according to manufacturer's instructions for RNA cleanup (Qiagen, Valencia, Calif.). RNA samples were quantitated by reading the absorbance at 260 nm on a Beckman D-40 Spectrophotometer (Irvine, Calif.).

Specificity for the primers/probe sets was determined using MetAP-1, MetAP-2, and MetAP-3 cDNAs which had been cloned into plasmids (Table 1). The following combinations were tested in TaqMan PCR reactions to demonstrate that the primer/probe sets worked and were specific for the cDNA they were designed for. Results are indicated as either "+" for positive reaction or "−" for little/negligible reaction.

TABLE 9

Primer pair sets used for TaqMan PCR reactions

| cDNA in plasmid | MetAP-1 primer/probe | MetAP-2 primer/probe | MetAP-3 primer/probe | MetAP-3b primer/probe | MetAP-3c primer/probe |
|---|---|---|---|---|---|
| MetAP1 | + | − | − | − | − |
| MetAP2 | − | + | − | − | − |
| MetAP3 | − | − | + | + | + |

The MetAP2b primer/probe set did not work well and was never tested for specificity. It was never used in subsequent assays.

Once specificity was demonstrated, the primer/probe sets were tested against HUVEC (human umbilical vein endothelial cells) total RNA to determine optimal assay conditions. Standard curves were set up using 200 ng, 40 ng, 8 ng, 1.6 ng and 0.32 ng HUVEC total RNA. One-step RT-PCR reactions were performed using forward and reverse primers (500 nM each final concentration) and probe (100 nM final concentration). These conditions were determined to be optimal for MetAP1, MetAP2 and MetAP3b and MetAP3c primer/probe sets. The original MetAP-3 primer/probe set was not as optimal as the others and was not used for further assays. The MetAP-3c primer/probe set was chosen for all subsequent assays to detect MetAP-3 expression levels.

Tissue Analysis Using TaqMan Technology

Human total brain RNA was obtained from Clontech (Palo Alto, Calif.) and DNase treated as described in Materials and Methods. Roughly 200 ng total RNA was used in duplicate TaqMan reactions to determine the relative message levels of MetAP-1, MetAP-2, and MetAP-3 in human brain samples. A TaqMan primer/probe set for human cyclophilin was used as an endogenous control to normalize for slight differences in the amounts of RNA assayed. Human cyclophilin is a housekeeping gene which was chosen as an endogenous control because message levels of that gene do not vary among tissue sources within a species or with differential treatment. The sequences of the human cyclophilin message primers and probes were as follows:

```
hcycmesF:
5'- CCCACCGTGTTCTTCGACAT - 3'      (SEQ ID NO: 53)

hcycmesR:
5'- TTTCTGCTGTCTTTGGGACCTT - 3'    (SEQ ID NO: 54)

hcycmesP:
5'- CGCGTCTCCTTTGAGCTGTTTGCA - 3'  (SEQ ID NO: 55)
```

The results indicated that 3-4 fold more MetAP-1 than MetAP-3 and 5-6 fold more MetAP-2 than MetAP-3 were found in human brain samples.

Relative expression levels of MetAP-1, MetAP-2, and MetAP-3 were also determined from polyA+ purified RNA from human brain and HUVEC cells (polyA$^+$ RNA obtained from Cindy Woods). 50 ng polyA$^+$ RNA was used in the assay and human cyclophilin was used as a normalizer.

The results indicated that in the human brain polyA$^+$ RNA samples there was roughly the same amount of MetAP-1 as MetAP-3, but 8-fold more MetAP-2 than MetAP-3. In HUVEC polyA$^+$ RNA samples, there was almost 6-fold more MetAP-1 than MetAP-3, and almost 10-fold more MetAP-2 than MetAP-3.

Additional sequencing of the MetAP-3 cDNA indicated that the original sequence used for TaqMan primer/probe design had one nucleotide difference in the region where the MetAP-3c probe annealed. A new MetAP-3c probe was reordered to be used in TaqMan reactions with the MetAP-3c forward and reverse primer. The sequence and name of that probe is below:

revmp3cP: 5'-CACATTCGTCCACATTGCCCACCA-3' (SEQ ID NO: 56)

This new probe was be used in all subsequent TaqMan reactions to determine MetAP3 expression levels.

Several tumor samples were also analyzed for MetAP-1, MetAP-2, and MetAP-3 expression levels. The following polyA$^+$ RNA samples were obtained from BioChain Institute, Inc. (San Leandro, Calif.):

3 colon cancer samples from different individuals 1 colon cancer sample and 1 adjacent normal colon sample from same individual 1 normal breast sample 1 breast cancer sample and 1 breast cancer from lymph node sample from same individual 1 metastatic colon cancer sample and 1 adjacent normal liver sample from same individual MetAP-3 Distribution in Various Human Tissues The reaction conditions and primers used to test the distribution of MetAP-3 in various human tissues are shown below and in Table 10.

Thermocycler: ABI 6700 Taqman robot.

Taqman Thermocycling Conditions:

48° C. 30'

95° C. 10'

95° C. 15"

60° C. 60"

Repeat 40 cycles

25° C. 2'

MetAP Tissue Distribution:

Primer/Probe Set for MetAP3:

mp3cF, mp3cR, revmp3cp

Primer/Probe Set for Human Cyclophilin:

mp3cF, mp3cR, revmp3cp

RNA: Total RNA from Clontech

Panels 1–5 with 6 tissues per panel

Reagents:
- 2× Master mix
  - AmpliTaq Gold
  - dNTPs with dUTP
  - ROX passive reference
  - PCR buffer
- 40× Master mix
  - MLV reverse transcriptase
  - RNase Inhibitor

TABLE 10

Reaction conditions for TaqMan PCR amplification with MetAP3 and cyclophilin primer pair sets

| Reaction: | Volume |
|---|---|
| Total RNA (16.7 ng/uL) | 6.0 uL |
| 2 × Master mix | 12.5 uL |
| 40 × Master mix | 0.675 uL |
| Probe (10 pmol/uL) | 0.25 uL |
| F Primer (100 uM) | 0.125 uL |
| R Primer (100 uM) | 0.125 uL |
| $H_2O$ | 5.3 uL |
| Total | 25 uL |

MetAP3 Distribution in Human Brain Tissue

The reaction conditions and primers used to test the distribution of MetAP-3 in various human tissues are shown below and in Table 11.

Primer/Probe Set for MetAP3:
- mp3cF, mp3cR, revmp3cp

Primer/Probe Set for Human Cyclophilin
- hcymesF, hcymesR, hcymesP

RNA: Poly(A)+ RNA from Clontech

Reagents:
- 2× Master mix
  - AmpliTaq Gold
  - dNTPs with dUTP
  - ROX passive reference
  - PCR buffer
- 40× Master mix
  - MLV reverse transcriptase
  - RNase Inhibitor

TABLE 11

Reaction conditions for Taqman PCR amplification to determine the distribution of MetAP3 RNAs in human brain tissues

| Reaction | Volume |
|---|---|
| Poly(A) RNA (2.5 ng/uL) | 8.0 uL |
| 2 × Master mix | 12.5 uL |
| 40 × Master mix | 0.675 uL |
| Probe (10 pmol/uL) | 0.25 uL |
| F Primer (100 uM) | 0.125 uL |
| R Primer (100 uM) | 0.125 uL |
| $H_20$ | 3.375 uL |
| | 25 uL |

Calculating Relative Expression Levels

Avg CT (PCR cycle): average of the CTs for replicates dCT: (Avg CT of Target−Avg. CT of control)

ddCT: (dCT of Target−dCT of Calibrator)

Relative Expression: $(1+E)^{ddCT}$ where E is the efficiency of amplification, assumed to be one.

20 ng poly$A^+$ RNA was used per TaqMan reaction and human cyclophilin was used as an endogenous control. To analyze the data, MetAP-1 was chosen as a calibrator and relative expression levels of MetAP-1 were set to "1." Levels of MetAP-2 and MetAP-3 were compared to the expression levels of MetAP-1 in each tissue.

The results indicated that in all tissues (both normal and tumor) levels of MetAP-2 ranged from 4- to 18-fold higher than levels of MetAP-1. Levels of MetAP-1 were roughly equivalent to levels of MetAP-3. No significant differences were observed in normal vs. tumor samples.

Example 5

High Throughput Methionine Aminopeptidase-2 (MetAP-2) Assay

A recombinant baculovirus stock harboring the human MetAP-2 gene which was capable of expressing the HA-tagged human MetAP-2 in cultured insect cells (Sf21) was obtained from Y-H. Chang, St. Louis University. Large (40 liter) bioreactors were used to scale up expression of the recombinant protein. The resulting cell paste which was clarified and solubilized for purification as described below.

The enzyme was partially purified according to the procedure of Li and Chang (*Biochem. Biophys. Res. Comm.* 227: 152–159, 1996). 16 g of cell paste was solubilized in 20 mM HEPES, 0.5 mM $CoCl_2$, 10% glycerol, pH 7.4. The resultant solution was centrifuged at 10,000×g for 10 min and subsequently filtered through a 0.45 μm filter to clarify. This solution was eluted from an S-sepharose column in the presence of a linear KCl gradient. The fumagillin-sensitive MetAP activity was pooled and used for enzyme analysis. This solution was approximately 30% pure by SDS-PAGE.

Unlabeled (cold) peptide substrate Met-Gly-Met-Met-Lys (SEQ ID NO: 67) was synthesized by American Peptide Co. (Sunnyvale, Calif.). A $^{14}C$-labeled, biotinylated version of the same peptide substrate, $^{14}C$-Met-Gly-Met-Met-Lys-(biotin) was prepared by American Radiolabeled Chemicals Inc. (St. Louis, Mo.). Sufficient unlabeled peptide was added to the reaction to result in a 0.1 mM final concentration. The starting enzyme assay contained 50–60,000 cpm per reaction.

The avidin capture beads were prepared by reacting avidin with Bio-Rad Affi-Gel® 10 Gel (Cat. 153-1000). The ImmunoPure® Avidin (#21128B) was purchased from Pierce. 500 mL of resin slurry was washed three times with excess cold Millipore water (18.2 megohm). The washed resin was slurried with 1 liter of cold 20 mM HEPES, 0.01% sodium azide, pH 7.5 buffer containing 5 g of ImmunoPure® Avidin. This solution was mixed continuously at 4° C. for 48 hrs. The beads were then allowed to settle and the supernatant was decanted. The avidin coated affi-gel was resuspended in 1 M glycine ethyl ester (Sigma #G-8001) pH 8.0 for two hours. The supernatant was decanted and the beads were washed three times with excess cold 20 mM HEPES, 0.01% sodium azide, pH 7.5 buffer. The avidin gel was finally suspended in 20 mM HEPES, 0.01% sodium azide, pH 7.5 buffer containing 2% Triton X-100 at a 2.6:1 ratio of buffer to the gel. This solution was stirred continuously during an enzyme experiment.

A typical MetAP reaction contains 0.1 mM

```
Met-Gly-Met-Met-Lys(biotin),      (SEQ ID NO: 67)
50-60,000 CPM of
```

$^{14}$C-Met-Gly-Met-Met-Lys(biotin), (SEQ ID NO: 67)
and 0.2–0.5 μg of partially purified MetAP-2. The reaction buffer contains 20 mM HEPES, 0.5 mM $CoCl_2$, 10% glycerol, pH 7.4. The reaction is initiated by the addition of substrate. The assay is mixed and allowed to stand, covered at room temperature for 30 min. MetAP-2 turnover is stopped by the addition of 150 μL of the avidin-affigel resin slurry. The slurry is thoroughly mixed with the reaction and allowed to settle for 10 min. 50 μL of the resultant supernatant containing the free $^{14}$C-methionine is transferred to a TopCount plate and 200 μL of Scint 40 is added. The results are then counted on a Packard TopCount counter.

MetAP1 and MetAP3 were assayed using the same procedure.

Example 6

Generation of Polyclonal Antibodies Recognizing Methionine Aminopeptidase Type 1, 2, and 3.

Immunoblotting was used to determine the level of expression and the distribution of MetAP-3 in various tissues. Antibodies specific for MetAP-1, MetAP-2, and MetAP-3, were first raised using peptides from various regions of these polypeptides.

Polyclonal antibodies against MetAP-1, MetAP-2, and MetAP-3 were generated by synthesizing peptides that correspond to amino acids 11–135 of AMPM_*Ecoli* (SEQ ID NO: 11). An N-terminal cysteine was used to facilitate conjugation to KLH. Peptides corresponding to amino acids 216–226 of AMPM_*Ecoli* (SEQ ID NO: 11), near the active site of this molecule, were synthesized and expected to block the activity the corresponding MetAP.

When the predicted amino acid sequence for human MetAP-3 was available from its cDNA sequence, two New Zealand white rabbits were immunized with different KLH-conjugated peptide antigens. Two synthetic peptides, $^{192}$SETFLVGNEDEAGKKLVEVA$^{211}$, designated MetAP3 peptide antigen-1, Ser Glu Thr Phe Leu Val Gly Asn Glu Asp Glu Ala Gly Lys Lys Leu Val Glu Val Ala (SEQ ID NO: 59)

and $^{291}$GSPEFKVLEDAWTVVSLDNQ$^{310}$, designated MetAP3 blocking peptide antigen, Gly Ser Pro Glu Phe Lys Val Leu Glu Asp Ala Trp Thr Val Val Ser Leu Asp Asn Gln (SEQ ID NO: 62)

were prepared by conventional solid phase methods.

A more thorough DNA sequence verification later revealed that the most 5' cDNA sequence coded for the peptide, $^{192}$SETFLVGN$\underline{V}$DE$\underline{C}$GKKLVEVA$^{211}$, designated MetAP3 peptide antigen-2, Ser Glu Thr Phe Leu Val Gly Asn Val Asp Glu Cys Gly Lys Lys Leu Val Glu Val Ala (SEQ ID NO: 63).

Similar approaches were used to obtain peptide-specific antibodies against MetAP-1 and MetAP-2. A listing of all the peptides used to raise antibodies against various methionine aminopeptidases is shown below.

```
MetAP1 peptide antigen
Asn Glu Thr Phe Phe Val Gly Glu Val Asp Asp Gly Ala Arg Lys Leu  (SEQ ID NO: 58)
 1               5                  10                  15

Val Gln Thr Thr
            20

MetAP2 peptide antigen
Cys Ala Phe Thr Val Thr Phe Asn Pro Lys Tyr Asp Thr Leu Leu Lys  (SEQ ID NO: 58)
 1               5                  10                  15

Ala Val Lys Asp
            20

MetAP3 peptide antigen-1
Ser Glu Thr Phe Leu Val Gly Asn Glu Asp Glu Ala Gly Lys Lys Leu  (SEQ ID NO: 59)
 1               5                  10                  15

Val Glu Val Ala
            20

MetAP1 blocking peptide antigen
Gly Trp Gln Asp Glu Thr Trp Pro Asp Gly Trp Thr Ala Val Thr Arg  (SEQ ID NO: 60)
 1               5                  10                  15

Asp Gly Lys Arg
            20
```

-continued

```
MetAP2 blocking peptide antigen
Cys Ser His Tyr Met Lys Asn Phe Asp Val Gly His Val Pro Ile Arg  (SEQ ID NO: 61)
 1              5                  10                  15

Leu Pro Arg Thr
            20

MetAP3 blocking peptide antigen
Gly Ser Pro Glu Phe Lys Val Leu Glu Asp Ala Trp Thr Val Val Ser  (SEQ ID NO: 62)
 1              5                  10                  15

Leu Asp Asn Gln
            20

MetAP3 peptide antigen-2
Ser Glu Thr Phe Leu Val Gly Asn Val Asp Glu Cys Gly Lys Lys Leu  (SEQ ID NO: 63)
 1               5                  10                  15

Val Glu Val Ala
            20
```

Polyclonal rabbit anti-MetAP-1, anti-MetAP-2, and anti-MetAP-3 antibodies were prepared by Covance using standard injection and immunization protocols supplied by the service provider. Western blotting, using total protein lysates from insect cells expressing recombinant hMetAP-1, hMetAP-2, and hMetAP-3 (see Example 8), was used to verify that the rabbit antisera directed against a MetAP-3 peptide specifically recognized human recombinant MetAP-3 only (data not shown).

The multiple human tissue blot was probed with the antiserum generated against the MetAP-3 $^{291}$GSPEFKVLEDAWTVVSLDNQ$^{310}$ peptide designated as the MetAP3 blocking peptide.

```
Gly Ser Pro Glu Phe Lys Val Leu Glu Asp Ala Trp Thr Val Val Ser  (SEQ ID NO: 62)
1              10                  15

Leu Asp Asn Gln
            20
```

The sub-cellular fraction specific blot generated from mouse liver was probed with the antiserum generated against the MetAP-3 $^{192}$SETFLVGNEDEAGKKLVEVA$^{211}$ peptide designated as the MetAP3 peptide antigen-1,

```
Ser Glu Thr Phe Leu Val Gly Asn Glu Asp Glu Ala Gly Lys Lys Leu  (SEQ ID NO: 59)
1               5                   10                  15

Val Glu Val Ala
            20
```

Example 7

Tissue and Subcellular Distribution of MetAP by Immunoblotting (Western Analysis)

Tissue or cell lysates were prepared by extraction with RIPA buffer (150 mM NaCl, 1% NP-40, 0.5% DOC, 0.1% SDS, 50 mM Tris-HCl, pH 7.5). SDS-PAGE was performed under reducing conditions employing the Tricine buffer system on 10% or 4–12% gradient polyacrylamide gels, transferred to nitrocellulose, then blocked in Blotto buffer (50 mM Tris-HCl pH 7.5, 100 mM NaCl, 4% powdered milk) overnight at 4° C. Membranes were incubated in hMetAP-3 antisera at a dilution of 1/2,000 for one hour at room temperature, washed with TBST (20 mM Tris-HCl pH 7.5, 500 mM NaCl, 0.1% Tween), followed by incubation with the secondary goat anti-rabbit peroxidase conjugated antibody (diluted 1/10,000). The HRP-labeled secondary antibody was detected using the Pico Western chemiluminescent protocol. Nonspecific immunoreactivity was detected by incubation of blots with the secondary conjugated antibody followed by chemiluminescent detection.

Western blot analysis of human MetAP-3 was used to determine the tissue distribution and the apparent molecular weight of the native human protein. As shown in FIG. 6B, MetAP-3 protein was most abundant in the testis, with moderate levels found in lung, kidney, ovary, heart, and spleen and very low levels were present in liver and brain. The native human protein migrates with an apparent molecular weight of 42,000 Da and unlike the human MetAP-2 protein that is highly glycosylated, MetAP-3 has only one consensus N-linked glycosylation site, which may explain the deviation from the 37,500 Da predicted molecular weight.

Example 8

Expression and Purification of Recombinant Human Methionine Aminopeptidases

Expression of MetAP-3 in Insect Cells

The baculovirus vectors pFastBac-1 and pFastBac-Hta (Life Technologies, Inc., Rockville, Md.) were used to generate recombinant baculoviruses expressing the MetAP-3 gene under the control of the polyhedrin promoter of the *Autographa californica* nuclear polyhedrosis virus. Briefly, the EcoRI/NotI PCR fragment encoding human MetAP-3 was ligated into pFastBac-1 and pFastBac-Hta (as described above). DNA isolated from bacterial colonies harboring plasmids were screened for inserts of the correct size (~1008 bp coding sequence plus flanking regions containing EcoRI and NotI recognition sites). Recombinant baculoviruses were generated by transposing the mini-Tn7 segment on the pFastBac donor plasmids to the attTn7 target (attachment) site on a baculovirus shuttle vector (bacmid) propagated in *E. coli* (Luckow et al., *J. Virol.* 67: 4566–4579 (1993)). The DNAs of composite bacmids harboring the polyhedrin promoter-MetAP3 gene cassette were isolated from bacteria and transfected into cultured *Spodoptera frugiperda* (Sf9) insect cells.

Stocks of recombinant baculoviruses expressing MetAP-3 were prepared, titered, and used to infect Sf9 cells under standard conditions (O'Reilly et al., *Baculovirus Expression Vectors: A Laboratory Manual*. New York, W.H. Freeman and Company (1992), and King and Possee, *The Baculovirus Expression System: A Laboratory Guide*, London, Chapman & Hall, (1992). The properties of recombinant proteins expressed in cultured insect cells by baculovirus vectors have been described and the general features of insect cell expression systems have been compared (See, e.g., V. A. Luckow, *Protein Eng*. J. L. Cleland., Wiley-Liss, New York, N.Y.: 183–2180 (1996) and references cited therein).

The majority of recombinant hMetAP-3 expressed in insect cells remained in the insoluble protein fraction when extracted with various buffers containing non-ionic detergents.

Expression of MetAP-3 in Bacteria

The coding region of hMetAP-3 was also cloned into the EcoRI/HindIII sites of the pET43a vector and expressed as a fusion protein containing the NusA bacterial protein and a histidine tag consisting of six consecutive histidine amino acids (6×His). A small linker region between the N-terminal NusA-6×His tag and the start of the human MetAP-3 coding region encodes a thrombin and enterokinase cleavage site. The hMetAP-3 containing pET43a vector was transfected into *E. coli* strain Tuner (DE3)plysS and grown at 37° C. in selection media (0.1 mM $CaCl_2$, 0.0005% vitamin B1, 0.2% glucose, 2 mM $MgSO_4$, 2×M9 salts, 2% casamino acids, and 100 ug/ml ampicillin) to a Klett Unit reading of 140. The expression of the hMetAP-3-Nus fusion protein was induced by addition of 0.5 mM IPTG for 4 hours at 25° C.

Bacteria expressing hMetAP-3 from a four-liter fermentation were pelleted and resuspended in 1500 mls of 50 mM Tris-HCl pH 8.5 containing 5 ml of protease inhibitor cocktail. The cell suspension was homogenized in a microfluidizer and centrifuged at 10,000×g. The supernatant containing the fusion protein was loaded onto a Q-Sepharose column (5.0×15 cm) pre-equilibrated with 50 mM Tris-HCl pH 8.5 and eluted with a gradient of 0–1 M NaCl. Fractions containing fusion protein, as determined by Western blot analysis using antibodies directed to the 6×His tag or hMetAP-3, were pooled and concentrated three-fold in a 76 mm stirred cell. The fusion protein was further purified using a Sephacryl S-100 column equilibrated with 50 mM Tris-HCl pH 8.5/100 mM NaCl. Fractions containing fusion protein were pooled from five consecutive runs. The pooled fractions were adjusted to pH 7.5 with 1 M Tris-HCl pH 6.8 and thrombin (10 U/mg protein) was added and incubated at 4° C. overnight. The solution was then dialyzed into 10 mM HEPES pH 7.5 and loaded onto a Mono S column (0.5×5 cm) equilibrated with 10 mM HEPES pH 7.5. The enzyme was eluted with a gradient of 0–1 M NaCl and fractions were analyzed for recombinant MetAP-3 protein content by Western blot analysis using polyclonal antisera directed against a human MetAP-3 peptide. Fractions were also analyzed for enzyme activity using the tripeptide MAS before they were pooled and stored at −20° C. for further analysis.

To increase the solubility of MetAP-3, the protein was expressed as a fusion protein tagged with an amino terminal histidine region and a NusA protein domain (Davis, G. D., Elisee, C., Newham, D. M., Harrison, R. G. (1999) *Biotechnol. Bioeng*. 65, 382–388). After solubilization of the *E. coli* cell pellet, the MetAP-3 fusion protein was found to reside primarily in the soluble fraction. Efforts to isolate the recombinant protein by immobilization on a Ni-NTA column were not successful, however, due to incomplete binding.

A more classical purification protocol involving anion exchange, size exclusion, and cation exchange chromatography was then pursued. The fusion protein was first concentrated using Q-Sepharose HP chromatography, followed by a Sephacryl S-100 HR resin, and then a final Mono S resin. Fractions containing fusion protein were identified by Western blot analysis using both anti-6×His tag and anti-MetAP-3 antibodies. Fractions were also monitored for enzyme activity by evaluating the release of methionine from an MAS tripeptide. A sharp peak of enzyme activity that corresponded with the absorbance was found in fractions 19–24 that were eluted from the Mono S column using a 0–1 M NaCl gradient (FIG. 7A). SDS-PAGE analysis followed by Coomassie staining revealed the enrichment of a 45 kDa protein in those fractions containing the highest specific activity for MetAP-3 (data not shown). Western blot analysis demonstrated that the majority of the NusA-6×His tag was removed by overnight thrombin cleavage (FIG. 7B; L, load lane) and that the MetAP-3 protein clearly resided in fractions 19–24. These fractions were pooled and characterized. Once completely cleaved by thrombin, the recombinant protein was predicted to contain a small 23 amino acid linker at the amino terminus that could account for a small increase in its apparent molecular weight. Amino terminal sequencing revealed the expected amino terminus for the thrombin-cleaved enzyme and the amino acid composition of the protein matched that predicted by its cDNA sequence (data not shown).

Expression of MetAP-1 and MetAP-2 in Insect Cells and in Bacteria

A cDNA for MetAP-1 was obtained by designing the MetAP-1 forward primer, 5'-ACTTGCATCAAGCTGGGCAT-3', (SEQ ID NO: 64) from the GeneBank clone (KIAA0094, accession # D42084) and using the GeneTrapper protocol with human skeletal muscle RNA serving as a cDNA template. A human MetAP-2 cDNA was obtained from Incyte (clone ID # 2744614) and the

```
MetAP-2 5' primer, 5'-CTAGAATTCATGGCGGGTGTGGAGGAGGTA-3', (SEQ ID NO: 65)
and the

MetAP-2 3' primer, 5'-TGCGGCCGCTTAATAGTCATCTCCTCTGCT-3', (SEQ ID NO: 66)
```

were designed to obtain the coding sequence by PCR. Both full-length cDNA clones were inserted into the FastBac-1 vector, expressed in Sf9 insect cells, and purified from the pellets of a forty-liter insect cell fermentation. Human MetAP-2 was purified by a previously published protocol (Liu, S., Widon, J., Kemp, C. W., Crews, C. M., and Clardy, J. (1998) *Science* 282, 1324–1327).

Human MetAP-1 was purified by resuspending the insect cell pellet in lysis buffer (50 mM HEPES, 150 mM NaCl, pH 7.4, containing 1 mM PMSF and protease inhibitor cocktail without EDTA) and exposing to liquid nitrogen at 900 psi pressure for 1 hour at 4° C. The lysate was centrifuged for 1 hour at 4° C. at 13,000 rpm and the supernatant was loaded onto a Q-Sepharose column (5×17 cm) pre-equilibrated with lysis buffer. The flow through from the Q-Sepharose column was adjusted to pH 7.4 and applied to a SP-Sepharose column (2.5×24 cm) pre-equilibrated with lysis buffer. Recombinant human MetAP-1 was eluted from the column with a gradient of 150–500 mM NaCl in lysis buffer. MetAP-1 eluted as a single peak at approximately 325 mM NaCl. Fractions containing MetAP-1 were pooled and dialyzed in 150 mM potassium phosphate (pH 7.0) overnight and then loaded on a hydroxyapatite column (1.6×15 cm) pre-equilibrated with dialysis buffer. MetAP-1 was eluted with a 150–480 mM phosphate gradient, pH 7.0. MetAP-1 eluted as a broad peak between 265–365 mM phosphate. Fractions containing MetAP-1 were pooled and dialyzed in 20 mM Tris-HCl (pH 7.5)/50 mM NaCl overnight at 4° C. The dialyzed MetAP-1 was then applied to an anion exchange High-Q resin (1.0×6.0 cm) pre-equilibrated with dialysis buffer. The MetAP-1 containing flow-through was collected and stored at −20° C. prior to enzyme analysis. SDS-PAGE followed by Coomassie staining or Western analysis demonstrated a single band at approximately 43 kDa (data not shown).

Example 9

Expression Analysis

To determine the mRNA size and tissue distribution of human MetAP-3, Northern analysis was performed using the complete 1,008 base pair coding region as a probe.

RNA Blotting Methods

Pre-made commercial Northern blots and hybridization solutions were used in this experiment. Each lane contained 2 ug of poly $A^+$ RNA from various human tissues. The membranes were first pre-hybridized for 4 hours at 68° C. in ExpressHyb solution. The 1,008 base pair coding sequence of the MetAP-3B was labeled by random prime Nick translation using [$^{32}$P]-dATP and the Random-Prime It II kit. Unincorporated nucleotides were separated from the probe using a NucTrap probe purification column. The radioactive probe was then denatured by boiling for 2 minutes and added to the blot at a concentration of $2\times10^6$ cpm/ml in fresh ExpressHyb solution. Hybridization was performed overnight at 68° C. The blots were washed twice in 2×SSC, 0.05% SDS for 30 minutes at room temperature, followed by two washes in 0.1×SSC, 0.1% SDS for 30 minutes at 50° C. After washing, the blots were exposed to X-ray film for 2 days at −80° C.

RNA Blotting (Northern Analysis)

As shown in FIG. 6A, a major band corresponding to a 3.62 kb message was most prevalent in skeletal muscle, testis, and prostate and a moderate level was also found in heart and kidney. A very low level of signal was detected in brain, colon, thymus, spleen, liver, lung, peripheral blood leukocytes, and uterus. These data suggest that the messenger RNA for human MetAP-3 contains a large 5' untranslated (500 bp) and 3' untranslated (2,100 bp) regions.

Example 10

Methionine Aminopeptidase Activity Assay

The activity of MetAP-1, MetAP-2, and MetAP-3 prepared from various sources was determined by measuring the release of methionine from several peptide substrates.

MetAP Assay Conditions

MetAP activity was indirectly measured by coupling the release of methionine from a tripeptide substrate (e.g., Met-Ala-Ser), to a reaction catalyzed by L-amino acid oxidase. Hydrogen peroxide, produced by the L-amino acid oxidase reaction, was measured by monitoring the formation of resorufin from Amplex Red in a reaction catalyzed by of horseradish peroxidase. Amplex Red was the peroxidase substrate, and resorufin was monitored by measuring its absorbance at 563 nm. The reaction was performed in a 96-well plate format at ambient temperature using the following assay buffer: 20 mM HEPES-Na pH 7.5, 100 mM NaCl, 0.1 mM $CoCl_2$ containing 100 μM Amplex Red, 0.15 U/ml L-amino acid oxidase, 0.5 U/ml horseradish peroxidase.

The tripeptide substrate concentration was varied from 2 μM to 50 mM to determine the $K_m$ and $V_{max}$ values by applying the Michaelis-Menten equation. The ability of fumagillin to inhibit each of the recombinant human MetAPs was determined by adding 0.6 nM–500 μM fumagillin at the start of the reaction. The $IC_{50}$ values were determined under conditions in which enzyme concentration and reaction time were linear.

Other tripeptides (MGG, GGG, IGG, and MEG) were also synthesized, purified by conventional methods, and evaluated for their ability to serve as substrates for MetAP-3 using the same conditions, as described above, for the MAS peptide.

Enzyme Activity

The ability of recombinant human MetAP-3 to cleave the N-terminal methionine from the synthetic tripeptide MAS was compared to recombinant hMetAP-1 and hMetAP-2 (Table 12A).

TABLE 12A

| Kinetic parameters and fumagillin-sensitivity of human MetAPs evaluated by monitoring hydrolysis of methionine from a MAS peptide substrate. | | | |
|---|---|---|---|
| | $k_{cat}$ ($s^{-1}$) | $K_m$ (mM) | Fumagillin $IC_{50}$ ($\mu$M) |
| MetAP-1 | 0.75 | 8.5 | 33 |
| MetAP-2 | 2.3 | 0.3 | 0.005 |
| MetAP-3 | 0.06 | 0.6 | >500 |

Recombinant human MetAP-3 was found to be an active methionine aminopeptidase that was not inhibited by fumagillin. MetAP-3 has an apparent $K_m$ of 0.6 mM for MAS, which was very close to that of human recombinant MetAP-2. MetAP-3 activity was resistant to fumagillin treatment, however, with an $IC_{50}$ value >500 $\mu$M. Recombinant human MetAP-2 and MetAP-1 have $IC_{50}$ values of 0.005 $\mu$M and 33 $\mu$M, respectively, in line with previous reports indicating that MetAP-2 is inhibited by fumagillin (Griffith, E. C., Su, Z., Turk, B. E., Chen, S., Chang, Y.-H., Wu, Z., Biemann, K., and Liu, J. O. (1997) Chem. Biol. 4, 461–471). The observed $k_{cat}$ for MetAP-3 was low compared to human MetAP-1 and MetAP-2. Alanine may not be a favored second amino acid, since the activity using MGG was twice as high that achieved using MAS as a substrate (Table 12B).

TABLE 12B

| The maximum velocity for recombinant human MetAP-3 was determined using various tripeptide substrates. | | |
|---|---|---|
| Peptide sequence | Cleaved | Vmax (Abs × 1000/min) |
| MAS | Yes | 70 |
| MGG | Yes | 134 |
| GGG | No | 0.7 |
| IGG | No | 3.1 |
| MEG | No | 1.1 |

MetAP-3 demonstrated the characteristics of a typical methionine aminopeptidase as seen by its substrate specificity listed in Table 12B. MGG was cleaved, while GGG and IGG were not, indicating that this enzyme was specific for methionine over other hydrophilic amino acids at the amino terminus. The fact that this enzyme cannot cleave MEG matches the specificities of the other two known methionine aminopeptidases, MetAP-1 and MetAP-2, since they also require the amino acid next to the methionine to be one of the seven small, uncharged residues (Ala, Cys, Gly, Pro, Ser, Thr, or Val) (Arfin, S. M., Kendall, R. L., Hall, L., Weaver, L. H., Stewart, A. E., Matthews, B. W., and Bradshaw, R. A. (1995) *Proc. Natl. Acad. Sci. USA* 92, 7714–7718).

Example 11

Mitochondrial Localization

The inability to extract native and insect cell expressed recombinant MetAP-3 protein by traditional methods suggested that the enzyme was associated with a cellular organelle or membrane. Analysis of the N-terminal amino acid sequence of the putative MetAP-3 by the MitoProt and TargetP programs (Emanuelsson, O., and von Heijne, G. (2001) *Biochim. Biophys. Acta* 1541, 114–119), indicated that the probability of mitochondrial import is 99% and 89%, respectively.

The localization of the native mouse MetAP-3 from normal liver in various subcellular components was determined by immunoblotting with anti-MetAP-3 antibodies (FIG. 8). As predicted, the MetAP-3 protein was clearly enriched in the mitochondrial fraction. The amount of MetAP-3 in the total liver protein extract is very low and could only be detected upon prolonged exposure. This was also true for the normal human liver protein extract that was profiled (FIG. 6B). The 45 kDa molecular weight size of mouse and human native mitochondrial MetAP-3 proteins evaluated by SDS-PAGE and Western blotting are very similar yet deviate only slightly from that predicted on the basis of their putative 335 amino acid sequence. Furthermore, higher levels of MetAP-3 mRNA and protein expression were found to correlate with those tissues containing abundant mitochondria (skeletal muscle, testis, and smooth muscle containing tissues [prostate and uterus] and cardiac muscle of the heart).

REFERENCES

Each of the references below is specifically incorporated herein in their entirety. These references can also be relied upon to make and use aspects of the invention.

Altschul, S. F., Gish, W., Miller, W., Myers, E. W. and Lipman, D. J. (1990) *J. Mol. Biol*., 215, 403–410.

Anfossi et al., *Proc. Natl. Acad. Sci.* (*U.S.A.*) 86:3379–3383 (1989)

Arfin, S. M., Kendall, R. L., Hall, L., Weaver, L. H., Stewart, A. E., Matthews, B. W., and Bradshaw, R. A. (1995) *Proc. Natl. Acad. Sci. USA* 92, 7714–7718

Armour, et al., *FEBS Lett.* 307:113–115 (1992)

Baldwin et al., *Gene Ther.* 4:1142–1149 (1997)

Barany, *Proc. Natl. Acad. Sci.* (*U.S.A.*) 88:189–193 (1991)

Bassat et al., *J. Bacteriol.* 169:751–757 (1987)

Baum et al., *J. Hematother.* 5: 323–329 (1996)

Becker et al., *EMBO J.* 8:3685–3691 (1989)

Ben-Bassat et al., *J. Bacteriol.* 169:751–757 (1987)

Berkner, *BioTechniques* 6:616–629 (1988)

Berkner, *Current Top. Microbiol. Immunol.* 158:39–66 (1992)

Blobel and Dobberstein, *J. Cell Biol.* 67:835–851 (1975)

Boris-Lawrie and Temin, *Annal. New York Acad. Sci.* 716:59–71 (1994)

Boris-Lawrie and Temin, *Curr. Opin. Genet. Dev.* 3:102–109 (1993)

Bostian et al., *Cell* 36:741–751 (1984)

Botstein et al., *Ann. J. Hum. Genet.* 32:314–331 (1980)

Bradshaw, R. A., Brickey, W. W., and Walker, K. W. (1998) *Trends Biochem. Sci.* 23, 263–7

Braun, H.-P. and Schmitz, U. K. (1993) *FEBS Lett* 316, 128–132

Bregni et al., *Blood* 80:1418–1422 (1992)

Brody and Crystal, *Annal. New York Acad. Sci.* 716:90–103 (1994)

Capecchi, *Cell* 22:479–488 (1980)

Castronovo, V., and Belotti, D. (1996) *Eur. J. Cancer* 32, 2520–2527

Chang, S. Y., McGary, E. C., and Chang, S. (1989) *J. Bacteriol.* 171, 4071–4072

Chen et al., *Gene Ther.* 5:50–58 (1998)

Clapp, *Clin. Perinatol.* 20:155–168 (1993)

Collins, In: Alternative Immunoassays, John Wiley & Sons, NY (1985)

Corbi and Lopez-Rodriguez, *Leuk. Lymphoma* 25:415–425 (1997)

Crabeel et al., *EMBO J.* 2:205–212 (1983)

Curiel et al., *Hum. Gen. Ther.* 3:147–154 (1992)

*Current Protocols in Molecular Biology*, John Wiley & Sons, N.Y. (1989)
Datta et al., *Proc. Natl. Acad. Sci. USA* 85: 3324–2238 1(1988)
Davis, G. D., Elisee, C., Newham, D. M., Harrison, R. G. (1999) *Biotechnol. Bioeng*. 65, 382–388
Derynck et al., *Nucleic Acids Res*. 11:1819–1837 (1983)
Dobson et al., *Nucleic Acids. Res*. 11:2287–2302 (1983)
Dunbar et al., *Blood* 85:3048–3057 (1995)
Dupuis, A., Skehel, J. Ml, and Walker, J. E. (1991) *Biochem. J*. 277, 11–15
Eglitis and Anderson, *Biotechniques*, 6:608–614 (1988)
El Bawab, S., Roddy, P., Qian, T., Bielawska, A., Lemasters, J. J., Hannun, Y. A. (2000) *J. Biol. Chem*. 275, 21508–21513
ELISA and Other Solid Phase Immunoassays (Kemeny, et al., Eds.), John Wiley & Sons, NY (1988)
Elshami et al., *Cancer Gene Ther*. 4:213–221 (1997)
Emanuelsson, O., and von Heijne, G. (2001) *Biochim. Biophys. Acta* 1541, 114–119
Fackrell, *Clin. Immunoassay* 8:213–219 (1985)
Farazi, T. A., Waksman, G., Gordon, J. I. (2001) *J. Biol. Chem*. 276, 39501–39504
Fearnley, I. M., Carroll, J., Shannon, R. J., Runswick, M. J., Walker, J. E., Hirst, J. (2001) *J. Biol. Chem*. 276, 38345–38348
Fernandez de Henestrosa et al., *FEMS Microbiol. Lett*. 147:209–213 (1997)
Frohman, M. A. et al., *Proc. Natl. Acad. Sci*. (*U.S.A.*) 85:8998–9002 (1988)
Fromm et al., *Nature* 319:791 (1986)
Fromm et al., *Proc. Natl. Acad. Sci*. (*U.S.A.*) 82:5824–5828 (1985)
Gäbler, L, Herz, U., Liddell, A., Leaver, C. J., Schröder, W., Brennicke, A., and Grohmann, L. (1994) *Mol. Gen. Genet*. 244, 33–40
Gerwirtz et al., *Science* 242:1303–1306 (1988)
Giglione, C., Serero, A, Pierre, M., Boisson, B., and Meinnel, T. (2000) *EMBO J*. 19, 5916–5929
Goff et al., *EMBO J*. 9: 2517–2522 (1990)
Goodchild et al., *Proc. Natl. Acad. Sci*. (*U.S.A.*) 85:5507–5511 (1988)
Graham and van der Eb, *Virology* 54:536–539 (1973)
Gray et al., *Proc. R. Acad. Soc. Lond*. 243:241–253 (1991)
Griffith, E. C., Su, Z., Turk, B. E., Chen, S., Chang, Y.-H., Wu, Z., Biemann, K., and Liu, J. O. (1997) *Chem. Biol*. 4, 461–471
Griffiths et al., *Biochem. J*. 241: 313–324 (1987)
Guarente and Ptashne, *Proc. Natl. Acad. Sci*. (*U.S.A.*) 78:2199–2203 (1981)
Gusella, *Ann. Rev. Biochem*. 55:831–854 (1986)
Hallek et al., *Cytokines Mol. Ther*. 2: 69–79 (1996)
Harley and Reynolds, *Nucleic Acids Res*. 15:2343–2361 (1987)
Harlow and Lane, *In Antibodies: A Laboratory Manual*, Cold Spring Harbor Press, Cold Spring Harbor, N.Y. (1988)
Harms and Splitter, *Hum. Gene Ther*. 6:1291–1297 (1995)
Hasan et al., *Gene* 56:141–151 (1987)
Hattori et al., *Genes Dev*. 6: 609–618 (1992)
Hawley and McClure, *Nucleic Acids Res*. 11:2237–2255 (1983)
Haymes, et al. Nucleic Acid Hybridization, A Practical Approach, IRL Press, Washington, D.C. (1985)
Hillel et al., *Anim. Genet*. 20:145–155 (1989)
Hillel et al., *Genet*. 124:783–789 (1990)
Hitzeman et al., *Nature* 293:717–722 (1981)
Holt et al., *Molec. Cell. Biol*. 8:963–973 (1988)
Ingber et al. *Nature* 348:555–557, (1990)
Janknecht et al., *Carcinogenesis* 16:443–450 (1995)
Janknecht *Immunobiology* 193:137–142 (1995)
Jefferson et al., *EMBO J*. 6: 3901–3907 (1987)
Jefferson *Plant Mol. Biol. Rep*. 5: 387–405 (1987)
Jeffreys et al., *Amer. J. Hum. Genet*. 39:11–24 (1986)
Jeffreys et al., *Anim. Genet*. 18:1–15 (1987)
Jeffreys et al., *Nature* 316:76–79 (1985)
Johnston and Tang, *Methods Cell Biol*. 43:353–365 (1994)
Jones et al., *Eur. J. Haematol*. 39:144–147 (1987)
Julius et al., *Cell* 32:839–852 (1983)
Julius et al., *Cell* 36:309–318 (1984)
Kaser, M., Langer, T. (2000) *Semin. Cell Dev. Biol*. 11, 181–90
Kendall and Bradshaw, *J. Biol. Chem*. 267:20667–20673 (1992)
King and Possee, The Baculovirus Expression System: A Laboratory Guide, London, Chapman & Hall
Kruger E. A., and Figg W. D. (2000) *Expert Opin. Investig. Drugs* 9, 1383–96
Kuijan and Herskowitz, *Cell* 30:933–943 (1982)
Kusaka et al., *Biochem. Biophys. Res. Commun*. 174:1070–1076 (1991)
Kwoh et al., *Proc. Natl. Acad. Sci*. (*U.S.A.*) 86:1173 (1989)
Laboratory Techniques and Biochemistry in Molecular Biology, by Work, et al., North Holland Publishing Company, NY (1978)
Landegren et al., *Science* 241:1077–1080 (1988)
Langer R. et al., *Chem. Tech*. 12:98 (1982)
Li and Chang, Biochem. *Biophys. Res. Comm*. 227: 152–159 (1989)
Li, X and Chang Y.-H. (1995) *Proc. Natl. Acad. Sci. USA* 92, 12357–12361
Liu, S., Widon, J., Kemp, C. W., Crews, C. M., and Clardy, J. (1998) *Science* 282, 1324–1327
Lorz et al., *Mol. Gen. Genet*. 199:178 (1985)
Lu et al., *J. Exp. Med*. 178:2089–2096 (1993)
Luckow et al., *J. Virol*. 67: 4566–4579 (1993)
Luckow Protein Eng. J. L. Cleland., Wiley-Liss, New York, N.Y.: 183–2180 (1996)
Maffey, L., Degand, H., and Boutry, M. (1997) *Mol Gen Genet* 254, 365–71
Marcotte et al., *Nature* 335:454–457 (1988)
Marsh, *Nucleic Acids Res*. 14:3603 (1986)
McCarty et al., *Cell* 66: 895–905 (1991)
McCowen et al., *Science* 113:202–203 (1951)
Miller *Current Top. Microbiol. Immunol*. 158:1–24 (1992)
Miller et al., *Proc. Natl. Acad. Sci*. (*U.S.A.*) 91:2473–2477 (1987)
Moore et al., *Genomics* 10:654–660 (1991)
Mori and Prager, *Leuk. Lymphoma* 26:421–433 (1997)
Mullis et al., *Cold Spring Harbor Symp. Quant. Biol*. 51:263–273 (1986)
Ngo et al., In: Enzyme Mediated Immunoassay, Plenum Press, NY (1985)
Nickerson et al., *Proc. Natl. Acad. Sci*. (*U.S.A.*) 87:8923–8927 (1990)
Norman et al., *Vaccine* 15:801–803 (1997)
Nussbaumer et al., *FEMS Microbiol. Lett*. 118:57–63 (1994)
O'Neill et al., *Transplant Proc*. 23:2862–2866 (1991)
Obukowicz et al., *Applied Environmental Microbiology* 58:1511–1523 (1992)
Ohara et al., *Proc. Natl. Acad. Sci*. (*U.S.A.*) 86:5673–5677 (1989)
O'Reilly et al., Baculovirus Expression Vectors: A Laboratory Manual. New York, W.H. Freeman and Company (1992)

Ow et al., *Science* 234: 856–859 (1986)
Peseckis et al., *J. Biol. Chem.* 267:5107–5114 (1993)
Potrykus et al., *Mol. Gen. Genet.* 205:193–200 (1986)
Rachal et al., *EXS* 64:330–342 (1993)
Ray et al., *Adv. Exp. Med. Biol.* 280:107–111 (1990)
Remington's Pharmaceutical Sciences, 16th ed., Osol, Ed., Mack, Easton Pa. (1980)
Roderick and Matthews, *Biochemistry* 32:3907–3912 (1993)
Romanos et al., *Yeast* 8:423–488 (1992)
Rose et al., *Proc. Natl. Acad. Sci.* (*U.S.A.*) 78:2460–2464 (1981)
Rothman and Orci, *Nature* 355:409–415 (1992)
Sambrook et al., Molecular Cloning, A Laboratory Manual, 2nd Ed., Cold Spring Harbor Press, Cold Spring Harbor, N.Y. (1989)
Schmidt, J., Herfurth, E., Subramanian, A. R. (1992) *Plant. Mol. Biol.* 20, 459–65
Serfing et al., *Biochim. Biophys. Acta* 1263:181–200 (1995)
Shannon et al., *Crit. Rev. Immunol.* 17:301–323 (1997)
Sidman U. et al., *Biopolymers* 22:547 (1983)
Sin, N., Meng, L., Wang, M. Q. W., Wen, J. J., Bornmann, W. G., and Crews, C. M. (1997) *Proc. Natl. Acad. Sci. USA* 94, 6099–6103
Skolnick, M. H. et al., *Cytogen. Cell Genet.* 32:58–67 (1982)
Solbiati, J., Chapman-Smith, A., Miller, J. L., Miller, C. G., Cronan, J. E. (1999) *J. Mol. Biol.* 290, 607–614
Suh et al., *Gene* 169:17–23 (1996)
Sun et al., *Curr. Top. Microbiol. Immunol* 211:173–187 (1996)
Sutcliffe et al., *Proc. Natl. Acad. Sci.* (*U.S.A.*) 75: 3737–3741 (1978)
Takai et al., *Princess Takamatsu Symp.* 22:197–204 (1991)
Taylor, A. B., Smith, B. S., Kitada, S., Kojima, K., Miyaura, H., Otwinowski, Z., Ito, A., and Deisenhofer, J. (2001) *Structure* 9, 615–625
Termignoni, C., Freitas, J. O., and Guimarães (1991) *Mol. Cell. Biochem.* 102, 101–113.
Tong et al., *Anticancer Res.* 18:719–725 (1998)
Tuite et al., *EMBO J.* 1:603–608 (1982)
Uchimiya et al., *Mol. Gen. Genet.* 204:204 (1986)
Valenzuela et al., *Nature* 298:347–350 (1982)
Vassilev, A. O, Plesofsk-Vig, N, and Brambl, R. (1995) *Proc. Natl. Acad. Sci. USA* 92, 8680–8684
Wagner et al., *Proc. Natl. Acad. Sci.* (*U.S.A.*) 89:6099–6103 (1992)
Walker, J. E., Arizmendi, J. M., Dupuis, A., Ferarnley, I. M., Finel, M., Medd, S. M., Pilkington, S. J., Runswick, M. J., and Skehel, J. M. (1992) *J. Mol. Biol.* 226, 1051–1072
Weinberg et al., *Gene* 126:25–33 (1993)
Weisemann et al., *Biochimie* 73: 457–470 (1991)
Wickstrom et al., *Proc. Natl. Acad. Sci.* (*U.S.A.*) 85:1028–1032 (1988)
Wong and Neumann *Biochem. Biophys. Res. Commun.* 107:584–587 (1982)
Wu et al., *Genomics* 4:560 (1989)
Wu, S., Gupta, S., Chatterjee, N., Hileman, R. E., Kinzy, T. G., Denslow, N. D., Merrick, W. C., Chakrabarti, D., Osterman, J. C., and Gupta N. K. (1993) *J. Biol. Chem.* 268, 10796–81
Yanish-Perron et al. *Gene* 33:103–119 (1985)
Yolken *Rev. Infect. Dis.* 4:35 (1982)
Zamechik et al., *Proc. Natl. Acad. Sci.* (*U.S.A.*) 83:4143–4146 (1986)

We claim:

1. A purified and isolated polypeptide comprising the amino acid sequence of SEQ ID NO:8.

2. A purified and isolated polypeptide of claim 1 having the amino acid sequence of SEQ ID NO:8.

3. A recombinant polypeptide comprising the amino acid sequence of SEQ ID NO:8.

4. A recombinant polypeptide of claim 3 having the amino acid sequence of SEQ ID NO:8.

5. A composition consisting essentially of a buffer and a polypeptide selected from the group consisting of:

(a) a polypeptide having the amino acid sequence of SEQ ID NO:8; and (b) a polypeptide comprising the amino acid sequence set forth in SEQ ID NO:8.

* * * * *

SEQUENCE LISTING

```
<160> NUMBER OF SEQ ID NOS: 69

<210> SEQ ID NO 1
<211> LENGTH: 2671
<212> TYPE: DNA
<213> ORGANISM: homo sapiens MetAP1

<400> SEQUENCE: 1

ggcgctcttc cagcgggcag gcagcatggc ggccgtggag acgcgggtgt gcgagacaga     60

cggctgcagc agtgaggcca agctccagtg tcccacttgc atcaagctgg gcatccaggg    120

ctcgtacttc tgctcgcagg aatgttttaa aggaagttgg gctactcaca agttactaca    180

taagaaagca aaagatgaaa aggcgaagcg agaagtgtct tcctggactg tggaaggtga    240

tattaatact gacccatggg caggttatcg atatactggt aaactcagac cacattatcc    300

actgatgcca acaaggccag tgccaagtta tattcaaaga ccagattatg ctgatcatcc    360

cttaggaatg tctgaatctg aacaggctct taaaggtact tctcagatta aattactctc    420

atctgaagat atagaaggga tgcgacttgt atgtaggctt gctagagaag ttttggatgt    480

tgctgccggc atgattaaac caggtgtaac tactgaagaa atagatcacg ctgtacactt    540

agcatgtatt gcaagaaatt gctacccttc tcccctgaat tattataatt tcccaaagtc    600

ttgttgtacc tcagtgaatg aagtcatttg ccatggaata ccagacagaa ggcccttaca    660

agaaggtgac attgttaatg tggatatcac tctttatcgc aatggttatc atggggacct    720

gaatgagaca tttttttgttg gagaagtgga tgatggagca cggaaacttg ttcagaccac    780
```

-continued

```
atatgagtgc ctgatgcaag ccattgatgc agtgaagcct ggtgttcggt acagagaatt    840

gggaaacatt atccagaagc atgcccaagc aaatgggttt tcagttgttc gaagctattg    900

tgggcatgga atccacaagc tttttcatac agctcccaat gtaccccact atgctaaaaa    960

taaagcagtt ggagtgatga agtcgggcca tgtatttaca attgagccaa tgatttgtga   1020

aggcggatgg caggatgaaa cctggccaga tggttggact gcggtgacaa gagacggaaa   1080

gcggtctgct cagtttgagc acaccctcct ggtcacagac actggctgtg aaatcctaac   1140

ccggcgactt gacagtgcac ggcctcactt catgtctcaa ttttaatttc tcccaagatg   1200

gcacatctca gtaccttctt actgtgctat gcattttatt gagagtacag aaaggaagag   1260

gaaccttttt ttaatcactt gttttgtttt gactatagat aagaaaggac tacagcattt   1320

gatgtgtgtc ctcaagaact tgtcttgggt ctgaaaaagc tgagaagaat aaaggaaaca   1380

ttgctcaact cttcagcccc ctccccctgc acacctgttt tctcatttgc cctttgagca   1440

cttttactta aacttgcttg tagttgcttt tatcactgcc gcaaaaacagc catcaagagc  1500

catctgcttt ccaggtgaac attggaaatg agaatctttg aaacttagca atatgtgttg   1560

caccagattt tttaaattat atatatggaa atatatatgt atacatttta agttctgtat   1620

acataattac caaacactat gtgacctgga gtttgtgttg tttctgctct gacaggttta   1680

tatgttctta caaatggatc catagtttgc agtgatttaa ttcctggttg ggatttggcc   1740

tcccctctcc cccatgctaa ttatttaccc ttgtaattgt gcatagggaa gcactcaccc   1800

aatgagactt tctccaatgt ggactctgtg tgtcagtgaa tgaatgtagt aaaattcact   1860

ttggaaggtt atcaggcttt taaaaatcta gtttatggca aaaatagcca ttttccaagt   1920

ggtggctgac tgttgcaggg aatgagaatt tcataataca ctgctatttc agacctctgt   1980

ttggtcagaa atggaaaaga aaaagccccc tttcttccct tttctgtttt acttcaaggg   2040

cataccttgg aggtgctcag agaagcgtga agtttgcact atggtggagg atggggaaag   2100

agttctaaag tgtctccagc tgtgaaccca ggaggtcaag tgggctatta aaatctaacg   2160

ttgagtaaat gtgatagtga tgagaaagga attttgtgta ctgtaacctt gcagtagaga   2220

tgcagctgtc cttcgtgtgt ggaaacacac ctctccttta catagttggg aacctcatta   2280

gaaatgacct cagctgcccc atatctacgt tcctttcagc agttgtccaa gtaggagtgt   2340

atccagtgaa gacatatcaa atcacaaagt cattgtcatt agagtgtact tgattactgg   2400

gcatccttgt aatataattt cataccactg acacattata cttgtaagag aacatctttc   2460

ccagagtgcc tcagacctta ttgctttaaa atataataat gttttcatta cttttattat   2520

ttgaatgatt tagtaaagtt gactgaatct ggtatagact ttgggagtat gtgtgtgaag   2580

tttttatcaa actgtaatat ttgtgaatgg aatgccttgc aatatgaatg ttaatataat   2640

gtgtaaaggg agattaaaaa gtttgaatga t                                  2671
```

<210> SEQ ID NO 2
<211> LENGTH: 394
<212> TYPE: PRT
<213> ORGANISM: homo sapiens MetAP1

<400> SEQUENCE: 2

```
Ala Leu Phe Gln Arg Ala Gly Ser Met Ala Ala Val Glu Thr Arg Val
 1               5                  10                  15

Cys Glu Thr Asp Gly Cys Ser Ser Glu Ala Lys Leu Gln Cys Pro Thr
            20                  25                  30

Cys Ile Lys Leu Gly Ile Gln Gly Ser Tyr Phe Cys Ser Gln Glu Cys
```

-continued

```
        35                  40                  45

Phe Lys Gly Ser Trp Ala Thr His Lys Leu Leu His Lys Lys Ala Lys
    50                  55                  60

Asp Glu Lys Ala Lys Arg Glu Val Ser Ser Trp Thr Val Glu Gly Asp
65                  70                  75                  80

Ile Asn Thr Asp Pro Trp Ala Gly Tyr Arg Tyr Thr Gly Lys Leu Arg
                85                  90                  95

Pro His Tyr Pro Leu Met Pro Thr Arg Pro Val Pro Ser Tyr Ile Gln
            100                 105                 110

Arg Pro Asp Tyr Ala Asp His Pro Leu Gly Met Ser Glu Ser Glu Gln
        115                 120                 125

Ala Leu Lys Gly Thr Ser Gln Ile Lys Leu Leu Ser Ser Glu Asp Ile
    130                 135                 140

Glu Gly Met Arg Leu Val Cys Arg Leu Ala Arg Glu Val Leu Asp Val
145                 150                 155                 160

Ala Ala Gly Met Ile Lys Pro Gly Val Thr Thr Glu Glu Ile Asp His
                165                 170                 175

Ala Val His Leu Ala Cys Ile Ala Arg Asn Cys Tyr Pro Ser Pro Leu
            180                 185                 190

Asn Tyr Tyr Asn Phe Pro Lys Ser Cys Cys Thr Ser Val Asn Glu Val
        195                 200                 205

Ile Cys His Gly Ile Pro Asp Arg Arg Pro Leu Gln Glu Gly Asp Ile
    210                 215                 220

Val Asn Val Asp Ile Thr Leu Tyr Arg Asn Gly Tyr His Gly Asp Leu
225                 230                 235                 240

Asn Glu Thr Phe Phe Val Gly Glu Val Asp Asp Gly Ala Arg Lys Leu
                245                 250                 255

Val Gln Thr Thr Tyr Glu Cys Leu Met Gln Ala Ile Asp Ala Val Lys
            260                 265                 270

Pro Gly Val Arg Tyr Arg Glu Leu Gly Asn Ile Ile Gln Lys His Ala
        275                 280                 285

Gln Ala Asn Gly Phe Ser Val Val Arg Ser Tyr Cys Gly His Gly Ile
    290                 295                 300

His Lys Leu Phe His Thr Ala Pro Asn Val Pro His Tyr Ala Lys Asn
305                 310                 315                 320

Lys Ala Val Gly Val Met Lys Ser Gly His Val Phe Thr Ile Glu Pro
                325                 330                 335

Met Ile Cys Glu Gly Gly Trp Gln Asp Glu Thr Trp Pro Asp Gly Trp
            340                 345                 350

Thr Ala Val Thr Arg Asp Gly Lys Arg Ser Ala Gln Phe Glu His Thr
        355                 360                 365

Leu Leu Val Thr Asp Thr Gly Cys Glu Ile Leu Thr Arg Arg Leu Asp
    370                 375                 380

Ser Ala Arg Pro His Phe Met Ser Gln Phe
385                 390
```

<210> SEQ ID NO 3
<211> LENGTH: 1908
<212> TYPE: DNA
<213> ORGANISM: homo sapiens MetAP2

<400> SEQUENCE: 3

```
ctctgtctca ttccctcgcg ctctctcggg caacatggcg ggtgtggagg aggtagcggc      60

ctccgggagc cacctgaatg gcgacctgga tccagacgac agggaagaag gagctgcctc     120
```

-continued

```
tacggctgag gaagcagcca agaaaaaaag acgaaagaag aagaagagca aagggccttc    180
tgcagcaggg gaacaggaac ctgataaaga atcaggagcc tcagtggatg aagtagcaag    240
acagttggaa agatcagcat tggaagataa agaaagagat gaagatgatg aagatggaga    300
tggcgatgga gatggagcaa ctggaaagaa gaagaaaaag aagaagaaga agagaggacc    360
aaaagttcaa acagaccctc cctcagttcc aatatgtgac ctgtatccta atggtgtatt    420
tcccaaagga caagaatgcg aatacccacc cacacaagat gggcgaacag ctgcttggag    480
aactacaagt gaagaaaaga aagcattaga tcaggcaagt gaagagattt ggaatgattt    540
tcgagaagct gcagaagcac atcgacaagt tagaaaatac gtaatgagct ggatcaagcc    600
tgggatgaca atgatagaaa tctgtgaaaa gttggaagac tgttcacgca agttaataaa    660
agagaatgga ttaaatgcag gcctggcatt tcctactgga tgttctctca ataattgtgc    720
tgcccattat actcccaatg ccggtgacac aacagtatta cagtatgatg acatctgtaa    780
aatagacttt ggaacacata taagtggtag gattattgac tgtgctttta ctgtcacttt    840
taatcccaaa tatgatacgt tattaaaagc tgtaaaagat gctactaaca ctggaataaa    900
gtgtgctgga attgatgttc gtctgtgtga tgttggtgag gccatccaag aagttatgga    960
gtcctatgaa gttgaaatag atgggaagac atatcaagtg aaaccaatcc gtaatctaaa   1020
tggacattca attgggcaat atagaataca tgctggaaaa acagtgccga ttgtgaaagg   1080
aggggaggca acaagaatgg aggaaggaga agtatatgca attgaaacct ttggtagtac   1140
aggaaaaggt gttgttcatg atgatatgga atgttcacat tacatgaaaa attttgatgt   1200
tggacatgtg ccaataaggc ttccaagaac aaaacacttg ttaaatgtca tcaatgaaaa   1260
ctttggaacc cttgccttct gccgcagatg gctggatcgc ttgggagaaa gtaaatactt   1320
gatggctctg aagaatctgt gtgacttggg cattgtagat ccatatccac cattatgtga   1380
cattaaagga tcatatacag cgcaatttga acataccatc ctgttgcgtc caacatgtaa   1440
agaagttgtc agcagaggag atgactatta aacttagtcc aaagccacct caacaccttt   1500
attttctgag ctttgttgga aaacatgata ccagaattaa tttgccacat gttgtctgtt   1560
ttaacagtgg acccatgtaa tacttttatc catgtttaaa aagaaggaat ttggacaaag   1620
gcaaaccgtc taatgtaatt aaccaacgaa aaagctttcc ggacttttaa atgctaactg   1680
tttttcccct tcctgtctag gaaaatgcta taaagctcaa attagttagg aatgacttat   1740
acgttttgtt ttgaatacct aagagatact tttggatat ttatattgcc atattcttac    1800
ttgaatgctt tgaatgacta catccagttc tgcacctata ccctctggtg ttgcttttta   1860
accttcctgg aatccatttc taaaaaataa agacattttc agatctga                1908
```

<210> SEQ ID NO 4
<211> LENGTH: 478
<212> TYPE: PRT
<213> ORGANISM: homo sapiens MetAP2

<400> SEQUENCE: 4

```
Met Ala Gly Val Glu Glu Val Ala Ala Ser Gly Ser His Leu Asn Gly
 1               5                  10                  15

Asp Leu Asp Pro Asp Asp Arg Glu Glu Gly Ala Ala Ser Thr Ala Glu
            20                  25                  30

Glu Ala Ala Lys Lys Lys Arg Arg Lys Lys Lys Lys Ser Lys Gly Pro
        35                  40                  45

Ser Ala Ala Gly Glu Gln Glu Pro Asp Lys Glu Ser Gly Ala Ser Val
```

-continued

```
    50                  55                  60

Asp Glu Val Ala Arg Gln Leu Glu Arg Ser Ala Leu Glu Asp Lys Glu
65                  70                  75                  80

Arg Asp Glu Asp Asp Glu Asp Gly Asp Gly Asp Gly Asp Gly Ala Thr
                85                  90                  95

Gly Lys Lys Lys Lys Lys Lys Lys Lys Lys Arg Gly Pro Lys Val Gln
            100                 105                 110

Thr Asp Pro Pro Ser Val Pro Ile Cys Asp Leu Tyr Pro Asn Gly Val
        115                 120                 125

Phe Pro Lys Gly Gln Glu Cys Glu Tyr Pro Pro Thr Gln Asp Gly Arg
    130                 135                 140

Thr Ala Ala Trp Arg Thr Thr Ser Glu Glu Lys Lys Ala Leu Asp Gln
145                 150                 155                 160

Ala Ser Glu Glu Ile Trp Asn Asp Phe Arg Glu Ala Ala Glu Ala His
                165                 170                 175

Arg Gln Val Arg Lys Tyr Val Met Ser Trp Ile Lys Pro Gly Met Thr
            180                 185                 190

Met Ile Glu Ile Cys Glu Lys Leu Glu Asp Cys Ser Arg Lys Leu Ile
        195                 200                 205

Lys Glu Asn Gly Leu Asn Ala Gly Leu Ala Phe Pro Thr Gly Cys Ser
    210                 215                 220

Leu Asn Asn Cys Ala Ala His Tyr Thr Pro Asn Ala Gly Asp Thr Thr
225                 230                 235                 240

Val Leu Gln Tyr Asp Asp Ile Cys Lys Ile Asp Phe Gly Thr His Ile
                245                 250                 255

Ser Gly Arg Ile Ile Asp Cys Ala Phe Thr Val Thr Phe Asn Pro Lys
            260                 265                 270

Tyr Asp Thr Leu Leu Lys Ala Val Lys Asp Ala Thr Asn Thr Gly Ile
        275                 280                 285

Lys Cys Ala Gly Ile Asp Val Arg Leu Cys Asp Val Gly Glu Ala Ile
    290                 295                 300

Gln Glu Val Met Glu Ser Tyr Glu Val Glu Ile Asp Gly Lys Thr Tyr
305                 310                 315                 320

Gln Val Lys Pro Ile Arg Asn Leu Asn Gly His Ser Ile Gly Gln Tyr
                325                 330                 335

Arg Ile His Ala Gly Lys Thr Val Pro Ile Val Lys Gly Gly Glu Ala
            340                 345                 350

Thr Arg Met Glu Glu Gly Glu Val Tyr Ala Ile Glu Thr Phe Gly Ser
        355                 360                 365

Thr Gly Lys Gly Val Val His Asp Asp Met Glu Cys Ser His Tyr Met
    370                 375                 380

Lys Asn Phe Asp Val Gly His Val Pro Ile Arg Leu Pro Arg Thr Lys
385                 390                 395                 400

His Leu Leu Asn Val Ile Asn Glu Asn Phe Gly Thr Leu Ala Phe Cys
                405                 410                 415

Arg Arg Trp Leu Asp Arg Leu Gly Glu Ser Lys Tyr Leu Met Ala Leu
            420                 425                 430

Lys Asn Leu Cys Asp Leu Gly Ile Val Asp Pro Tyr Pro Pro Leu Cys
        435                 440                 445

Asp Ile Lys Gly Ser Tyr Thr Ala Gln Phe Glu His Thr Ile Leu Leu
    450                 455                 460

Arg Pro Thr Cys Lys Glu Val Val Ser Arg Gly Asp Asp Tyr
465                 470                 475
```

-continued

<210> SEQ ID NO 5
<211> LENGTH: 3114
<212> TYPE: DNA
<213> ORGANISM: homo sapiens MetAP3 clone GT9D Insert
<220> FEATURE:
<221> NAME/KEY: misc_feature
<222> LOCATION: 1765, 1800, 2896, 2912, 2972, 2977, 2984, 2995, 3009, 3040, 3073
<223> OTHER INFORMATION: n = A,T,C or G

<400> SEQUENCE: 5
cgccaacatg gcggcgccca gtggcgtcca cctgctcgtc cgcagaggta agcgcgtgga 60
ggagagcccc gtgagggttc gcacggttgc tcactaggtt ctcatagaat tttctcttca 120
ccactcaatc atatctactt acacaagcag tcaagcagtc aacaaagaag aaatttcttt 180
tttcggagac aaagagatat ttcacacagt atagttttgc cggctgcagt ttcttcagct 240
catccggttc ctaagcacat aaagaagcca gactatgtga cgacaggcat tgtaccagac 300
tggggagaca gcatagaagt taagaatgaa gatcagattc aagggcttca tcaggcttgt 360
cagctggccc gccacgtcct cctcttggct gggaagagtt taaaggttga catgacaact 420
gaagagatag atgctcttgt tcatcgggaa atcatcagtc ataatgccta tccctcacct 480
ctaggctatg gaggttttcc aaaatctgtt tgtacctctg taaacaacgt gctctgtcat 540
ggtattcctg acagtcgacc tcttcaggat ggagatatta tcaacattga tgtcacagtc 600
tattacaatg gctaccatgg agacacctct gaaacatttt tggtgggcaa tgtggacgaa 660
tgtggtaaaa agttagtgga ggttgccagg aggtgtagag atgaagcaat tgcagcttgc 720
agagcagggg ctcccttctc tgtaattgga aacacaatca gccacataac tcatcagaat 780
ggttttcaag tctgtccaca ttttgtggga catggaatag gatcttactt tcatggacat 840
ccagaaattt ggcatcatgc aaacgacagt gatctaccca tggaggaggg catggcattc 900
actatagagc caatcatcac ggagggatcc cctgaattta aagtcctgga ggatgcatgg 960
actgtggtct ccctagacaa tcaaaggtcg gcgcagttcg agcacacggt tctgatcacg 1020
tcgaggggcg cgcagatcct gaccaaacta ccccatgagg cctgaggagc cgcccgaagg 1080
tcgcggtgac ctggtgcctt tttaaataaa ttgctgaaat ttggctggag aacttttaga 1140
agaaacaggg aaatgaccgg tggtgcggta acctgcgtgg ctcctgatag cgtttggaag 1200
aacgcggggg agactgaaga acaactggga actcggatct gaagccctgc tggggtcgcg 1260
cggctttgga aaaacaaatc ctggccctgg actcggtttc ccaacgcggt caacgcatct 1320
ggaggggact ggaggaaacc cccttgttgg aagagattcc aagagaagca cggtttctct 1380
ttccttgcct gactgttgga gtaaaaaacc tcttaaatcc attgtatcag aggtccttac 1440
ctctctgaca gttacatgat ctttgtatct gaactttgca cgtctgccga aaaatccgaa 1500
cctgttgact gggattttta agaatccgtt tctccctttt gtgtattcca tattggccgg 1560
ccccaaggat gctcgcagaa gccagccccc aaccccagcc cttccgtatc tttcccctcc 1620
atcgcggctt tgcgatgaaa gattagcccg cgaacagagg cattgattac aaacatgtcc 1680
ttggcagtgg actctgggcc tggccattct tcaggtttct gtcaatccag aaacgcgact 1740
ttcctggacc cctgcggctc ttctnccccg ccacattcag ccttcaaggc cagtccagan 1800
gtgaagtttg aggccctccc cccacccacc ccacacgcac gcacgcacgc tagagcgttt 1860
gctgcactag gaattcgagc ttgggcccca ctcgcccagg tgtgaacagt ggctgattag 1920
tgggcggtct agtctctaaa atgacccctc cccagactgg cccttctcgc atcgggaccc 1980

-continued

```
gcgcttgcac gctgcaggag ccgcaaacgt cagctgttct ggaaaccgag agggtcccag   2040
agagaggaga tacgggcgca tttgagagca agggcctact tggccgggac tgaagcttgc   2100
gagttgagct ccagttcggc cggcagttcc atcccgcttc aggaacagga atccaagggc   2160
ccacgctctg tctgcaaggg ccattcctgc ccggagcacc ctcctttccc ttgcgcttgc   2220
tctccggtac ctgttccgca cctgagctca aggcagggag aggccgggcc tctggcagtc   2280
cacgaaggaa gccgtctgcc ttcggttatg attttaggaa caagtccaac gagggtgttc   2340
aagcagttaa tggttgtgct aactcttgtt tctactgaag cgggttttgc aaagctgaca   2400
tcccttaaag ataacttggg ctttcggaag cggcaaggaa atggcacccg tagttgccag   2460
gacaggtggt gtcctcggcc aggactaaga gccagctcat ctttgtaaca ttcataatac   2520
gggaaactga ggaccaggtg gctcggaaaa gagatgagtt ccagctttta cctaacacag   2580
ggttctctcg tcgtccccca acccctccag ctcggcttct ttgtgtccag ggttgtagat   2640
ttttggatag aggtgtttct gattctagtg agtctgagaa ctggaaaaga ccaaggaggg   2700
gttgatgatt tmcaaggtcc atagaaaaac tttttgtgtg gtcggaagtt ggccaagcag   2760
aggcccacag cctgatgcta ctgccccccca ccccccccaaa gatctgaatt cctaaagatc   2820
aagagggttc agctggcctt gggagatgtt tgctggagaa tgacttcagt tttctcctaa   2880
ggcaatcaga ttgcanccat tagcattgta tnttatctgc aaatcagttt actccgaggt   2940
tccccaagga tagttttatt aggaccacag gnctttncta accnctgagg taacncgctg   3000
cttgtgcanc aattattttg aggtggaggt atttatgggn caagtttata attccattta   3060
ttaaagggac tancctaaaa aaaaaaaaaa aaaaaaaaaa aaaagggcgg ccgc         3114
```

<210> SEQ ID NO 6
<211> LENGTH: 217
<212> TYPE: PRT
<213> ORGANISM: homo sapiens MetAP3 insert

<400> SEQUENCE: 6

```
Met Thr Thr Glu Glu Ile Asp Ala Leu Val His Arg Glu Ile Ile Ser
 1               5                  10                  15

His Asn Ala Tyr Pro Ser Pro Leu Gly Tyr Gly Gly Phe Pro Lys Ser
            20                  25                  30

Val Cys Thr Ser Val Asn Asn Val Leu Cys His Gly Ile Pro Asp Ser
        35                  40                  45

Arg Pro Leu Gln Asp Gly Asp Ile Ile Asn Ile Asp Val Thr Val Tyr
    50                  55                  60

Tyr Asn Gly Tyr His Gly Asp Thr Ser Glu Thr Phe Leu Val Gly Asn
65                  70                  75                  80

Glu Asp Glu Cys Gly Lys Lys Leu Val Glu Val Ala Arg Arg Cys Arg
                85                  90                  95

Asp Glu Ala Ile Ala Ala Cys Arg Ala Gly Ala Pro Phe Ser Val Ile
            100                 105                 110

Gly Asn Thr Ile Ser His Ile Thr His Gln Asn Gly Phe Gln Val Cys
        115                 120                 125

Pro His Phe Val Gly His Gly Ile Gly Ser Tyr Phe His Gly His Pro
    130                 135                 140

Glu Ile Trp His His Ala Asn Asp Ser Asp Leu Pro Met Glu Glu Gly
145                 150                 155                 160

Met Ala Phe Thr Ile Glu Pro Ile Ile Thr Glu Gly Ser Pro Glu Phe
                165                 170                 175
```

-continued

```
Lys Val Leu Glu Asp Ala Trp Thr Val Val Ser Leu Asp Asn Gln Arg
            180                 185                 190

Ser Ala Gln Phe Glu His Thr Val Leu Ile Thr Ser Arg Gly Ala Gln
        195                 200                 205

Ile Leu Thr Lys Leu Pro His Glu Ala
    210                 215
```

<210> SEQ ID NO 7
<211> LENGTH: 1529
<212> TYPE: DNA
<213> ORGANISM: homo sapiens MetAP3HZ2 - full length
<220> FEATURE:
<221> NAME/KEY: misc_feature
<222> LOCATION: 1326
<223> OTHER INFORMATION: n = A,T,C or G

<400> SEQUENCE: 7

```
gcggcgccag tggcgtccac ctgctcgtcc gcagaggttc tcatagaatt ttctcttcac      60

cactcaatca tatctactta cacaagcagt caagcagtca acaaagaaga aatttctttt     120

ttcggagaca aagagatatt tcacacagta tagttttgcc ggctgcagtt tcttcagctc     180

atccggttcc taagcacata aagaagccag actatgtgac gacaggcatt gtaccagact     240

ggggagacag catagaagtt aagaatgaag atcagattca agggcttcat caggcttgtc     300

agctggcccg ccacgtcctc ctcttggctg ggaagagttt aaaggttgac atgacaactg     360

aagagataga tgctcttgtt catcgggaaa tcatcagtca taatgcctat ccctcacctc     420

taggctatgg aggttttcca aaatctgttt gtacctctgt aaacaacgtg ctctgtcatg     480

gtattcctga cagtcgacct cttcaggatg gagatattat caacattgat gtcacagtct     540

attacaatgg ctaccatgga gacacctctg aaacattttt ggtgggcaat gtggacgaat     600

gtggtaaaaa gttagtggag gttgccagga ggtgtagaga tgaagcaatt gcagcttgca     660

gagcaggggc tcccttctct gtaattggaa acacaatcag ccacataact catcagaatg     720

gttttcaagt ctgtccacat tttgtgggac atggaatagg atcttacttt catggacatc     780

cagaaatttg gcatcatgca aacgacagtg atctacccat ggaggagggc atggcattca     840

ctatagagcc aatcatcacg gagggatccc ctgaatttaa agtcctggag gatgcatgga     900

ctgtggtctc cctagacaat caaaggtcgg cgcagttcga gcacacggtt ctgatcacgt     960

cgaggggcgc gcagatcctg accaaactac cccatgaggc ctgaggagcc gcccgaaggt    1020

cgcggtgacc tggtgccttt ttaaataaat tgctgaaatt tggctggaga acttttagaa    1080

gaaacaggga aatgaccggt ggtgcggtaa cctgcgtggc tcctgatagc gtttggaaga    1140

acgcggggga gactgaagag caactgggaa ctcggatctg aagccctgct ggggtcgcgc    1200

ggctttggaa aaacaaatcc tggccctgga ctcggtttcc cagcgcggtc aacgcatgtg    1260

gaggggactg gaggaaaccc ccttgttgga agagattcca agagaagcac ggktttctct    1320

ttcccntgcc ctgactgttg gagtaaaaaa cctcttaaat ccattgtatc aagaggtcct    1380

tacctctctg acagttacaa tgatctttgt atctgaactt tgcacgtctg ccgaaaaatc    1440

cgaacctgtt gactgggaaa aaaaaaaaaa aacmmaaaaa aaaaaaaaaa aaaaaaaaaa    1500

aaaaaaaaaa aaaaaaaarg ggcggccgc                                      1529
```

<210> SEQ ID NO 8
<211> LENGTH: 335
<212> TYPE: PRT
<213> ORGANISM: human metAP-3

-continued

<220> FEATURE:
<221> NAME/KEY: PEPTIDE
<222> LOCATION: (1)...(335)
<223> OTHER INFORMATION: Human metAP-3 encoded by SEQ ID NO: 69, comprising parts of SEQ ID NO: 24, SEQ ID NO: 7, and SEQ ID NO: 25

<400> SEQUENCE: 8

```
Met Ala Ala Pro Ser Gly Val His Leu Leu Val Arg Arg Gly Ser His
 1              5                  10                  15

Arg Ile Phe Ser Ser Pro Leu Asn His Ile Tyr Leu His Lys Gln Ser
            20                  25                  30

Ser Ser Gln Gln Arg Arg Asn Phe Phe Phe Arg Arg Gln Arg Asp Ile
        35                  40                  45

Ser His Ser Ile Val Leu Pro Ala Ala Val Ser Ser Ala His Pro Val
    50                  55                  60

Pro Lys His Ile Lys Lys Pro Asp Tyr Val Thr Thr Gly Ile Val Pro
65                  70                  75                  80

Asp Trp Gly Asp Ser Ile Glu Val Lys Asn Glu Asp Gln Ile Gln Gly
                85                  90                  95

Leu His Gln Ala Cys Gln Leu Ala Arg His Val Leu Leu Leu Ala Gly
            100                 105                 110

Lys Ser Leu Lys Val Asp Met Thr Thr Glu Glu Ile Asp Ala Leu Val
        115                 120                 125

His Arg Glu Ile Ile Ser His Asn Ala Tyr Pro Ser Pro Leu Gly Tyr
    130                 135                 140

Gly Gly Phe Pro Lys Ser Val Cys Thr Ser Val Asn Asn Val Leu Cys
145                 150                 155                 160

His Gly Ile Pro Asp Ser Arg Pro Leu Gln Asp Gly Asp Ile Ile Asn
                165                 170                 175

Ile Asp Val Thr Val Tyr Tyr Asn Gly Tyr His Gly Asp Thr Ser Glu
            180                 185                 190

Thr Phe Leu Val Gly Asn Val Asp Glu Cys Gly Lys Lys Leu Val Glu
        195                 200                 205

Val Ala Arg Arg Cys Arg Asp Glu Ala Ile Ala Ala Cys Arg Ala Gly
    210                 215                 220

Ala Pro Phe Ser Val Ile Gly Asn Thr Ile Ser His Ile Thr His Gln
225                 230                 235                 240

Asn Gly Phe Gln Val Cys Pro His Phe Val Gly His Gly Ile Gly Ser
                245                 250                 255

Tyr Phe His Gly His Pro Glu Ile Trp His His Ala Asn Asp Ser Asp
            260                 265                 270

Leu Pro Met Glu Glu Gly Met Ala Phe Thr Ile Glu Pro Ile Ile Thr
        275                 280                 285

Glu Gly Ser Pro Glu Phe Lys Val Leu Glu Asp Ala Trp Thr Val Val
    290                 295                 300

Ser Leu Asp Asn Gln Arg Ser Ala Gln Phe Glu His Thr Val Leu Ile
305                 310                 315                 320

Thr Ser Arg Gly Ala Gln Ile Leu Thr Lys Leu Pro His Glu Ala
                325                 330                 335
```

<210> SEQ ID NO 9
<211> LENGTH: 387
<212> TYPE: PRT
<213> ORGANISM: Saccharomyces cerevisiae MetAP1

<400> SEQUENCE: 9

-continued

```
Met Ser Thr Ala Thr Thr Thr Val Thr Thr Ser Asp Gln Ala Ser His
 1               5                  10                  15

Pro Thr Lys Ile Tyr Cys Ser Gly Leu Gln Cys Gly Arg Glu Thr Ser
            20                  25                  30

Ser Gln Met Lys Cys Pro Val Cys Leu Lys Gln Gly Ile Val Ser Ile
        35                  40                  45

Phe Cys Asp Thr Ser Cys Tyr Glu Asn Asn Tyr Lys Ala His Lys Ala
    50                  55                  60

Leu His Asn Ala Lys Asp Gly Leu Glu Gly Ala Tyr Asp Pro Phe Pro
65                  70                  75                  80

Lys Phe Lys Tyr Ser Gly Lys Val Lys Ala Ser Tyr Pro Leu Thr Pro
                85                  90                  95

Arg Arg Tyr Val Pro Glu Asp Ile Pro Lys Pro Asp Trp Ala Ala Asn
            100                 105                 110

Gly Leu Pro Val Ser Glu Gln Arg Asn Asp Arg Leu Asn Asn Ile Pro
        115                 120                 125

Ile Tyr Lys Lys Asp Gln Ile Lys Lys Ile Arg Lys Ala Cys Met Leu
    130                 135                 140

Gly Arg Glu Val Leu Asp Ile Ala Ala Ala His Val Arg Pro Gly Ile
145                 150                 155                 160

Thr Thr Asp Glu Leu Asp Glu Ile Val His Asn Glu Thr Ile Lys Arg
                165                 170                 175

Gly Ala Tyr Pro Ser Pro Leu Asn Tyr Tyr Asn Phe Pro Lys Ser Leu
            180                 185                 190

Cys Thr Ser Val Asn Glu Val Ile Cys His Gly Val Pro Asp Lys Thr
        195                 200                 205

Val Leu Lys Glu Gly Asp Ile Val Asn Leu Asp Val Ser Leu Tyr Tyr
    210                 215                 220

Gln Gly Tyr His Ala Asp Leu Asn Glu Thr Tyr Tyr Val Gly Glu Asn
225                 230                 235                 240

Ile Ser Lys Glu Ala Leu Asn Thr Thr Glu Thr Ser Arg Glu Cys Leu
                245                 250                 255

Lys Leu Ala Ile Lys Met Cys Lys Pro Gly Thr Thr Phe Gln Glu Leu
            260                 265                 270

Gly Asp His Ile Glu Lys His Ala Thr Glu Asn Lys Cys Ser Val Val
        275                 280                 285

Arg Thr Tyr Cys Gly His Gly Val Gly Glu Phe Phe His Cys Ser Pro
    290                 295                 300

Asn Ile Pro His Tyr Ala Lys Asn Arg Thr Pro Gly Val Met Lys Pro
305                 310                 315                 320

Gly Met Val Phe Thr Ile Glu Pro Met Ile Asn Glu Gly Thr Trp Lys
                325                 330                 335

Asp Met Thr Trp Pro Asp Asp Trp Thr Ser Thr Thr Gln Asp Gly Lys
            340                 345                 350

Leu Ser Ala Gln Phe Glu His Thr Leu Leu Val Thr Glu His Gly Val
        355                 360                 365

Glu Ile Leu Thr Ala Arg Asn Lys Lys Ser Pro Gly Gly Pro Arg Gln
    370                 375                 380

Arg Ile Lys
385
```

<210> SEQ ID NO 10
<211> LENGTH: 253

-continued

<212> TYPE: PRT
<213> ORGANISM: Synechocystis sp. MetAP1

<400> SEQUENCE: 10

```
Met Gly Asp Thr Ile Thr Leu Leu Ser Arg Arg Glu Ile Glu Lys Met
 1               5                  10                  15

Arg Gln Ala Gly Gln Leu Ala Ala Ala Leu Leu Asp His Leu Ala Pro
            20                  25                  30

Met Val Gln Pro Gly Ile Thr Thr Leu Glu Leu Asn Asp Glu Ala Glu
        35                  40                  45

Lys Trp Thr Lys Ala His Gly Ala Ile Ser Ala Pro Leu Gly Tyr Asn
    50                  55                  60

Gly Phe Pro Lys Ser Ile Cys Thr Ser Ile Asn Glu Val Ile Cys His
65                  70                  75                  80

Gly Ile Pro His Arg Lys Arg Val Leu Gln Ala Gly Asp Ile Ile Asn
                85                  90                  95

Val Asp Val Thr Pro Ile Val Asp Gly Tyr His Gly Asp Cys Ser Arg
            100                 105                 110

Thr Phe Phe Val Gly Thr Pro Ser Pro Val Ala Glu Lys Leu Val Lys
        115                 120                 125

Val Thr Glu Glu Cys Leu Arg Leu Gly Ile Glu Ala Val Lys Pro Gly
    130                 135                 140

Gly Lys Ile Gly Asp Ile Gly Ala Ala Ile Gln Ser His Ala Glu Ala
145                 150                 155                 160

Gln Gly Phe Ser Val Val Arg Asp Phe Val Gly His Gly Ile Ser Lys
                165                 170                 175

Ile Phe His Thr Ala Pro Gln Ile Pro His Tyr Gly Lys Ala Gly Lys
            180                 185                 190

Gly Lys Arg Leu Arg Pro Gly Met Val Phe Thr Ile Glu Pro Met Ile
        195                 200                 205

Asn Glu Gly Thr Trp Glu Ala Val Leu Leu Asp Asp Gly Trp Thr Ala
    210                 215                 220

Ile Thr Lys Asp Gly Lys Leu Ser Ala Gln Phe Glu His Thr Ile Ala
225                 230                 235                 240

Val Thr Glu Asp Gly Val Glu Ile Leu Thr Leu Gly Glu
                245                 250
```

<210> SEQ ID NO 11
<211> LENGTH: 274
<212> TYPE: PRT
<213> ORGANISM: Synechocystis sp. MetAP2

<400> SEQUENCE: 11

```
Met Asn His Gln Asn Leu Leu Ser Ile Thr Arg Asn Leu Val His Pro
 1               5                  10                  15

Pro Ile Ser Ser Gly Leu Val Leu Leu Ser Ala Arg Glu Leu Asp Lys
            20                  25                  30

Met Arg Arg Val Gly Gln Leu Ala Ala Asn Leu Leu Asn His Leu Glu
        35                  40                  45

Ser Met Val Gln Pro Gly Val Ser Thr Gln Ala Leu Asn Asp Glu Ala
    50                  55                  60

Thr Arg Trp Met Glu Asp His Gly Ala Ile Ser Ala Thr Leu Gly Tyr
65                  70                  75                  80

Ala Pro Pro Gly Tyr Pro Pro Phe Thr Gly Ala Ile Cys Thr Ser Ile
                85                  90                  95
```

-continued

```
Asn Glu Val Val Cys His Gly Ile Pro Asn Pro Lys Gln Ile Leu Lys
            100                 105                 110

Asp Gly Asp Ile Ile Asn Ile Asp Val Thr Leu Arg Leu Ala Gly Tyr
        115                 120                 125

His Gly Asp Thr Ser Arg Thr Phe Leu Val Gly Ser Val Ser Ala Thr
    130                 135                 140

Ala Arg Lys Leu Val Glu Ala Thr Gln Glu Ser Met Met Arg Gly Ile
145                 150                 155                 160

Ala Glu Ile Lys Pro Gly Ala Arg Ile Gly Asp Ile Gly Ala Ala Ile
                165                 170                 175

Gln Ala Tyr Ala Glu Ala Ser Gly Phe Ser Val Val Arg Asp Met Val
            180                 185                 190

Gly His Gly Ile Gly Arg Gln Met His Thr Glu Leu Gln Ile Pro His
        195                 200                 205

Tyr Gly Lys Arg Gly Ser Gly Leu Lys Leu Arg Pro Gly Met Val Phe
    210                 215                 220

Thr Val Glu Pro Met Leu Asn Glu Gly Thr Tyr Glu Leu Thr Phe Leu
225                 230                 235                 240

Ala Asp Gly Trp Thr Val Ile Thr Lys Asp Lys Lys Leu Ser Ala Gln
                245                 250                 255

Phe Glu His Thr Val Val Val Thr Glu Glu Gly Val Glu Ile Leu Thr
            260                 265                 270

Leu Ala


<210> SEQ ID NO 12
<211> LENGTH: 264
<212> TYPE: PRT
<213> ORGANISM: E. colli MetAP

<400> SEQUENCE: 12

Met Ala Ile Ser Ile Lys Thr Pro Glu Asp Ile Glu Lys Met Arg Val
 1               5                  10                  15

Ala Gly Arg Leu Ala Ala Glu Val Leu Glu Met Ile Glu Pro Tyr Val
            20                  25                  30

Lys Pro Gly Val Ser Thr Gly Glu Leu Asp Arg Ile Cys Asn Asp Tyr
        35                  40                  45

Ile Val Asn Glu Gln His Ala Val Ser Ala Cys Leu Gly Tyr His Gly
    50                  55                  60

Tyr Pro Lys Ser Val Cys Ile Ser Ile Asn Glu Val Val Cys His Gly
65                  70                  75                  80

Ile Pro Asp Asp Ala Lys Leu Leu Lys Asp Gly Asp Ile Val Asn Ile
                85                  90                  95

Asp Val Thr Val Ile Lys Asp Gly Phe His Gly Asp Thr Ser Lys Met
            100                 105                 110

Phe Ile Val Gly Lys Pro Thr Ile Met Gly Glu Arg Leu Cys Arg Ile
        115                 120                 125

Thr Gln Glu Ser Leu Tyr Leu Ala Leu Arg Met Val Lys Pro Gly Ile
    130                 135                 140

Asn Leu Arg Glu Ile Gly Ala Ala Ile Gln Lys Phe Val Glu Ala Glu
145                 150                 155                 160

Gly Phe Ser Val Val Arg Glu Tyr Cys Gly His Gly Ile Gly Arg Gly
                165                 170                 175

Phe His Glu Glu Pro Gln Val Leu His Tyr Asp Ser Arg Glu Thr Asn
            180                 185                 190
```

-continued

```
Val Val Leu Lys Pro Gly Met Thr Phe Thr Ile Glu Pro Met Val Asn
        195                 200                 205

Ala Gly Lys Lys Glu Ile Arg Thr Met Lys Asp Gly Trp Thr Val Lys
    210                 215                 220

Thr Lys Asp Arg Ser Leu Ser Ala Gln Tyr Glu His Thr Ile Val Val
225                 230                 235                 240

Thr Asp Asn Gly Cys Glu Ile Leu Thr Leu Arg Lys Asp Asp Thr Ile
                245                 250                 255

Pro Ala Ile Ile Ser His Asp Glu
            260


<210> SEQ ID NO 13
<211> LENGTH: 268
<212> TYPE: PRT
<213> ORGANISM: Haemophilus influenzae MetAP

<400> SEQUENCE: 13

Met Ala Ile Pro Ile Arg Thr Glu Lys Glu Ile Val Lys Leu Arg Glu
 1               5                  10                  15

Ala Cys Lys Leu Ala Ser Asp Val Leu Val Met Ile Glu Pro Tyr Val
            20                  25                  30

Lys Ala Gly Val Thr Thr Gly Glu Leu Asp Arg Ile Cys His Glu Tyr
        35                  40                  45

Met Val Asn Glu Gln Lys Val Ile Pro Ala Cys Leu Asn Tyr His Gly
    50                  55                  60

Phe Pro Lys Ala Thr Cys Ile Ser Ile Asn Glu Val Val Cys His Gly
65                  70                  75                  80

Ile Pro Ser Asp Asp Lys Val Leu Lys Asn Gly Asp Ile Val Asn Ile
                85                  90                  95

Asp Val Thr Val Ile Lys Asp Gly Tyr Phe Gly Asp Asn Ser Lys Met
            100                 105                 110

Tyr Ile Val Gly Gly Glu Thr Asn Ile Arg Ser Lys Lys Leu Val Glu
        115                 120                 125

Ala Ala Gln Glu Ala Leu Tyr Val Gly Ile Arg Thr Val Lys Pro Asp
    130                 135                 140

Ile Arg Leu Asn Glu Ile Gly Lys Ala Val Gln Lys Tyr Thr Glu Ser
145                 150                 155                 160

Gln Thr Phe Ser Val Val Arg Glu Tyr Cys Gly His Gly Val Gly Thr
                165                 170                 175

Glu Phe His Cys Glu Pro Gln Val Leu His Tyr Tyr Ala Asp Asp Gly
            180                 185                 190

Gly Val Ile Leu Lys Pro Gly Met Val Phe Thr Ile Glu Pro Met Ile
        195                 200                 205

Asn Ala Gly Lys Lys Glu Val Arg Val Met Gly Asp Gly Trp Thr Val
    210                 215                 220

Lys Thr Lys Asp Arg Ser His Ser Ala Gln Tyr Glu His Gln Leu Ile
225                 230                 235                 240

Val Thr Glu Thr Gly Cys Glu Val Met Thr Ile Arg Asp Glu Glu Ile
                245                 250                 255

Ala Glu Gly Arg Ile Ser Arg Ile Met Val Asn Val
            260                 265


<210> SEQ ID NO 14
<211> LENGTH: 305
<212> TYPE: PRT
<213> ORGANISM: Synechocystis sp. MetAP3
```

-continued

<400> SEQUENCE: 14

```
Met Pro Arg Ile Phe Pro Trp Lys Leu Trp Arg Lys Ser Arg Pro Ala
 1               5                  10                  15

Trp Pro Arg Phe Leu Gly Thr His Pro Met Asn Leu Leu Ser Gln Leu
            20                  25                  30

Phe Ala Pro Pro Ser Pro Val Pro Ser Pro Thr Pro Lys Ala Lys Lys
        35                  40                  45

Arg Ser Arg Arg Gly Val Gln Ile Lys Thr Pro Ala Glu Ile Ala Ile
    50                  55                  60

Met Arg Gln Ala Gly Ala Ile Ala Ala Gln Val Leu Lys Glu Ile Ala
65                  70                  75                  80

Ala Thr Val Gln Pro Gly Met Thr Thr Gly Asp Leu Asp Gln Leu Ala
                85                  90                  95

Glu Glu Arg Ile Arg Ser Leu Gly Ala Thr Pro Ser Phe Lys Gly Tyr
            100                 105                 110

His Gly Phe Pro Ala Ser Ile Cys Ala Cys Val Asn Asn Glu Val Val
        115                 120                 125

His Gly Ile Pro Arg Arg Arg Lys Lys Ile Arg Ser Gly Asp Leu Leu
    130                 135                 140

Lys Val Asp Thr Gly Ala Tyr Phe Gln Gly Tyr His Gly Asp Ser Cys
145                 150                 155                 160

Ile Thr Ile Ala Val Gly Lys Val Ser Pro Gln Ala Gln Arg Leu Met
                165                 170                 175

Glu Val Ala Glu Gly Ala Leu Tyr Ala Gly Ile Glu Gln Val Lys Pro
            180                 185                 190

Gly Asn Tyr Leu Met Asp Ile Ala Gly Ala Ile Glu Asp Tyr Val Lys
        195                 200                 205

Pro Thr Gly Tyr Thr Ile Val Glu Glu Phe Thr Gly His Gly Val Gly
    210                 215                 220

Gln Ala Leu His Glu Asp Pro His Val Phe Asn Val Arg Cys Arg Asp
225                 230                 235                 240

Leu Pro Asn Val Lys Leu Lys Pro Gly Met Thr Leu Ala Ile Glu Pro
                245                 250                 255

Ile Val Asn Ala Gly Ser Arg Phe Thr Arg Thr Leu Gly Asp Arg Trp
            260                 265                 270

Thr Val Val Thr Val Asp Asn Ala Leu Ser Ala Gln Phe Glu His Thr
        275                 280                 285

Val Leu Val Thr Ala Thr Gly Tyr Glu Leu Leu Thr Asp Arg Arg Leu
    290                 295                 300

Val
305
```

<210> SEQ ID NO 15
<211> LENGTH: 248
<212> TYPE: PRT
<213> ORGANISM: Bacillus subtilus MetAP

<400> SEQUENCE: 15

```
Met Ile Ile Cys Lys Thr Pro Arg Glu Leu Gly Ile Met Arg Glu Ala
 1               5                  10                  15

Gly Arg Ile Val Ala Leu Thr His Glu Glu Leu Lys Lys His Ile Lys
            20                  25                  30

Pro Gly Ile Ser Thr Lys Glu Leu Asp Gln Ile Ala Glu Arg Phe Ile
        35                  40                  45
```

-continued

```
Lys Lys Gln Gly Ala Ile Pro Ser Phe Lys Gly Tyr Asn Gly Phe Arg
    50                  55                  60

Gly Ser Ile Cys Val Ser Val Asn Glu Glu Leu Val His Gly Ile Pro
65                  70                  75                  80

Gly Ser Arg Val Leu Lys Asp Gly Asp Ile Ile Ser Ile Asp Ile Gly
                85                  90                  95

Ala Lys Leu Asn Gly Tyr His Gly Asp Ser Ala Trp Thr Tyr Pro Val
            100                 105                 110

Gly Asn Ile Ser Asp Asp Asp Lys Lys Leu Leu Glu Val Thr Glu Glu
        115                 120                 125

Ser Leu Tyr Lys Gly Leu Gln Glu Ala Lys Pro Gly Glu Arg Leu Ser
    130                 135                 140

Asn Ile Ser His Ala Ile Gln Thr Tyr Val Glu Asn Glu Gln Phe Ser
145                 150                 155                 160

Val Val Arg Glu Tyr Val Gly His Gly Val Gly Gln Asp Leu His Glu
                165                 170                 175

Asp Pro Gln Ile Pro His Tyr Gly Pro Pro Asn Lys Gly Pro Arg Leu
            180                 185                 190

Lys Pro Gly Met Val Leu Ala Ile Glu Pro Met Val Asn Ala Gly Ser
        195                 200                 205

Arg Tyr Val Lys Thr Leu Ala Asp Asn Trp Thr Val Val Thr Val Asp
    210                 215                 220

Gly Lys Lys Cys Ala His Phe Glu His Thr Ile Ala Ile Thr Glu Thr
225                 230                 235                 240

Gly Phe Asp Ile Leu Thr Arg Val
                245


<210> SEQ ID NO 16
<211> LENGTH: 478
<212> TYPE: PRT
<213> ORGANISM: Mus musculus MetAP2

<400> SEQUENCE: 16

Met Ala Gly Val Glu Gln Ala Ala Ser Phe Gly Gly His Leu Asn Gly
 1               5                  10                  15

Asp Leu Asp Pro Asp Asp Arg Glu Glu Gly Thr Ser Ser Thr Ala Glu
            20                  25                  30

Glu Ala Ala Lys Lys Lys Arg Arg Lys Lys Lys Lys Gly Lys Gly Ala
        35                  40                  45

Val Ser Ala Val Gln Gln Glu Leu Asp Lys Glu Ser Gly Ala Leu Val
    50                  55                  60

Asp Glu Val Ala Lys Gln Leu Glu Ser Gln Ala Leu Glu Glu Lys Glu
65                  70                  75                  80

Arg Asp Asp Asp Asp Glu Asp Gly Asp Gly Asp Ala Asp Gly Ala Thr
                85                  90                  95

Gly Lys Lys Lys Lys Lys Lys Lys Lys Lys Arg Gly Pro Lys Val Gln
            100                 105                 110

Thr Asp Pro Pro Ser Val Pro Ile Cys Asp Leu Tyr Pro Asn Gly Val
        115                 120                 125

Phe Pro Lys Gly Gln Glu Cys Glu Tyr Pro Pro Thr Gln Asp Gly Arg
    130                 135                 140

Thr Ala Ala Trp Arg Thr Thr Ser Glu Glu Lys Lys Ala Leu Asp Gln
145                 150                 155                 160

Ala Ser Glu Glu Ile Trp Asn Asp Phe Arg Glu Ala Ala Glu Ala His
```

-continued

```
                165                 170                 175

Arg Gln Val Arg Lys Tyr Val Met Ser Trp Ile Lys Pro Gly Met Thr
            180                 185                 190

Met Ile Glu Ile Cys Glu Lys Leu Glu Asp Cys Ser Arg Lys Leu Ile
        195                 200                 205

Lys Glu Asn Gly Leu Asn Ala Gly Leu Ala Phe Pro Thr Gly Cys Ser
    210                 215                 220

Leu Asn Asn Cys Ala Ala His Tyr Thr Pro Asn Ala Gly Asp Thr Thr
225                 230                 235                 240

Val Leu Gln Tyr Asp Asp Ile Cys Lys Ile Asp Phe Gly Thr His Ile
                245                 250                 255

Ser Gly Arg Ile Ile Asp Cys Ala Phe Thr Val Thr Phe Asn Pro Lys
            260                 265                 270

Tyr Asp Ile Leu Leu Thr Ala Val Lys Asp Ala Thr Asn Thr Gly Ile
        275                 280                 285

Lys Cys Ala Gly Ile Asp Val Arg Leu Cys Asp Val Gly Glu Ala Ile
    290                 295                 300

Gln Glu Val Met Glu Ser Tyr Glu Val Glu Ile Asp Gly Lys Thr Tyr
305                 310                 315                 320

Gln Val Lys Pro Ile Arg Asn Leu Asn Gly His Ser Ile Gly Pro Tyr
                325                 330                 335

Arg Ile His Ala Gly Lys Thr Val Pro Ile Val Lys Gly Gly Glu Ala
            340                 345                 350

Thr Arg Met Glu Glu Gly Glu Val Tyr Ala Ile Glu Thr Phe Gly Ser
        355                 360                 365

Thr Gly Lys Gly Val Val His Asp Asp Met Glu Cys Ser His Tyr Met
    370                 375                 380

Lys Asn Phe Asp Val Gly His Val Pro Ile Arg Leu Pro Arg Thr Lys
385                 390                 395                 400

His Leu Leu Asn Val Ile Asn Glu Asn Phe Gly Thr Leu Ala Phe Cys
                405                 410                 415

Arg Arg Trp Leu Asp Arg Leu Gly Glu Ser Lys Tyr Leu Met Ala Leu
            420                 425                 430

Lys Asn Leu Cys Asp Leu Gly Ile Val Asp Pro Tyr Pro Pro Leu Cys
        435                 440                 445

Asp Ile Lys Gly Ser Tyr Thr Ala Gln Phe Glu His Thr Ile Leu Leu
    450                 455                 460

Arg Pro Thr Cys Lys Glu Val Val Ser Arg Gly Asp Asp Tyr
465                 470                 475


<210> SEQ ID NO 17
<211> LENGTH: 478
<212> TYPE: PRT
<213> ORGANISM: Rattus MetAP2

<400> SEQUENCE: 17

Met Ala Gly Val Glu Glu Ala Ser Ser Phe Gly Gly His Leu Asn Arg
 1               5                  10                  15

Asp Leu Asp Pro Asp Asp Arg Glu Glu Gly Thr Ser Ser Thr Ala Glu
            20                  25                  30

Glu Ala Ala Lys Lys Lys Arg Arg Lys Lys Lys Lys Gly Lys Gly Ala
        35                  40                  45

Val Ser Ala Gly Gln Gln Glu Leu Asp Lys Glu Ser Gly Thr Ser Val
    50                  55                  60
```

-continued

```
Asp Glu Val Ala Lys Gln Leu Glu Arg Gln Ala Leu Glu Glu Lys Glu
65                  70                  75                  80

Lys Asp Asp Asp Asp Glu Asp Gly Asp Gly Asp Gly Asp Gly Ala Ala
                85                  90                  95

Gly Lys Lys Lys Lys Lys Lys Lys Lys Lys Arg Gly Pro Arg Val Gln
            100                 105                 110

Thr Asp Pro Pro Ser Val Pro Ile Cys Asp Leu Tyr Pro Asn Gly Val
        115                 120                 125

Phe Pro Lys Gly Gln Glu Cys Glu Tyr Pro Pro Thr Gln Asp Gly Arg
    130                 135                 140

Thr Ala Ala Trp Arg Thr Thr Ser Glu Glu Lys Lys Ala Leu Asp Gln
145                 150                 155                 160

Ala Ser Glu Glu Ile Trp Asn Asp Phe Arg Glu Ala Ala Glu Ala His
                165                 170                 175

Arg Gln Val Arg Lys Tyr Val Met Ser Trp Ile Lys Pro Gly Met Thr
            180                 185                 190

Met Ile Glu Ile Cys Glu Lys Leu Glu Asp Cys Ser Arg Lys Leu Ile
        195                 200                 205

Lys Glu Asn Gly Leu Asn Ala Gly Leu Ala Phe Pro Thr Gly Cys Ser
    210                 215                 220

Leu Asn Asn Cys Ala Ala His Tyr Thr Pro Asn Ala Gly Asp Thr Thr
225                 230                 235                 240

Val Leu Gln Tyr Asp Asp Ile Cys Lys Ile Asp Phe Gly Thr His Ile
                245                 250                 255

Ser Gly Arg Ile Ile Asp Cys Ala Phe Thr Val Thr Phe Asn Pro Lys
            260                 265                 270

Tyr Asp Ile Leu Leu Lys Ala Val Lys Asp Ala Thr Asn Thr Gly Ile
        275                 280                 285

Lys Cys Ala Gly Ile Asp Val Arg Leu Cys Asp Val Gly Glu Ala Ile
    290                 295                 300

Gln Glu Val Met Glu Ser Tyr Glu Val Glu Ile Asp Gly Lys Thr Tyr
305                 310                 315                 320

Gln Val Lys Pro Ile Arg Asn Leu Asn Gly His Ser Ile Gly Pro Tyr
                325                 330                 335

Arg Ile His Ala Gly Lys Thr Val Pro Ile Val Lys Gly Gly Glu Ala
            340                 345                 350

Thr Arg Met Glu Glu Gly Glu Val Tyr Ala Ile Glu Thr Phe Gly Ser
        355                 360                 365

Thr Gly Lys Gly Val Val His Asp Asp Met Glu Cys Ser His Tyr Met
    370                 375                 380

Lys Asn Phe Asp Val Gly His Val Pro Ile Arg Leu Pro Arg Thr Lys
385                 390                 395                 400

His Leu Leu Asn Val Ile Asn Glu Asn Phe Gly Thr Leu Ala Phe Cys
                405                 410                 415

Arg Arg Trp Leu Asp Arg Leu Gly Glu Ser Lys Tyr Leu Met Ala Leu
            420                 425                 430

Lys Asn Leu Cys Asp Leu Gly Ile Val Asp Pro Tyr Pro Pro Leu Cys
        435                 440                 445

Asp Ile Lys Gly Ser Tyr Thr Ala Gln Phe Glu His Thr Ile Leu Leu
    450                 455                 460

Arg Pro Thr Cys Lys Glu Val Val Ser Arg Gly Asp Asp Tyr
465                 470                 475
```

-continued

<210> SEQ ID NO 18
<211> LENGTH: 421
<212> TYPE: PRT
<213> ORGANISM: Saccharomyces cerevisiae MetAP2

<400> SEQUENCE: 18

```
Met Thr Asp Ala Glu Ile Glu Asn Ser Pro Ala Ser Asp Leu Lys Glu
 1               5                  10                  15

Leu Asn Leu Glu Asn Glu Gly Val Glu Gln Gln Asp Gln Ala Lys Ala
            20                  25                  30

Asp Glu Ser Asp Pro Val Glu Ser Lys Lys Lys Lys Asn Lys Lys Lys
        35                  40                  45

Lys Lys Lys Lys Ser Asn Val Lys Lys Ile Glu Leu Leu Phe Pro Asp
    50                  55                  60

Gly Lys Tyr Pro Glu Gly Ala Trp Met Asp Tyr His Gln Asp Phe Asn
65                  70                  75                  80

Leu Gln Arg Thr Thr Asp Glu Glu Ser Arg Tyr Leu Lys Arg Asp Leu
                85                  90                  95

Glu Arg Ala Glu His Trp Asn Asp Val Arg Lys Gly Ala Glu Ile His
            100                 105                 110

Arg Arg Val Arg Arg Ala Ile Lys Asp Arg Ile Val Pro Gly Met Lys
        115                 120                 125

Leu Met Asp Ile Ala Asp Met Ile Glu Asn Thr Thr Arg Lys Tyr Thr
    130                 135                 140

Gly Ala Glu Asn Leu Leu Ala Met Glu Asp Pro Lys Ser Gln Gly Ile
145                 150                 155                 160

Gly Phe Pro Thr Gly Leu Ser Leu Asn His Cys Ala Ala His Phe Thr
                165                 170                 175

Pro Asn Ala Gly Asp Lys Thr Val Leu Lys Tyr Glu Asp Val Met Lys
            180                 185                 190

Val Asp Tyr Gly Val Gln Val Asn Gly Asn Ile Ile Asp Ser Ala Phe
        195                 200                 205

Thr Val Ser Phe Asp Pro Gln Tyr Asp Asn Leu Leu Ala Ala Val Lys
    210                 215                 220

Asp Ala Thr Tyr Thr Gly Ile Lys Glu Ala Gly Ile Asp Val Arg Leu
225                 230                 235                 240

Thr Asp Ile Gly Glu Ala Ile Gln Glu Val Met Glu Ser Tyr Glu Val
                245                 250                 255

Glu Ile Asn Gly Glu Thr Tyr Gln Val Lys Pro Cys Arg Asn Leu Cys
            260                 265                 270

Gly His Ser Ile Ala Pro Tyr Arg Ile His Gly Gly Lys Ser Val Pro
        275                 280                 285

Ile Val Lys Asn Gly Asp Thr Thr Lys Met Glu Glu Gly Glu His Phe
    290                 295                 300

Ala Ile Glu Thr Phe Gly Ser Thr Gly Arg Gly Tyr Val Thr Ala Gly
305                 310                 315                 320

Gly Glu Val Ser His Tyr Ala Arg Ser Ala Glu Asp His Gln Val Met
                325                 330                 335

Pro Thr Leu Asp Ser Ala Lys Asn Leu Leu Lys Thr Ile Asp Arg Asn
            340                 345                 350

Phe Gly Thr Leu Pro Phe Cys Arg Arg Tyr Leu Asp Arg Leu Gly Gln
        355                 360                 365

Glu Lys Tyr Leu Phe Ala Leu Asn Asn Leu Val Arg His Gly Leu Val
    370                 375                 380
```

-continued

```
Gln Asp Tyr Pro Pro Leu Asn Asp Ile Pro Gly Ser Tyr Thr Ala Gln
385                 390                 395                 400

Phe Glu His Thr Ile Leu Leu His Ala His Lys Lys Glu Val Val Ser
                405                 410                 415

Lys Gly Asp Asp Tyr
            420


<210> SEQ ID NO 19
<211> LENGTH: 188
<212> TYPE: PRT
<213> ORGANISM: Methanothermus fervidus MetAP

<400> SEQUENCE: 19

Met Glu Lys Phe Lys Lys Ala Gly Lys Ile Ala Ser Lys Val Arg Lys
 1               5                  10                  15

Lys Ala Ile Lys Ala Val Lys Gly Glu Met Lys Ile Leu Asp Leu Ala
            20                  25                  30

Glu Phe Ile Glu Asn Glu Ile Glu Lys Met Gly Ala Lys Pro Ala Phe
        35                  40                  45

Pro Cys Asn Ile Ser Val Asn Glu Ile Thr Ala His Tyr Ser Pro Pro
    50                  55                  60

Cys Asn Asp Asp Arg Lys Ile Leu Pro Gly Asp Leu Val Lys Ile Asp
65                  70                  75                  80

Ile Gly Val His Val Asp Gly Phe Ile Gly Asp Thr Ala Thr Thr Val
                85                  90                  95

Leu Val Glu Gly Tyr Glu Asp Leu Lys Asn Tyr Asn Asp Glu Leu Ala
            100                 105                 110

Glu Lys Asn Lys Lys Met Ile Glu Ala Ala Glu Ser Ala Leu Glu Asn
        115                 120                 125

Ala Ile Asn Thr Ile Arg Asp Gly Val Glu Ile Gly Lys Ile Gly Glu
    130                 135                 140

Val Ile Glu Asn Thr Ile Asn Lys Phe Gly Phe Lys Pro Ile Ser Asn
145                 150                 155                 160

Leu Thr Gly His Thr Ile Asp Arg Trp Val Leu His Ser Gly Leu Ser
                165                 170                 175

Ile Pro Asn Val Lys Gly Gln Asn Ser His Lys Leu
            180                 185


<210> SEQ ID NO 20
<211> LENGTH: 294
<212> TYPE: PRT
<213> ORGANISM: Methanothermus jannaschii MetAP
<220> FEATURE:
<221> NAME/KEY: VARIANT
<222> LOCATION: 28
<223> OTHER INFORMATION: Xaa = Any Amino Acid

<400> SEQUENCE: 20

Met Glu Ile Glu Gly Tyr Glu Lys Ile Ile Glu Ala Gly Lys Ile Ala
 1               5                  10                  15

Ser Lys Val Arg Glu Glu Ala Val Lys Leu Ile Xaa Pro Gly Val Lys
            20                  25                  30

Leu Leu Glu Val Ala Glu Phe Val Glu Asn Arg Ile Arg Glu Leu Gly
        35                  40                  45

Gly Glu Pro Ala Phe Pro Cys Asn Ile Ser Ile Asn Glu Ile Ala Ala
    50                  55                  60

His Tyr Thr Pro Lys Leu Asn Asp Asn Leu Glu Phe Lys Asp Asp Asp
65                  70                  75                  80
```

-continued

```
Val Val Lys Leu Asp Leu Gly Ala His Val Asp Gly Tyr Ile Ala Asp
                85                  90                  95

Thr Ala Ile Thr Val Asp Leu Ser Asn Ser Tyr Lys Asp Leu Val Lys
            100                 105                 110

Ala Ser Glu Asp Ala Leu Tyr Thr Val Ile Lys Glu Ile Asn Pro Pro
        115                 120                 125

Met Asn Ile Gly Glu Met Gly Lys Ile Ile Gln Glu Val Ile Glu Ser
    130                 135                 140

Tyr Gly Tyr Lys Pro Ile Ser Asn Leu Ser Gly His Val Met His Arg
145                 150                 155                 160

Tyr Glu Leu His Thr Gly Ile Ser Ile Pro Asn Val Tyr Glu Arg Thr
                165                 170                 175

Asn Gln Tyr Ile Asp Val Gly Asp Leu Val Ala Ile Glu Pro Phe Ala
            180                 185                 190

Thr Asp Gly Phe Gly Met Val Lys Asp Gly Asn Leu Gly Asn Ile Tyr
        195                 200                 205

Lys Phe Leu Ala Lys Arg Pro Ile Arg Leu Pro Gln Ala Arg Lys Leu
    210                 215                 220

Leu Asp Val Ile Ser Lys Asn Tyr Pro Tyr Leu Pro Phe Ala Glu Arg
225                 230                 235                 240

Trp Val Leu Lys Asn Glu Ser Glu Arg Leu Ala Leu Asn Ser Leu Ile
                245                 250                 255

Arg Ala Ser Cys Ile Tyr Gly Tyr Pro Ile Leu Lys Glu Arg Glu Asn
            260                 265                 270

Gly Ile Val Gly Gln Ala Glu His Thr Ile Leu Ile Thr Glu Asn Gly
        275                 280                 285

Val Glu Ile Thr Thr Lys
    290


<210> SEQ ID NO 21
<211> LENGTH: 301
<212> TYPE: PRT
<213> ORGANISM: Sulfolobus solfataricus MetAP

<400> SEQUENCE: 21

Met Thr Glu Asp Glu Leu Asn Lys Leu Leu Leu Ala Gly Lys Ile Ala
 1               5                  10                  15

Ala Lys Ala Arg Asp Glu Val Ser Leu Asp Val Lys Ala Ser Ala Lys
            20                  25                  30

Val Leu Asp Ile Cys Glu Glu Val Glu Ser Ile Ile Ile Glu Asn Lys
        35                  40                  45

Ala Phe Pro Ser Phe Pro Cys Asn Ile Ser Ile Asn Ser Glu Ala Ala
    50                  55                  60

His Tyr Ser Pro Thr Ile Asn Asp Glu Lys Arg Ile Pro Glu Gly Ala
65                  70                  75                  80

Val Val Lys Leu Asp Leu Gly Ala His Ile Asp Gly Phe Ile Ser Asp
                85                  90                  95

Thr Ala Ile Thr Ile Ser Leu Asp Ser Arg Tyr Gln Arg Leu Leu Asp
            100                 105                 110

Ala Ser Lys Thr Ala Leu Glu Ala Ala Ile Thr Asn Phe Lys Ala Gly
        115                 120                 125

Leu Ser Ile Gly Glu Ile Gly Arg Val Ile Glu Lys Val Ile Arg Ala
    130                 135                 140

Gln Gly Tyr Lys Pro Ile Arg Asn Leu Gly Gly His Leu Ile Arg Arg
```

-continued

```
145                 150                 155                 160

Tyr Glu Leu His Ala Gly Val Phe Ile Pro Asn Val Tyr Glu Arg Gly
                165                 170                 175

Leu Gly Val Ile Gln Ser Asp Ser Val Tyr Ala Ile Glu Pro Phe Ala
            180                 185                 190

Thr Asp Gly Gly Gly Glu Val Val Glu Gly Lys Ser Ile Thr Ile Tyr
        195                 200                 205

Ser Leu Lys Asn Pro Asn Ile Lys Gly Leu Ser Ser Arg Glu Asn Glu
    210                 215                 220

Leu Ile Asp Phe Ile Tyr Thr Arg Phe Asn Tyr Leu Pro Phe Ser Glu
225                 230                 235                 240

Arg Trp Leu Lys Glu Phe Ser Thr Asn Val Asp Glu Leu Arg Asn Asn
                245                 250                 255

Ile Lys Asn Leu Val Lys Lys Gly Ala Leu Arg Gly Tyr Pro Ile Leu
            260                 265                 270

Ile Glu Ile Lys Lys Gly Val Val Ser Gln Phe Glu His Thr Val Ile
        275                 280                 285

Val Lys Gly Asp Ser Ile Ile Val Ser Thr Lys Ser Leu
    290                 295                 300


<210> SEQ ID NO 22
<211> LENGTH: 250
<212> TYPE: PRT
<213> ORGANISM: Helicobacter pylori MetAP

<400> SEQUENCE: 22

Met Ala Ile Ser Ile Lys Ser Pro Lys Glu Ile Lys Ala Leu Arg Lys
 1               5                  10                  15

Ala Gly Glu Leu Thr Ala Gln Ala Leu Ala Leu Leu Glu Arg Glu Val
            20                  25                  30

Arg Pro Gly Val Ser Leu Leu Glu Leu Asp Lys Met Ala Glu Asp Phe
        35                  40                  45

Ile Lys Ser Ser His Ala Arg Pro Ala Phe Lys Gly Leu Tyr Gly Phe
    50                  55                  60

Pro Asn Ser Val Cys Met Ser Leu Asn Glu Val Val Ile His Gly Ile
65                  70                  75                  80

Pro Thr Asp Tyr Val Leu Gln Glu Gly Asp Ile Ile Gly Leu Asp Leu
                85                  90                  95

Gly Val Glu Val Asp Gly Tyr Tyr Gly Asp Ser Ala Leu Thr Leu Pro
            100                 105                 110

Ile Gly Ala Ile Ser Pro Gln Asp Glu Lys Leu Leu Ala Cys Ser Lys
        115                 120                 125

Glu Ser Leu Met His Ala Ile Asn Ser Ile Arg Val Gly Met His Phe
    130                 135                 140

Lys Glu Leu Ser Gln Ile Leu Glu Ser Thr Ile Thr Glu Arg Gly Phe
145                 150                 155                 160

Val Pro Leu Lys Gly Phe Cys Gly His Gly Ile Gly Lys Lys Pro His
                165                 170                 175

Glu Glu Pro Glu Ile Pro Asn Tyr Leu Glu Lys Gly Val Lys Pro Asn
            180                 185                 190

Ser Gly Pro Lys Ile Lys Glu Gly Met Val Phe Cys Leu Glu Pro Met
        195                 200                 205

Val Cys Gln Lys Gln Gly Glu Pro Lys Ile Leu Ala Asp Lys Trp Ser
    210                 215                 220
```

-continued

```
Val Val Ser Val Asp Gly Leu Asn Thr Ser His His Glu His Thr Ile
225                 230                 235                 240

Ala Ile Val Gly Asn Lys Ala Val Ile Leu
                245                 250


<210> SEQ ID NO 23
<211> LENGTH: 20
<212> TYPE: DNA
<213> ORGANISM: Homo sapiens MetAP3-For primer
<220> FEATURE:
<221> NAME/KEY: misc_feature
<222> LOCATION: (1)...(1)
<223> OTHER INFORMATION: First base was incorrectly listed as T, now A
      in the parent application

<400> SEQUENCE: 23

aggacgaatg tggtaaaaag                                                   20


<210> SEQ ID NO 24
<211> LENGTH: 30
<212> TYPE: DNA
<213> ORGANISM: homo sapiens MAP3 FOR+ADAPT+ATG primer

<400> SEQUENCE: 24

ctagaattca tggcggcgcc cagtggcgtc                                        30


<210> SEQ ID NO 25
<211> LENGTH: 27
<212> TYPE: DNA
<213> ORGANISM: homo sapiens MAP3 REV-NotI primer

<400> SEQUENCE: 25

tgcggccgct caggcctcat ggggtag                                           27


<210> SEQ ID NO 26
<211> LENGTH: 17
<212> TYPE: DNA
<213> ORGANISM: homo sapiens MAP3 FOR2 primer

<400> SEQUENCE: 26

acaatcagcc acataac                                                      17


<210> SEQ ID NO 27
<211> LENGTH: 19
<212> TYPE: DNA
<213> ORGANISM: homo sapiens MAP3 FOR3 primer

<400> SEQUENCE: 27

ttctcttcac cactcaatc                                                    19


<210> SEQ ID NO 28
<211> LENGTH: 17
<212> TYPE: DNA
<213> ORGANISM: homo sapiens MAP3 FOR4 primer

<400> SEQUENCE: 28

gtttctcttt cccttgc                                                      17


<210> SEQ ID NO 29
<211> LENGTH: 21
<212> TYPE: DNA
<213> ORGANISM: homo sapiens MAP3 FOR5 primer

<400> SEQUENCE: 29
```

-continued gccacattca gccttcaagg c 21

<210> SEQ ID NO 30
<211> LENGTH: 20
<212> TYPE: DNA
<213> ORGANISM: homo sapiens MAP3 REV1 primer

<400> SEQUENCE: 30
atccctccgt gatgattggc 20

<210> SEQ ID NO 31
<211> LENGTH: 17
<212> TYPE: DNA
<213> ORGANISM: homo sapiens MAP3 REV2 primer

<400> SEQUENCE: 31
gcaagggaaa gagaaac 17

<210> SEQ ID NO 32
<211> LENGTH: 22
<212> TYPE: DNA
<213> ORGANISM: homo sapiens MAP3 REV1.2 primer

<400> SEQUENCE: 32
agcccctgct ctgcaagctg ca 22

<210> SEQ ID NO 33
<211> LENGTH: 21
<212> TYPE: DNA
<213> ORGANISM: homo sapiens MAP3 REV3 primer

<400> SEQUENCE: 33
tccatagcct agaggtgagg g 21

<210> SEQ ID NO 34
<211> LENGTH: 17
<212> TYPE: DNA
<213> ORGANISM: homo sapiens MAP3 REV4 primer

<400> SEQUENCE: 34
aaggccagct gaaccct 17

<210> SEQ ID NO 35
<211> LENGTH: 21
<212> TYPE: DNA
<213> ORGANISM: homo sapiens hmap1F1 primer

<400> SEQUENCE: 35
aagcggtctg ctcagtttga g 21

<210> SEQ ID NO 36
<211> LENGTH: 18
<212> TYPE: DNA
<213> ORGANISM: homo sapiens hmap1R1 primer

<400> SEQUENCE: 36
ggccgtgcac tgtcaagt 18

<210> SEQ ID NO 37
<211> LENGTH: 26
<212> TYPE: DNA
<213> ORGANISM: hmap1P1

<400> SEQUENCE: 37

-continued acaccctcct ggtcacagac actggc 26

<210> SEQ ID NO 38
<211> LENGTH: 23
<212> TYPE: DNA
<213> ORGANISM: homo sapiens hmap2F1 primer

<400> SEQUENCE: 38
gaccctccct cagttccaat atg 23

<210> SEQ ID NO 39
<211> LENGTH: 20
<212> TYPE: DNA
<213> ORGANISM: homo sapiens hmap2R1 primer

<400> SEQUENCE: 39
gtgggtgggt attcgcattc 20

<210> SEQ ID NO 40
<211> LENGTH: 34
<212> TYPE: DNA
<213> ORGANISM: homo sapiens hmap2P2 primer

<400> SEQUENCE: 40
acctgtatcc taatggtgta tttcccaaag gaca 34

<210> SEQ ID NO 41
<211> LENGTH: 20
<212> TYPE: DNA
<213> ORGANISM: homo sapiens hmap3F1 primer

<400> SEQUENCE: 41
ggcatcatgc aaacgacagt 20

<210> SEQ ID NO 42
<211> LENGTH: 19
<212> TYPE: DNA
<213> ORGANISM: hmap3R1 primer

<400> SEQUENCE: 42
actgcgccga cctttgatt 19

<210> SEQ ID NO 43
<211> LENGTH: 25
<212> TYPE: DNA
<213> ORGANISM: human hmap3P1 primer

<400> SEQUENCE: 43
agagccaatc atcacggagg gatcc 25

<210> SEQ ID NO 44
<211> LENGTH: 22
<212> TYPE: DNA
<213> ORGANISM: homo sapiens map2bF primer

<400> SEQUENCE: 44
ttggaagact gttcacgcaa gt 22

<210> SEQ ID NO 45
<211> LENGTH: 20
<212> TYPE: DNA
<213> ORGANISM: homo sapiens map2bR primer -continued

<400> SEQUENCE: 45
gtcaccggca ttgggagtat 20

<210> SEQ ID NO 46
<211> LENGTH: 31
<212> TYPE: DNA
<213> ORGANISM: homo sapiens map2bP primer

<400> SEQUENCE: 46
tggatgttct ctcaataatt gtgctgccca t 31

<210> SEQ ID NO 47
<211> LENGTH: 23
<212> TYPE: DNA
<213> ORGANISM: homo sapiens mp3bF primer

<400> SEQUENCE: 47
aacgtgctct gtcatggtat tcc 23

<210> SEQ ID NO 48
<211> LENGTH: 27
<212> TYPE: DNA
<213> ORGANISM: homo sapiens mp3bR primer

<400> SEQUENCE: 48
agccattgta atagactgtg acatcaa 27

<210> SEQ ID NO 49
<211> LENGTH: 35
<212> TYPE: DNA
<213> ORGANISM: homo sapiens mp3bP primer

<400> SEQUENCE: 49
acagtcgacc tcttcaggat ggagatatta tcaac 35

<210> SEQ ID NO 50
<211> LENGTH: 24
<212> TYPE: DNA
<213> ORGANISM: homo sapiens mp3cF primer

<400> SEQUENCE: 50
catggagaca cctctgaaac attt 24

<210> SEQ ID NO 51
<211> LENGTH: 22
<212> TYPE: DNA
<213> ORGANISM: homo sapiens mp3cR primer

<400> SEQUENCE: 51
cctggcaacc tccactaact tt 22

<210> SEQ ID NO 52
<211> LENGTH: 24
<212> TYPE: DNA
<213> ORGANISM: homo sapiens mp3cP primer

<400> SEQUENCE: 52
cacattcgtc ctcattgccc acca 24

<210> SEQ ID NO 53
<211> LENGTH: 20
<212> TYPE: DNA
<213> ORGANISM: homo sapiens hcycmesF primer

<400> SEQUENCE: 53
cccaccgtgt tcttcgacat 20

<210> SEQ ID NO 54
<211> LENGTH: 22
<212> TYPE: DNA
<213> ORGANISM: homo sapiens hcycmesR primer

<400> SEQUENCE: 54
tttctgctgt ctttgggacc tt 22

<210> SEQ ID NO 55
<211> LENGTH: 24
<212> TYPE: DNA
<213> ORGANISM: homo sapiens hcycmesP primer

<400> SEQUENCE: 55
cgcgtctcct ttgagctgtt tgca 24

<210> SEQ ID NO 56
<211> LENGTH: 24
<212> TYPE: DNA
<213> ORGANISM: homo sapiens revmp3cP primer

<400> SEQUENCE: 56
cacattcgtc cacattgccc acca 24

<210> SEQ ID NO 57
<211> LENGTH: 20
<212> TYPE: PRT
<213> ORGANISM: human MetAP1 peptide antigen 1

<400> SEQUENCE: 57

```
Asn Glu Thr Phe Phe Val Gly Glu Val Asp Asp Gly Ala Arg Lys Leu
 1               5                  10                  15

Val Gln Thr Thr
            20
```

<210> SEQ ID NO 58
<211> LENGTH: 20
<212> TYPE: PRT
<213> ORGANISM: human MetAP2 peptide antigen

<400> SEQUENCE: 58

```
Cys Ala Phe Thr Val Thr Phe Asn Pro Lys Tyr Asp Thr Leu Leu Lys
 1               5                  10                  15

Ala Val Lys Asp
            20
```

<210> SEQ ID NO 59
<211> LENGTH: 20
<212> TYPE: PRT
<213> ORGANISM: human MetAP3 peptide antigen-1

<400> SEQUENCE: 59

```
Ser Glu Thr Phe Leu Val Gly Asn Glu Asp Glu Ala Gly Lys Lys Leu
 1               5                  10                  15

Val Glu Val Ala
            20
```

<210> SEQ ID NO 60

-continued

<211> LENGTH: 20
<212> TYPE: PRT
<213> ORGANISM: human MetAP1 blocking peptide antigen

<400> SEQUENCE: 60

Gly Trp Gln Asp Glu Thr Trp Pro Asp Gly Trp Thr Ala Val Thr Arg
1 5 10 15

Asp Gly Lys Arg
20

<210> SEQ ID NO 61
<211> LENGTH: 20
<212> TYPE: PRT
<213> ORGANISM: human MetAP2 blocking peptide antigen

<400> SEQUENCE: 61

Cys Ser His Tyr Met Lys Asn Phe Asp Val Gly His Val Pro Ile Arg
1 5 10 15

Leu Pro Arg Thr
20

<210> SEQ ID NO 62
<211> LENGTH: 20
<212> TYPE: PRT
<213> ORGANISM: human MetAP3 blocking peptide antigen

<400> SEQUENCE: 62

Gly Ser Pro Glu Phe Lys Val Leu Glu Asp Ala Trp Thr Val Val Ser
1 5 10 15

Leu Asp Asn Gln
20

<210> SEQ ID NO 63
<211> LENGTH: 20
<212> TYPE: PRT
<213> ORGANISM: human MetAP3 peptide antigen-2

<400> SEQUENCE: 63

Ser Glu Thr Phe Leu Val Gly Asn Val Asp Glu Cys Gly Lys Lys Leu
1 5 10 15

Val Glu Val Ala
20

<210> SEQ ID NO 64
<211> LENGTH: 20
<212> TYPE: DNA
<213> ORGANISM: Artificial Sequence
<220> FEATURE:
<223> OTHER INFORMATION: MetAP-1 forward primer

<400> SEQUENCE: 64
acttgcatca agctgggcat 20

<210> SEQ ID NO 65
<211> LENGTH: 30
<212> TYPE: DNA
<213> ORGANISM: Artificial Sequence
<220> FEATURE:
<223> OTHER INFORMATION: MetAP-2 5' primer

<400> SEQUENCE: 65
ctagaattca tggcgggtgt ggaggaggta 30

-continued

```
<210> SEQ ID NO 66
<211> LENGTH: 30
<212> TYPE: DNA
<213> ORGANISM: Artificial Sequence
<220> FEATURE:
<223> OTHER INFORMATION: MetAP-2 3' primer

<400> SEQUENCE: 66

tgcggccgct taatagtcat ctcctctgct                                   30


<210> SEQ ID NO 67
<211> LENGTH: 5
<212> TYPE: PRT
<213> ORGANISM: Artificial Sequence
<220> FEATURE:
<223> OTHER INFORMATION: Methionine aminopeptidase substrate

<400> SEQUENCE: 67

Met Gly Met Met Lys
 1               5


<210> SEQ ID NO 68
<211> LENGTH: 334
<212> TYPE: PRT
<213> ORGANISM: Mouse methionine aminopeptidase type 3 (MetAP-3)

<400> SEQUENCE: 68

Met Ala Ala Pro Ile Gly Val Pro Leu Leu Val Arg Gly Gly Cys Gln
 1               5                  10                  15

Arg Ile Leu Ser Ser Pro Leu Asn His Ile Tyr Leu His Lys Arg Ser
            20                  25                  30

Gly Ser Gln Gln Arg Arg His Phe Phe Phe Trp Arg Gln Arg Asp Ile
        35                  40                  45

Ser His Ser Val Val Ser Pro Ala Ala Val Ser Pro Ala His Pro Val
    50                  55                  60

Pro Lys Arg Ile Lys Lys Pro Asp Tyr Val Thr Thr Gly Ile Val Pro
65                  70                  75                  80

Asp Trp Gly Asp Ser Ile Glu Val Lys Asp Glu Asp Gln Ile Gln Gly
                85                  90                  95

Leu Arg Glu Ala Cys Arg Leu Ala Arg His Val Leu Leu Leu Ala Gly
            100                 105                 110

Lys Ser Leu Lys Val Asp Met Thr Thr Glu Glu Ile Asp Ala Leu Val
        115                 120                 125

His Trp Glu Ile Ile Arg His Asp Ala Tyr Pro Ser Pro Leu Gly Tyr
    130                 135                 140

Gly Arg Phe Pro Lys Ser Val Cys Thr Ser Val Asn Asn Val Leu Cys
145                 150                 155                 160

His Gly Ile Pro Asp Ser Arg Pro Leu Gln Asp Gly Asp Ile Ile Asn
                165                 170                 175

Ile Asp Val Thr Val Tyr Tyr Asn Gly Tyr His Gly Asp Thr Ser Glu
            180                 185                 190

Thr Phe Leu Val Gly Asn Val Asp Glu Ser Gly Lys Lys Leu Val Glu
        195                 200                 205

Val Ala Arg Arg Cys Arg Asp Glu Ala Ile Ala Ala Cys Arg Ala Gly
    210                 215                 220

Ala Pro Phe Ser Val Ile Gly Asn Thr Ile Ser Arg Ile Thr His Gln
225                 230                 235                 240

Asn Gly Leu Gln Cys Pro His Phe Val Gly His Gly Ile Gly Ser Tyr
                245                 250                 255
```

-continued

```
Phe His Gly His Pro Glu Ile Trp His His Ala Asn Asp Ser Asp Leu
            260                 265                 270

Pro Met Glu Glu Gly Met Ala Phe Thr Ile Glu Pro Ile Ile Thr Glu
        275                 280                 285

Gly Ser Pro Glu Phe Lys Val Leu Glu Asp Ala Trp Thr Val Val Ser
    290                 295                 300

Leu Asp Asn Gln Arg Ser Ala Gln Phe Glu His Thr Val Leu Ile Thr
305                 310                 315                 320

Ser Arg Gly Ala Gln Ile Leu Thr Lys Leu Pro His Glu Ala


<210> SEQ ID NO 69
<211> LENGTH: 1026
<212> TYPE: DNA
<213> ORGANISM: human metAP-3 PCR fragment
<220> FEATURE:
<221> NAME/KEY: old_sequence
<222> LOCATION: (1)...(30)
<223> OTHER INFORMATION: nucleotides 1-30 of PCR primer SEQ ID NO: 24
<220> FEATURE:
<221> NAME/KEY: old_sequence
<222> LOCATION: (31)...(1017)
<223> OTHER INFORMATION: Nucelotides 18-1004 of MetAP-3 clone SEQ ID
      NO: 7 with majority of CDS and stop codon
<220> FEATURE:
<221> NAME/KEY: old_sequence
<222> LOCATION: (1018)...(1026)
<223> OTHER INFORMATION: Reverse complement of nucleotides 1-9 of PCR
      primer SEQ ID NO: 25
<220> FEATURE:
<221> NAME/KEY: CDS
<222> LOCATION: (10)...(1017)
<223> OTHER INFORMATION: CDS of metAP-3 within PCR fragment

<400> SEQUENCE: 69

ctagaattc atg gcg gcg ccc agt ggc gtc cac ctg ctc gtc cgc aga ggt      51
Met Ala Ala Pro Ser Gly Val His Leu Leu Val Arg Arg Gly
 1               5                  10

tct cat aga att ttc tct tca cca ctc aat cat atc tac tta cac aag       99
Ser His Arg Ile Phe Ser Ser Pro Leu Asn His Ile Tyr Leu His Lys
 15                  20                  25                  30
cag tca agc agt caa caa aga aga aat ttc ttt ttt cgg aga caa aga      147
Gln Ser Ser Ser Gln Gln Arg Arg Asn Phe Phe Phe Arg Arg Gln Arg
                 35                  40                  45

gat att tca cac agt ata gtt ttg ccg gct gca gtt tct tca gct cat      195
Asp Ile Ser His Ser Ile Val Leu Pro Ala Ala Val Ser Ser Ala His
             50                  55                  60

ccg gtt cct aag cac ata aag aag cca gac tat gtg acg aca ggc att      243
Pro Val Pro Lys His Ile Lys Lys Pro Asp Tyr Val Thr Thr Gly Ile
         65                  70                  75

gta cca gac tgg gga gac agc ata gaa gtt aag aat gaa gat cag att      291
Val Pro Asp Trp Gly Asp Ser Ile Glu Val Lys Asn Glu Asp Gln Ile
     80                  85                  90

caa ggg ctt cat cag gct tgt cag ctg gcc cgc cac gtc ctc ctc ttg      339
Gln Gly Leu His Gln Ala Cys Gln Leu Ala Arg His Val Leu Leu Leu
 95                 100                 105                 110

gct ggg aag agt tta aag gtt gac atg aca act gaa gag ata gat gct      387
Ala Gly Lys Ser Leu Lys Val Asp Met Thr Thr Glu Glu Ile Asp Ala
                115                 120                 125

ctt gtt cat cgg gaa atc atc agt cat aat gcc tat ccc tca cct cta      435
Leu Val His Arg Glu Ile Ile Ser His Asn Ala Tyr Pro Ser Pro Leu
            130                 135                 140

ggc tat gga ggt ttt cca aaa tct gtt tgt acc tct gta aac aac gtg      483
Gly Tyr Gly Gly Phe Pro Lys Ser Val Cys Thr Ser Val Asn Asn Val
        145                 150                 155
```

-continued

```
ctc tgt cat ggt att cct gac agt cga cct ctt cag gat gga gat att      531
Leu Cys His Gly Ile Pro Asp Ser Arg Pro Leu Gln Asp Gly Asp Ile
    160                 165                 170

atc aac att gat gtc aca gtc tat tac aat ggc tac cat gga gac acc      579
Ile Asn Ile Asp Val Thr Val Tyr Tyr Asn Gly Tyr His Gly Asp Thr
175                 180                 185                 190

tct gaa aca ttt ttg gtg ggc aat gtg gac gaa tgt ggt aaa aag tta      627
Ser Glu Thr Phe Leu Val Gly Asn Val Asp Glu Cys Gly Lys Lys Leu
                195                 200                 205

gtg gag gtt gcc agg agg tgt aga gat gaa gca att gca gct tgc aga      675
Val Glu Val Ala Arg Arg Cys Arg Asp Glu Ala Ile Ala Ala Cys Arg
            210                 215                 220

gca ggg gct ccc ttc tct gta att gga aac aca atc agc cac ata act      723
Ala Gly Ala Pro Phe Ser Val Ile Gly Asn Thr Ile Ser His Ile Thr
        225                 230                 235

cat cag aat ggt ttt caa gtc tgt cca cat ttt gtg gga cat gga ata      771
His Gln Asn Gly Phe Gln Val Cys Pro His Phe Val Gly His Gly Ile
    240                 245                 250

gga tct tac ttt cat gga cat cca gaa att tgg cat cat gca aac gac      819
Gly Ser Tyr Phe His Gly His Pro Glu Ile Trp His His Ala Asn Asp
255                 260                 265                 270

agt gat cta ccc atg gag gag ggc atg gca ttc act ata gag cca atc      867
Ser Asp Leu Pro Met Glu Glu Gly Met Ala Phe Thr Ile Glu Pro Ile
                275                 280                 285

atc acg gag gga tcc cct gaa ttt aaa gtc ctg gag gat gca tgg act      915
Ile Thr Glu Gly Ser Pro Glu Phe Lys Val Leu Glu Asp Ala Trp Thr
            290                 295                 300

gtg gtc tcc cta gac aat caa agg tcg gcg cag ttc gag cac acg gtt      963
Val Val Ser Leu Asp Asn Gln Arg Ser Ala Gln Phe Glu His Thr Val
        305                 310                 315

ctg atc acg tcg agg ggc gcg cag atc ctg acc aaa cta ccc cat gag     1011
Leu Ile Thr Ser Arg Gly Ala Gln Ile Leu Thr Lys Leu Pro His Glu
    320                 325                 330

gcc tga gcggccgca                                                   1026
Ala  *
335
```